US010364210B2

(12) United States Patent
Wood et al.

(10) Patent No.: US 10,364,210 B2
(45) Date of Patent: Jul. 30, 2019

(54) DIAMINE COMPOUNDS, DINITRO COMPOUNDS AND OTHER COMPOUNDS, AND METHODS OF PRODUCING THEREOF AND USES RELATED THEREOF

(71) Applicant: MICROMIDAS, INC., West Sacramento, CA (US)

(72) Inventors: Alex B. Wood, Sacramento, CA (US); Makoto Nathanael Masuno, Elk Grove, CA (US); Ryan L. Smith, Sacramento, CA (US); John Albert Bissell, II, Sacramento, CA (US); Robert Joseph Araiza, Sacramento, CA (US); Dimitri A. Hirsch-Weil, Sacramento, CA (US)

(73) Assignee: MICROMIDAS, INC., West Sacramento, CA (US)

( * ) Notice: Subject to any disclaimer, the term of this patent is extended or adjusted under 35 U.S.C. 154(b) by 0 days.

(21) Appl. No.: 15/507,009

(22) PCT Filed: Aug. 27, 2015

(86) PCT No.: PCT/US2015/047237
§ 371 (c)(1),
(2) Date: Feb. 27, 2017

(87) PCT Pub. No.: WO2016/033348
PCT Pub. Date: Mar. 3, 2016

(65) Prior Publication Data
US 2017/0275236 A1    Sep. 28, 2017

Related U.S. Application Data

(60) Provisional application No. 62/043,284, filed on Aug. 28, 2014.

(51) Int. Cl.
| | | |
|---|---|---|
| C07D 307/02 | (2006.01) |
| C07C 211/51 | (2006.01) |
| C07D 307/14 | (2006.01) |
| C07D 307/38 | (2006.01) |
| C07D 307/42 | (2006.01) |
| C07D 307/52 | (2006.01) |
| C07D 307/54 | (2006.01) |
| C07C 205/04 | (2006.01) |
| C07C 211/09 | (2006.01) |
| C07C 211/27 | (2006.01) |
| C07C 255/35 | (2006.01) |
| C08G 69/04 | (2006.01) |
| C08G 69/08 | (2006.01) |
| C08G 69/26 | (2006.01) |
| C08G 69/28 | (2006.01) |
| C07C 209/32 | (2006.01) |
| C08F 210/02 | (2006.01) |
| C08G 73/02 | (2006.01) |

(52) U.S. Cl.
CPC .......... *C07C 211/51* (2013.01); *C07C 205/04* (2013.01); *C07C 209/32* (2013.01); *C07C 211/09* (2013.01); *C07C 211/27* (2013.01); *C07C 255/35* (2013.01); *C07D 307/14* (2013.01); *C07D 307/38* (2013.01); *C07D 307/42* (2013.01); *C07D 307/52* (2013.01); *C07D 307/54* (2013.01); *C08F 210/02* (2013.01); *C08G 69/04* (2013.01); *C08G 69/08* (2013.01); *C08G 69/26* (2013.01); *C08G 69/28* (2013.01); *C08G 73/02* (2013.01); *C07C 2601/16* (2017.05)

(58) Field of Classification Search
CPC ... C07C 211/51; C07C 211/27; C07C 211/09; C07C 209/32; C07C 255/35; C07C 205/04; C07C 2601/16; C08G 73/02; C08G 69/04; C08G 69/28; C08G 69/26; C08G 69/08; C08F 210/02; C07D 307/42; C07D 307/38; C07D 307/14; C07D 307/52; C07D 307/54
USPC ........................................................ 549/491
See application file for complete search history.

(56) References Cited

FOREIGN PATENT DOCUMENTS

WO    2001/07400 A1    2/2001
WO    2015/057365 A2    4/2015

OTHER PUBLICATIONS

Chang et al., "Synthesis of the Insecticide Prothrin and Its Analogues from Biomass-Derived 5-(Chloromethyl) Furfural", Journal of Agriculture and Food Chemistry, vol. 62, 2014, pp. 476-480.
Cheng et al., "Production of Targeted Aromatics by using Diels-Alder Classes of Reactions with Furans and Olefins over ZSM-5", Green Chemistry, vol. 14, 2012, pp. 3114-3125.
Karakhanov et al., "The Synthesis and Properties of Unsaturated Nitro-Compounds of the Furan Series", Russian Chemical Reviews, vol. 62, No. 2, 1993, pp. 169-192.

(Continued)

*Primary Examiner* — Taylor V Oh
(74) *Attorney, Agent, or Firm* — Morrison & Foerster LLP

(57) ABSTRACT

Provided herein are (phenylene)dialkanamines, and methods of producing such (phenylene)dialkanamines from various furanyl and benzyl compounds. Such furanyl compounds may include, for example, bis(nitroalkyl)furans, bis(aminoalkyl)furans, and nitroalkyl(furan)acetonitriles. Such compounds may include, for example, bis(nitroalkyl)benzenes. Provided herein are also alkyldiamines, and methods for producing such alkyldiamines from furanyl compounds.

14 Claims, 4 Drawing Sheets

(56) References Cited

OTHER PUBLICATIONS

Kilway et al., "Control of Functional Group Proximity and Direction by Conformational Networks: Synthesis and Stereodynamics of Persubstituted Arenes", Tetrahedron, vol. 57, 2001, pp. 3615-3627.
Nakao et al., "Syntheses and Antimicrobial Activities of 5-Cyano-2-Furaldehyde and its Derivatives", Yakugaku Zasshi. vol. 93, No. 11, 1973, pp. 1526-1529. (See Communication under 37 CFR § 1.98(a) (3)).
International Search Report and Written Opinion for PCT Application. No. PCT/US2015/047237, dated Dec. 4, 2015, 7 pages.
International Preliminary Report on Patentability for PCT Patent Application No. PCT/US2015/047237, dated Mar. 9, 2017, 6 pages.
Perez-Balderas et al., "Synthesis of Multivalent Neoglycoconjugates by 1,3 Dipolar Cycloaddition of Nitrile Oxides and Alkynes and Evaluation of their Lectin-Binding Affinities", Tetrahedron, vol. 61, 2005, pp. 9338-9348.
Roland et al., "Cyanocarbon Chemistry. XVIII.' Tricyanovinylation of Hydrazones and Other Nucleophilic Substances", Journal of the American Chemical Society, vol. 83, Apr. 5, 1961, pp. 1652-1657.
Usova et al., "Synthesis of 5-(5-R-2-furyl)Thiazole Derivatives by the Reaction of 2-(5-R-furfuryl)Thiuronium Salts with Acetic Anhydride", Chemistry of Heterocyclic Compounds, vol. 26, 1990, pp. 477-482.

DIAMINE COMPOUNDS, DINITRO COMPOUNDS AND OTHER COMPOUNDS, AND METHODS OF PRODUCING THEREOF AND USES RELATED THEREOF

CROSS-REFERENCE TO RELATED APPLICATIONS

This application is a U.S. National Phase Patent Application of PCT/US2015/047237, filed Aug. 27, 2015, which claims priority to U.S. Provisional Patent Application No. 62/043,284, filed Aug. 28, 2014, the disclosures of which are herein incorporated by reference in their entirety.

FIELD

The present disclosure relates generally to diamine compounds, dinitro compounds, and other compounds, and methods of producing such compounds, and more specifically to compounds such as (phenylene)dialkanamines, alkyldiamines, bis(aminoalkyl)furans, bis(aminoalkyl)tetrahydrofurans, bis(nitroalkyl)furans and bis(nitroalkyl)benzenes.

BACKGROUND

Nylon is a family of synthetic polymers that are used in many applications, including clothes fabrics, musical strings, rope and other materials. Various methods are known in the art to produce nylon. For example, nylon may be produced from hexamethylene diamine (as referred to as hexane-1,6-diamine), which may be obtained from butadiene. Butadiene may be obtained from cracking of hydrocarbons, and not typically obtained from renewable sources. Further, precursors like butadiene may also be subject to global energy price volatilities. Thus, what is needed in the art are alternative methods to produce precursors suitable for use to produce nylon and other polymers.

BRIEF SUMMARY

Provided herein are compounds that may be obtained from renewable sources, such as biomass, suitable for use as precursors to produce various polymers, including for example nylon. For example, provided herein are methods to produce octamethylene diamine (also referred to as octane-1,8-diamine) that may be suitable for use as a precursor to produce nylon. Provided herein are also methods to produce other diamine compounds, such as (phenylene)dialkanamines, that may be suitable for use as precursors to produce specialty polymers and other polymers.

In some aspects, provided is a method that includes reducing a furan of formula (B) to produce a furan of formula (B-I), a furan of formula (B-IIa), a tetrahydrofuran of formula (B-IIb), an alkyldiamine of formula (B-III), or any mixtures thereof, wherein:
the furan of formula (B) is:

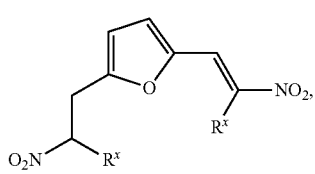

(B)

wherein $R^x$ is H or alkyl;

the furan of formula (B-I) is:

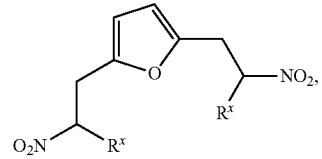

(B-I)

wherein $R^x$ is as defined for formula (B) above;
the furan of formula (B-IIa) is:

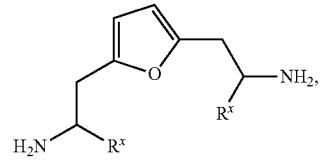

(B-IIa)

wherein $R^x$ is as defined for formula (B) above;
the tetrahydrofuran of formula (B-IIb) is:

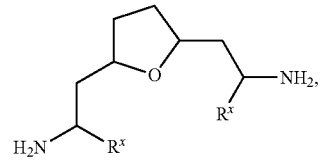

(B-IIb)

wherein $R^x$ is as defined for formula (B) above; and
the alkyldiamine of formula (B-III) is:

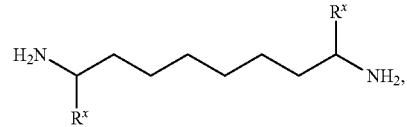

(B-III)

wherein $R^x$ is as defined for formula (B) above.

In one aspect, provided is a furan of formula (B-I), a furan of formula (B-IIa), a tetrahydrofuran of formula (B-IIb), or an alkyldiamine of formula (B-III) produced according to any of the methods described herein.

In certain aspects, provided is also a method that includes:
combining a furan of formula (B-I), alkene and catalyst to form a reaction mixture; and
producing a compound of formula (C) from at least a portion of the furan of formula (B-I) and ethylene in the reaction mixture, wherein:
the compound of formula (C) is:

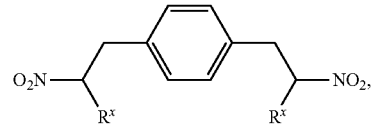

(C)

wherein $R^x$ is as defined for formula (B-I) above.

In some variations, the alkene is ethylene.

In one aspect, provided is a furan of formula (B-I) produced according to any of the methods described herein.

In certain aspects, provided is a method that includes:

reducing the compound of formula (C) to produce a compound of formula (C-I), wherein:

the compound of formula (C-I) is:

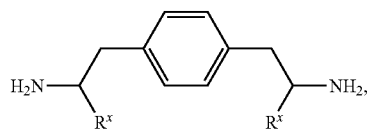
(C-I)

wherein $R^x$ is as defined for formula (C) above.

In one aspect, provided is a compound of formula (C) produced according to any of the methods described herein.

In certain aspects, provided is a method that includes:

combining a furan of formula (B-IIa), ethylene and catalyst to form a reaction mixture; and producing a compound of formula (C-I) from at least a portion of the furan of formula (B-IIa) and ethylene in the reaction mixture, wherein:

the compound of formula (C-I) is:

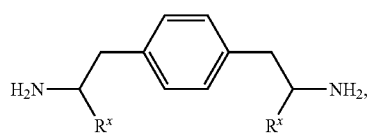
(C-I)

wherein $R^x$ is as defined for formula (B-IIa) above.

In one aspect, provided is a furan of formula (B-IIa) produced according to any of the methods described herein. In another aspect, provided is a furan of formula (C-I) produced according to any of the methods described herein.

In other aspects, provided is a method that includes:

combining a furan of formula (A) with a nitroalkane of formula (I) to produce the furan of formula (B), wherein:

the furan of formula (A) is:

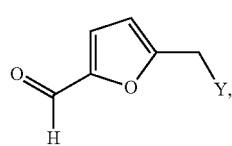
(A)

wherein Y is halo; and the nitroalkane of formula (I) is:

$(R^xCH_2)NO_2$ (I), wherein $R^x$ is as defined for formula (B) above.

In another aspect, provided herein is a method that includes: combining a furan of formula (A) with a nitroalkane of formula (I) to produce a furan of formula (Q), wherein:

the furan of formula (A) is:

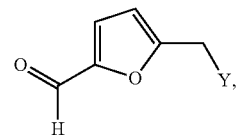
(A)

wherein Y is halo;

the nitroalkane of formula (I) is:

$(R^xH_2)NO_2$ (I), wherein $R^x$ is H or alkyl; and the furan of formula (Q) is:

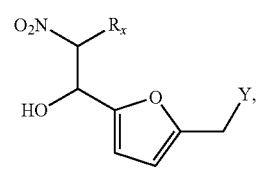
(Q)

wherein Y is as defined for formula (A) above, and $R^x$ is as defined for formula (I) above.

In some embodiments, the furan of formula (A) is combined with a nitroalkane of formula (I) in the presence of a base and optionally solvent. In certain embodiments, the furan of formula (Q) is converted a furan of formula (R), wherein:

the furan of formula (R) is:

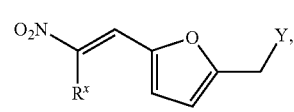
(R)

wherein Y and $R^x$ are as defined for formula (Q) above.

In another aspect, provided herein is a method that includes: reducing a furan of formula (N) to produce a furan of formula (N-I), wherein:

the furan of formula (N) is:

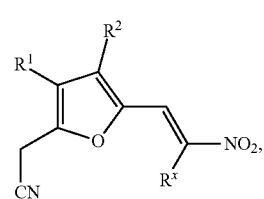
(N)

wherein:

$R^x$ is H or alkyl; and $R^1$ and $R^2$ are independently H or alkyl; and the furan of formula (N-I) is:

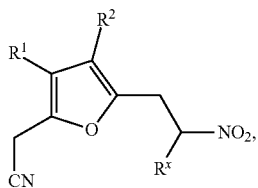

(N-I)

wherein $R^x$, $R^1$ and $R^2$ are as defined for formula (N) above.

In another aspect, provided herein is a method that includes: combining a furan of formula (A) with a nitroalkane of formula (I) to produce a furan of formula (Q), wherein:
the furan of formula (A) is:

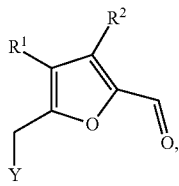

(A)

wherein:
Y is halo; and
$R^1$ and $R^2$ are independently H or alkyl;
the nitroalkane of formula (I) is:

(I), wherein $R^x$ is H or alkyl; and
the furan of formula (Q) is:

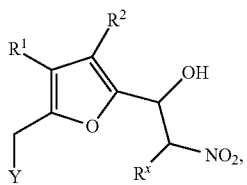

(Q)

wherein Y, $R^1$ and $R^2$ are as defined for formula (A) above, and $R^x$ is as defined for formula (I) above.

In one aspect, provided herein is a method that includes: converting a furan of formula (Q) to produce a furan of formula (R), wherein:
the furan of formula (Q) is:

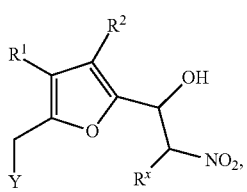

(Q)

wherein:
Y is halo;
$R^x$ is H or alkyl; and
$R^1$ and $R^2$ are independently H or alkyl; and
the furan of formula (R) is:

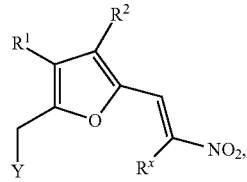

(R)

wherein Y, $R^1$, $R^2$ and $R^x$ are as defined for formula (Q) above.

In another aspect, provided herein is a method that includes: combining a furan of formula (A) with a nitroalkane of formula (I), base, and N≡CH or N≡C⁻ to produce a furan of formula (N), wherein:
the furan of formula (A) is:

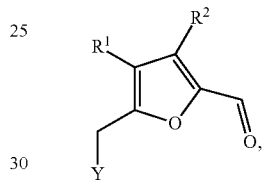

(A)

Y is halo; and
$R^1$ and $R^2$ are independently H or alkyl;
the nitroalkane of formula (I) is:

(I), wherein $R^x$ is H or alkyl; and
the furan of formula (N) is:

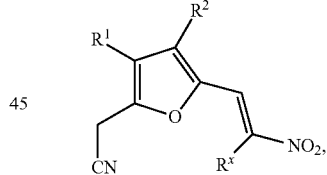

(N)

wherein Y, $R^1$ and $R^2$ are as defined for formula (A) above and $R^x$ is as defined for formula (I) above.

In one aspect, provided herein is a method that includes: reducing a furan of formula (N) to produce a furan of formula (N-IIa), a tetrahydrofuran of formula (N-IIb), or a mixture thereof, wherein:
the furan of formula (N) is:

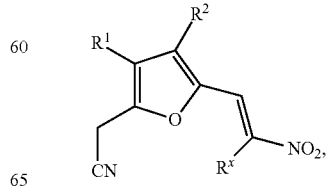

(N)

wherein $R^1$, $R^2$ and $R^x$ are independently H or alkyl;

the furan of formula (N-IIa) is:

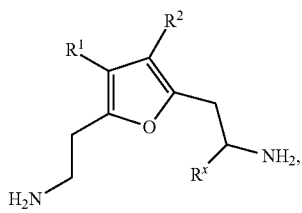
(N-IIa)

wherein $R^x$, $R^1$ and $R^2$ are as defined for formula (N) above; and the tetrahydrofuran of formula (N-IIb) is:

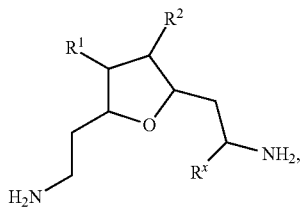
(N-IIb)

wherein $R^x$, $R^1$ and $R^2$ are as defined for formula (N) above.

In yet another aspect, provided herein is a compound of formula (AB), a compound of formula (B), a compound of formula (B-I), a compound of formula (B-IIa), a compound of formula (B-IIb), a compound of formula (B-III), a compound of formula (C), a compound of formula (C-I), a compound of formula (M), a compound of formula (MN), a compound of formula (N), a compound of formula (N-I), a compound of formula (N-IIa), a compound of formula (N-IIb), a compound of formula (P), a compound of formula (P-I), a compound of formula (Q), or a compound of formula (R):

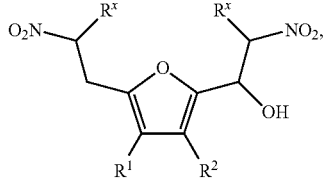
(AB)

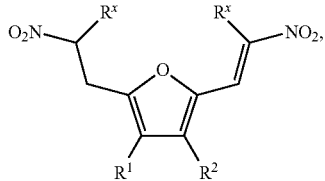
(B)

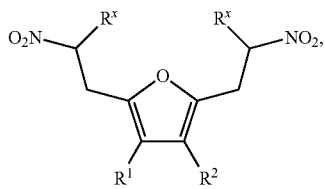
(B-I)

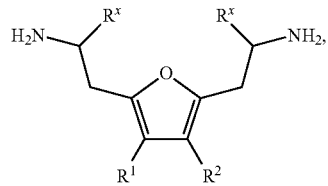
(B-IIa)

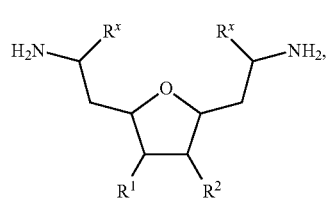
(B-IIb)

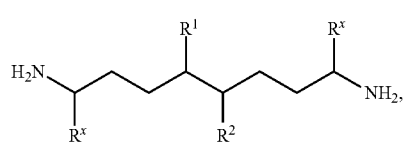
(B-III)

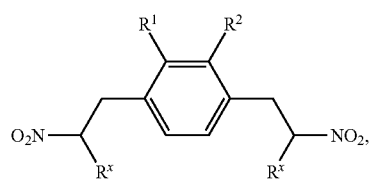
(C)

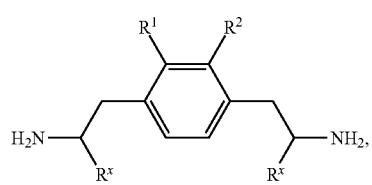
(C-I)

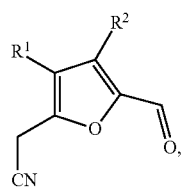
(M)

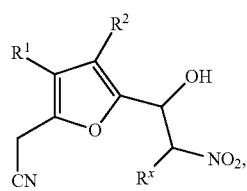
(MN)

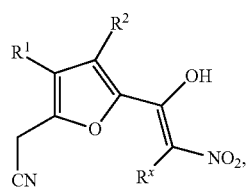
(N)

-continued

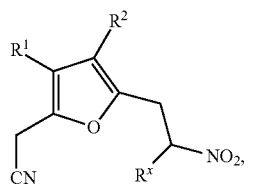
(N-I)

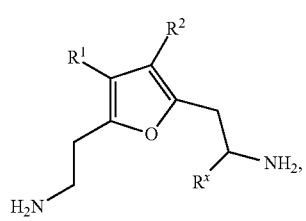
(N-IIa)

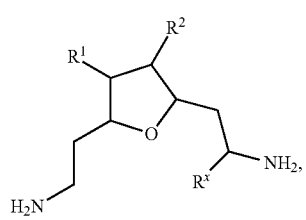
(N-IIb)

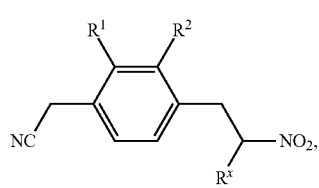
(P)

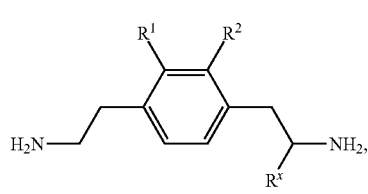
(P-I)

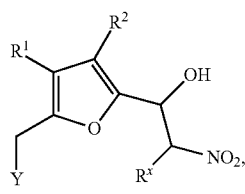
(Q)

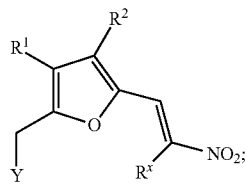
(R)

wherein Y is halo, and $R^1$, $R^2$ and $R^x$ are independently H or alkyl, where applicable.

Provided herein are also compositions comprising one or more compounds selected from formulae (AB), (B), (B-I), (B-IIa), (B-IIb), (B-III), (C), (C-I), (M), (MN), (N), (N-I), (N-IIa), (N-IIb), (P), (P-I), (Q), and (R). It should be understood that the compounds described herein include any isomers of such compounds where applicable, including any stereoisomers. For example, the compounds described herein and compounds produced according to the methods described herein may include cis isomers, trans isomers, and enantiomers, where applicable.

In another aspect, provided herein are methods of producing a polymer that include: combining a polymerization catalyst with one or more compounds selected from formulae (AB), (B), (B-I), (B-IIa), (B-IIb), (B-III), (C), (C-I), (M), (MN), (N), (N-I), (N-IIa), (N-IIb), (P), (P-I), (Q), and (R), and producing a polymer.

DESCRIPTION OF THE FIGURES

The present application can be understood by reference to the following description taken in conjunction with the accompanying figures.

DETAILED DESCRIPTION

Figure 1:
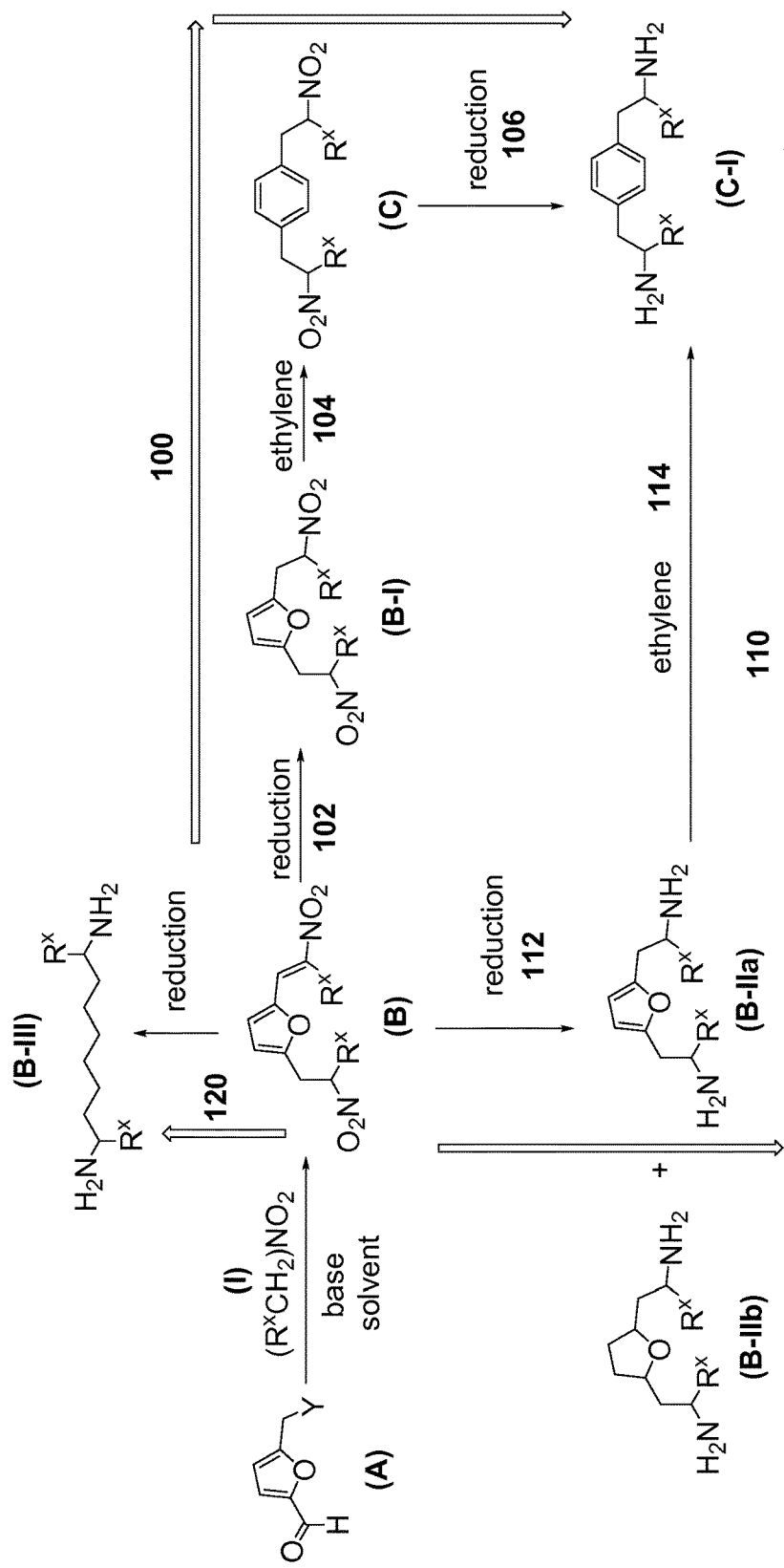
FIG. 1 depicts an exemplary process to produce an example of a (phenylene)dialkanamine of formula (C-I), an example of a alkyldiamine of formula (B-III) and other compounds from an example of a furan of formula (B).

The following description sets forth exemplary methods, parameters and the like. It should be recognized, however, that such description is not intended as a limitation on the scope of the present disclosure but is instead provided as a description of exemplary embodiments.

Provided herein are (phenylene)dialkanamines, alkyldiamines, and other diamine compounds and dinitro compounds, and methods for producing such compounds.

Compounds of Formula (AB)

In some aspects, provided herein are nitroalkyl(furan)nitroethanol compounds. In some variations, the nitroalkyl(furan)nitroethanol compounds are compounds of formula (AB):

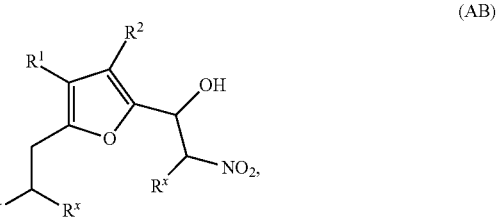
(AB)

wherein:
$R^x$ is H or alkyl; and
$R^1$ and $R^2$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

For example, in certain embodiments, $R^1$ and $R^2$ are H, and the compound of formula (AB) is:

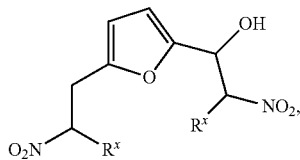

wherein $R^x$ is H or alkyl.

In other embodiments, $R^x$, $R^1$ and $R^2$ are all H, and the compound of formula (AB) is:

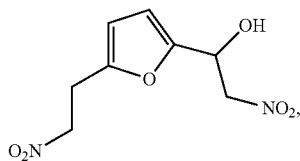 [SMILES: O=[N+]([O-])CCc1ccc(C(O)C[N+](=O)[O-])o1]

Methods of Producing Compounds of Formula (AB)

In certain aspects, provided herein are also methods of producing nitroalkyl(furan)nitroethanol compounds, including, for example, the compounds of formula (AB). Variations of the methods of producing nitroalkyl(furan)nitroethanol compounds, including, for example, the compounds of formula (AB), are exemplified in General Reaction Scheme AB described below.

General Reaction Scheme AB

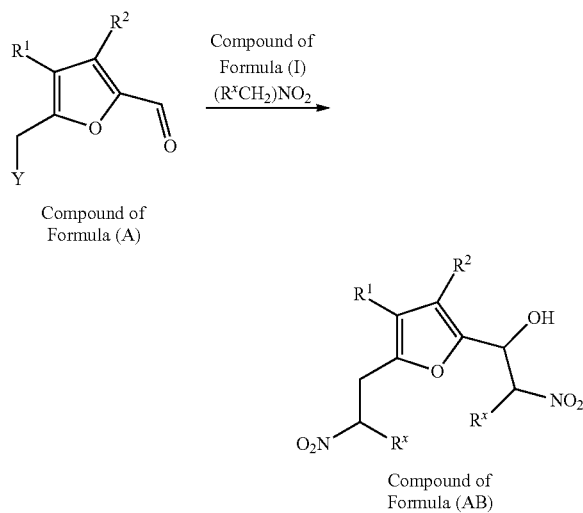

General Reaction Scheme AB depicts an exemplary reaction to produce a furan of formula (AB), wherein $R^1$ and $R^2$ are independently H or alkyl, and $R^x$ is H or alkyl, from a compound of formula (A), wherein $R^1$ and $R^2$ are independently H or alkyl, and Y is halo, and a compound of formula (I), wherein $R^x$ is H or alkyl.

In some variations of the reaction depicted in General Reaction Scheme AB, the compound of formula (A) and the nitroalkane of formula (I) are combined in the presence of a base and optionally a solvent to produce the compound of formula (AB). Any suitable base may be used.

For example, in some variations, the base is a non-nucleophilic base. In certain variations, the base is a non-nucleophilic base that forms a weak acid upon protonation. In certain variations, the base is cesium carbonate ($CsCO_3$) or an amine, such as triethylamine. In other variations, the base is ammonium acetate or alumina. A combination of any of the bases described herein may also be used.

In some variations, the solvent includes an aromatic solvent or an alkyl acetate solvent. In one variation, the solvent is toluene, methyl acetate, ethyl acetate, or propyl acetate. A combination of any of the solvents described herein may also be used.

In some variations, the compound of formula (A) is combined with the nitroalkane of formula (I) to produce the furan of formula (AB) at a temperature between 0° C. and 100° C., between 10° C. and 100° C., between 10° C. and 50° C., between 10° C. and 30° C., or between 20° C. and 30° C. In some variations, the compound of formula (A) is combined with the nitroalkane of formula (I) to produce the furan of formula (AB) at a pressure between 1 atma to 2 atma.

Thus, in certain aspects, provided herein are methods of producing a compound of formula (AB) by:
combining a compound of formula (A) with a nitroalkane of formula (I), to produce a furan of formula (AB).

In some variations, the furan of formula (A) is:

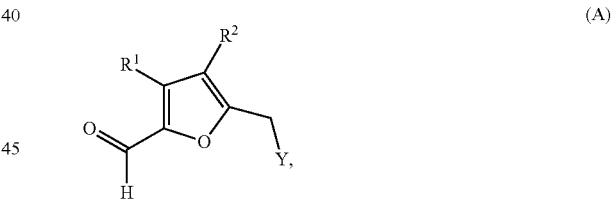

wherein:
Y is halo; and
$R^1$ and $R^2$ are independently H or alkyl.

In some variations, Y is chloro. In other variations, Y is bromo, iodo, or fluoro.

In some variations, the nitroalkane compound of formula (I) is:

$$(R^xCH_2)NO_2 \quad (I),$$

wherein $R^x$ is H or alkyl.

It should be understood that when the compound of formula (A) is used to produce the furan of formula (AB), $R^1$ and $R^2$ in formulae (A) and (AB) are the same. It should be further understood that when the compound of formula (I) is used to produce the furan of formula (AB), $R^x$ in formulae (I) and (AB) are the same.

In some variations, combining a compound of formula (A) and a nitroalkane of formula (I) produces a compound of formula (AB); a compound of formula (Q); a compound of formula (B); or a compound of formula (R); or any combinations thereof. The compounds of formulae (Q), (B), and (R) are described in further detail below.

Compounds of Formula (B)

In some aspects, provided herein are dinitro furan compounds. In some variations, the dinitro furan compounds are compounds of formula (B):

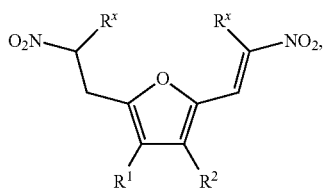

(B)

wherein:

$R^x$ is H or alkyl; and $R^1$ and $R^2$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

For example, in certain embodiments, $R^1$ and $R^2$ are H, and the compound of formula (B) is:

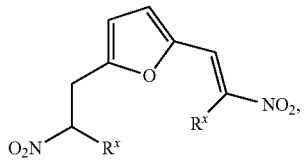

wherein $R^x$ is H or alkyl.

In other embodiments, $R^x$, $R^1$ and $R^2$ are all H, and the compound of formula (B) is:

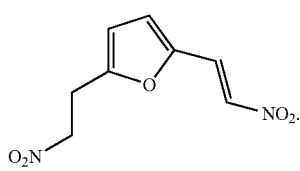 [SMILES: O=[N+]([O-])/C=C/c1ccc(CC[N+](=O)[O-])o1]

In yet other embodiments, $R^x$ is methyl, $R^1$ and $R^2$ are both H, and the compound of formula (B) is:

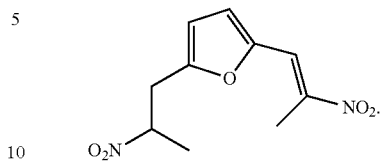

Methods of Producing Compounds of Formula (B)

In certain aspects, provided herein are also methods of producing dinitro vinyl furans, including, for example, the compounds of formula (B). With reference to FIG. 1, a (haloalkyl)furan, including, for example, a compound of formula (A), can undergo a nucleophilic substitution and nitro-aldol reaction with an nitroalkane compound of formula (I) to produce a furan of formula (B). FIG. 1 depicts the combination of an example of a (haloalkyl)furan of formula (A) (wherein $R^1$ and $R^2$ are H, and Y is chloro) with a nitroalkane compound of formula (I) in the presence of a base and solvent to produce an example of a furan of formula (B) (wherein $R^1$ and $R^2$ are H).

Variations of the methods of producing dinitro vinyl furans, including, for example, the compounds of formula (B), are exemplified in General Reaction Scheme B described below.

General Reaction Scheme B

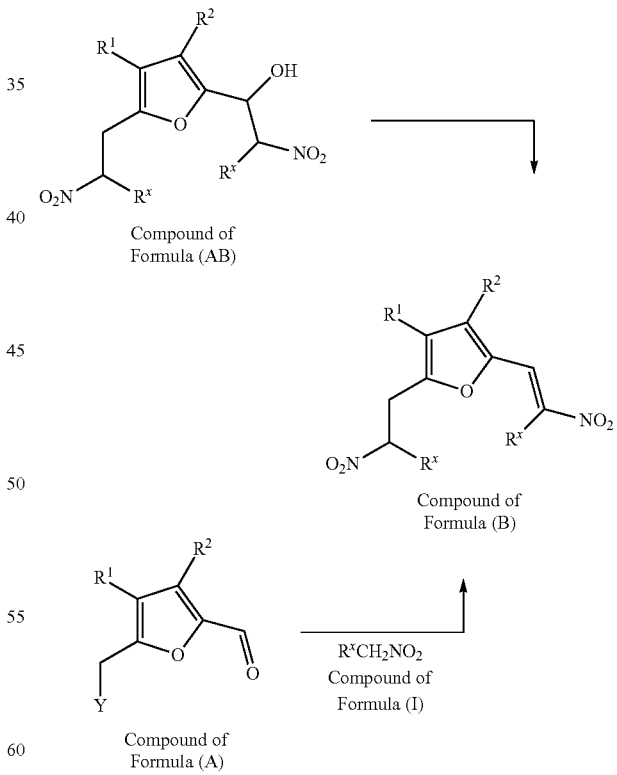

General Reaction Scheme B depicts an exemplary reaction to produce a furan of formula (B), wherein $R^1$ and $R^2$ are independently H or alkyl, and $R^x$ is H or alkyl, from a compound of formula (AB), wherein $R^1$ and $R^2$ are independently H or alkyl, and $R^x$ is H or alkyl. General Reaction Scheme B also depicts an exemplary reaction to produce a furan of formula (B), wherein $R^1$ and $R^2$ are independently H or alkyl, and $R^x$ is H or alkyl, from a compound of formula (A), wherein $R^1$ and $R^2$ are independently H or alkyl, and Y is halo, and a compound of formula (I), wherein $R^x$ is H or alkyl.

In some variations, the compound of formula (AB) is combined with an acid catalyst to produce the furan of formula (B). Any suitable acid catalyst may be used. For example, in some embodiments, a mineral acid (such as phosphoric acid or HCl) catalyst is used. In one embodiment, HCl is used as an acid catalyst. In some variations, the compound of formula (AB) is dehydrated to produce the furan of formula (B) at a temperature of 25° C. In some variations, the compound of formula (AB) is dehydrated at a pH below or equal to 2 to produce the furan of formula (B).

Thus, in certain aspects, provided herein are methods of producing a compound of formula (B) by:
converting a compound of formula (AB) to a compound of formula (B).

It should be understood that when the compound of formula (AB) is used to produce the furan of formula (B), $R^1$, $R^2$, and $R^x$ in formulae (AB) and (B) are the same.

In some variations of the reaction depicted in General Reaction Scheme B, the compound of formula (A) and the nitroalkane of formula (I) are combined in the presence of a base and optionally a solvent to produce the compound of formula (B). Any suitable base may be used.

For example, in some variations, the base is a non-nucleophilic base. In certain variations, the base is a non-nucleophilic base that forms a weak acid upon protonation. In certain variations, the base is cesium carbonate ($CsCO_3$) or an amine, such as triethylamine. In other variations, the base is ammonium acetate or alumina. A combination of any of the bases described herein may also be used.

In certain variations, a furan of formula (A) is combined with a nitroalkane of formula (I) in the presence of a base and optionally solvent to produce a reaction mixture, and an acid is added to the reaction mixture to produce the furan of formula (B). Any suitable base and acid may be used. In some variations, the acid is a mineral acid (such as phosphoric acid or HCl) or a carboxylic acid. For example, in one embodiment, a furan of formula (A) is combined with a nitroalkane of formula (I) in the presence of n-butyllithium and optionally solvent to form a reaction mixture, then HCl is added to the reaction mixture to produce the furan of formula (B). In some embodiments, the solvent is hexane. In certain embodiments, 12 M HCl is added to the reaction mixture.

In some variations, the solvent includes an aromatic solvent or an alkyl acetate solvent. In one variation, the solvent is toluene, methyl acetate, ethyl acetate, or propyl acetate. A combination of any of the solvents described herein may also be used.

In some variations, the compound of formula (A) is combined with the nitroalkane of formula (I) to produce the furan of formula (B) at a temperature between 10° C. and 100° C., between 10° C. and 50° C., between 10° C. and 30° C., or between 20° C. and 30° C. In some variations, the compound of formula (A) is combined with the nitroalkane of formula (I) to produce the furan of formula (B) at a pressure of between 1 atma to 2 atma.

Thus, in certain aspects, provided herein are methods of producing a compound of formula (B) by:
combining a compound of formula (A) with a nitroalkane of formula (I), to produce a furan of formula (B).

In some variations, the furan of formula (A) is:

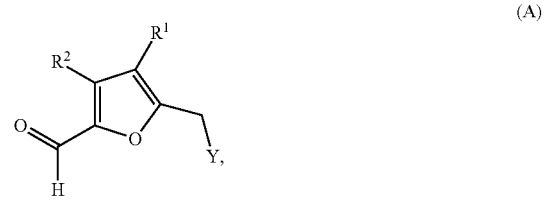

wherein:
Y is halo; and
$R^1$ and $R^2$ are independently H or alkyl.

In some variations, Y is chloro. In other variations, Y is bromo, iodo, or fluoro.

In some variations, the nitroalkane compound of formula (I) is:

$$(R^xCH_2)NO_2 \tag{I},$$

wherein $R^x$ is H or alkyl.

It should be understood that when the compound of formula (I) is used to produce the furan of formula (B), $R^x$ in formulae (I) and (B) are the same. It should further be understood that when the compound of formula (A) is used to produce the furan of formula (B), $R^1$ and $R^2$ in formulae (A) and (B) are the same.

In some variations, combining a compound of formula (A) and a nitroalkane of formula (I) produces a compound of formula (B); compound of formula (AB) as described above; a compound of formula (Q); or a compound of formula (R); or any combinations thereof. The compounds of formulae (Q) and (R) are described in further detail below.

Compounds of Formula (B-I)

In other aspects, provided herein are dinitro furan compounds of formula (B-I):

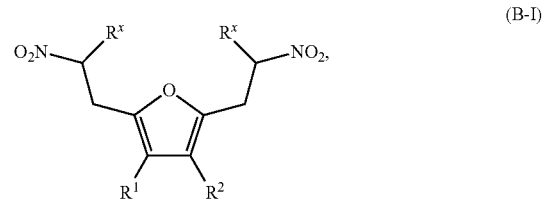

wherein:
$R^x$ is H or alkyl; and
$R^1$ and $R^2$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

For example, in certain embodiments, $R^1$ and $R^2$ are H, and the compound of formula (B-I) is:

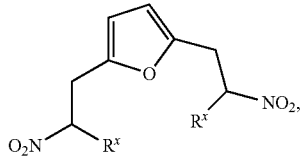

wherein $R^x$ is H or alkyl.

In other embodiments, $R^x$, $R^1$ and $R^2$ are all H, and the compound of formula (B-I) is:

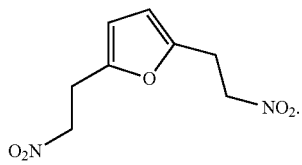

In yet other embodiments, $R^x$ is methyl, $R^1$ and $R^2$ are both H, and the compound of formula (B-I) is:

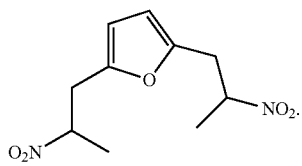 [SMILES: CC(Cc1ccc(CC(C)[N+](=O)[O-])o1)[N+](=O)[O-]]

Methods of Producing Compounds of Formula (B-I)

In certain aspects, provided herein are also methods of producing dinitro furans, including, for example, the compounds of formula (B-I). With reference again to FIG. 1, process 100 depicts an exemplary pathway to produce an example of a furan of formula (B-I), wherein $R^1$ and $R^2$ are H. In process 100, an example of a dinitro vinyl furan of formula (B) is reduced in step 102 to produce an example of a furan of formula (B-I), wherein $R^1$ and $R^2$ are H, and the furan of formula (B) is as described above. It should be understood that while process 100 depicts examples of compounds of formulae (B) and (B-I) in which $R^1$ and $R^2$ are both H, in some variations of process 100, at least one of $R^1$ and $R^2$ is alkyl. In other variations, both $R^1$ and $R^2$ are alkyl.

Variations of the methods of producing dinitro furans, including, for example, the compounds of formula (B-I), are exemplified in General Reaction Scheme B-I described below.

General Reaction Scheme B-I

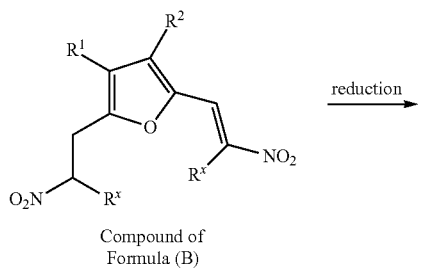

Compound of Formula (B)

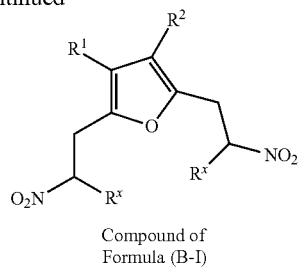

Compound of Formula (B-I)

General Reaction Scheme B-I depicts an exemplary reaction to produce a furan of formula (B-I), wherein $R^1$ and $R^2$ are independently H or alkyl, and $R^x$ is H or alkyl, by reducing a compound of formula (B), wherein $R^1$ and $R^2$ are independently H or alkyl, and $R^x$ is H or alkyl, as is described above.

In some variations of the reaction depicted in General Reaction Scheme B-I, the compound of formula (B) is reduced in the presence of hydrogen to produce the furan of formula (B-I). The hydrogen may be provided in the form of hydrogen gas or by transfer hydrogenation (e.g., by addition of cyclohexene or cyclohexadiene to the reaction mixture as the hydrogen source).

In one variation, the compound of formula (B) is reduced at a pressure of at least 1 psi, or at least 10 psi; or between 1 psi and 1500 psi, between 1 psi and 1000 psi, between 500 psi and 1500 psi, between 1 psi and 50 psi, between 1 psi and 100 psi, between 1 psi and 80 psi, between 1 psi and 75 psi, or between 30 psi and 60 psi to produce the compound of formula (B-I). It should be understood that the hydrogen gas may be dissolved, or at least partially dissolved, in the reagents and/or other solvents described herein.

In some variations, the furan of formula (B) is reduced in the presence of hydrogen and catalyst to produce the furan of formula (B-I). Any suitable catalyst may be used.

In certain variations, the catalyst includes a metal. In certain variations, the catalyst includes palladium, platinum, rhodium, rhenium, or a combination thereof. In one variation, the catalyst includes palladium, platinum, or a combination thereof. For example, the catalyst may be palladium on carbon (Pd/C) or platinum on carbon (Pt/C). In another variation, the catalyst includes rhodium, rhenium, or a combination thereof. For example, the catalyst may be Rh—Re/SiO$_2$.

In some variations, the catalyst further includes a solid support. In certain variation, the catalyst includes a solid acid support. For example, in one variation, the catalyst may include fluorosulfonic acid polymer on amorphous silica (e.g., Nafion® SAC-13).

In some variations, the compound of formula (B) is reduced to produce the furan of formula (B-I) at a temperature between 0° C. to 100° C. In certain variations, the compound of formula (B) is reduced to produce the furan of formula (B-I) at a temperature between 10° C. to 60° C., or between 10° C. to 50° C.

Thus, in certain aspects, provided herein are methods of producing a compound of formula (B-I) by:

reducing a compound of formula (B) to produce a furan of formula (B-I).

It should be understood that when the compound of formula (B) is used to produce the furan of formula (B-I), $R^1$, $R^2$, and $R^x$ in formulae (B) and (B-I) are the same.

Compounds of Formula (B-IIa)

In other aspects, provided herein are (furan)dialkanamine compounds of formula (B-IIa):

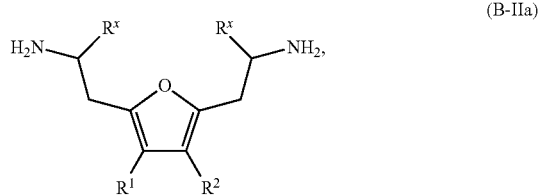

(B-IIa)

wherein:

$R^x$ is H or alkyl; and $R^1$ and $R^2$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

For example, in certain embodiments, $R^1$ and $R^2$ are H, and the compound of formula (B-IIa) is:

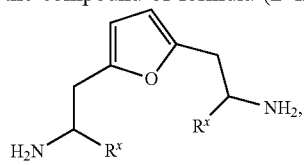

wherein $R^x$ is H or alkyl.

In other embodiments, $R^x$, $R^1$ and $R^2$ are all H, and the compound of formula (B-IIa) is:

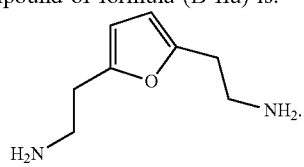

In yet other embodiments, $R^x$ is methyl, $R^1$ and $R^2$ are both H, and the compound of formula (B-IIa) is:

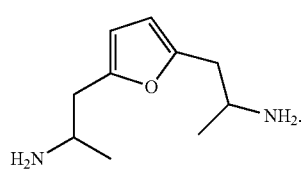

Compounds of Formula (B-IIb)

In yet other aspects, provided herein are (tetrahydrofuran)dialkanamine compounds of formula (B-IIb):

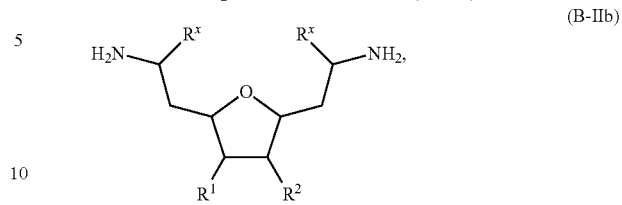

(B-IIb)

wherein:

$R^x$ is H or alkyl; and $R^1$ and $R^2$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

For example, in certain embodiments, $R^1$ and $R^2$ are H, and the compound of formula (B-IIb) is:

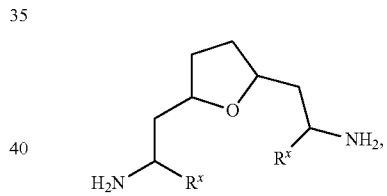

wherein $R^x$ is H or alkyl.

In other embodiments, $R^x$, $R^1$ and $R^2$ are all H, and the compound of formula (B-IIb) is:

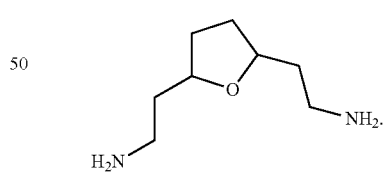

In yet other embodiments, $R^x$ is methyl, $R^1$ and $R^2$ are both H, and the compound of formula (B-IIb) is:

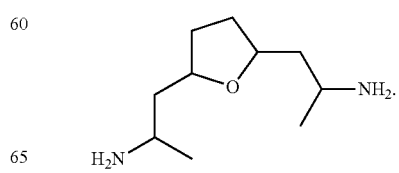

Methods of Producing Compounds of Formula (B-IIa) and Formula (B-IIb)

In certain aspects, provided herein are also methods of producing (furan)dialkanamines, including, for example, the compounds of formula (B-IIa). With reference again to FIG. 1, process 110 depicts an exemplary pathway to produce an example of a furan of formula (B-IIa), wherein $R^1$ and $R^2$ are H. An example of a dinitro vinyl furan of formula (B) is reduced in step 112 to produce an example of a of a furan of formula (B-IIa), wherein the example of a furan of formula (B) is as described above. Thus, in one aspect, provided is a method that includes: reducing a furan of formula (B) to produce a furan of formula (B-IIa).

With reference again to process 110 (FIG. 1), the reduction of furans of formula (B) may also produce tetrahydrofurans of formula (B-IIb), either alone or in combination with the furan of formula (B-IIa), as discussed above. Thus, in another aspect, provided is a method that includes: reducing a furan of formula (B) to produce a tetrahydrofuran of formula (B-IIb).

It should be understood that while process 110 depicts examples of compounds of formulae (B), (B-IIa), and (B-IIb) in which $R^1$ and $R^2$ are both H, in some variations of process 110, at least one of $R^1$ and $R^2$ is alkyl. In certain variations, both $R^1$ and $R^2$ are alkyl.

It should be understood that when the compound of formula (B) is used to produce furans of formula (B-IIa) or tetrahydrofurans of formula (B-IIb), or a combination thereof, $R^1$, $R^2$, and $R^x$ in formulae (B), (B-IIa), and (B-IIb) are the same.

In some variations of the compounds of formulae (B) and (B-IIa), $R^1$, $R^2$, and $R^x$ are H. Thus, in some variations:
the furan of formula (B) is:

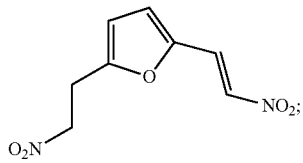 [SMILES: O=[N+]([O-])/C=C/c1ccc(CC[N+](=O)[O-])o1]

and
the furan of formula (B-IIa) is:

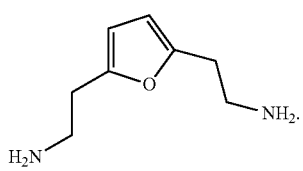

In some variations of the compounds of formulae (B) and (B-IIb), $R^1$, $R^2$, and $R^x$ are H. Thus, in some variations:
the furan of formula (B) is:

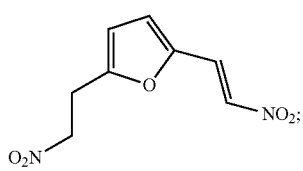

and
the tetrahydrofuran of formula (B-IIb) is:

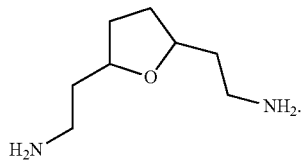 [SMILES: NCCC1CCC(CCN)O1]

In other variations of the compounds of formulae (B), (B-IIa) and (B-IIb), $R^x$ is alkyl. In certain variations of the compounds of formulae (B), (B-IIa) and (B-IIb), $R^x$ is $C_{1-20}$ alkyl, or $C_{1-10}$ alkyl, or $C_{1-5}$ alkyl. In certain variations, $R^x$ is methyl, ethyl, propyl or butyl.

Variations of the methods of producing furan(alkadiamines), including, for example, the compounds of formula (B-IIa); and tetrahydrofuran(alkadiamines), including, for example, the compounds of formula (B-IIb), are exemplified in General Reaction Scheme B-II described below.

General Reaction Scheme B-II

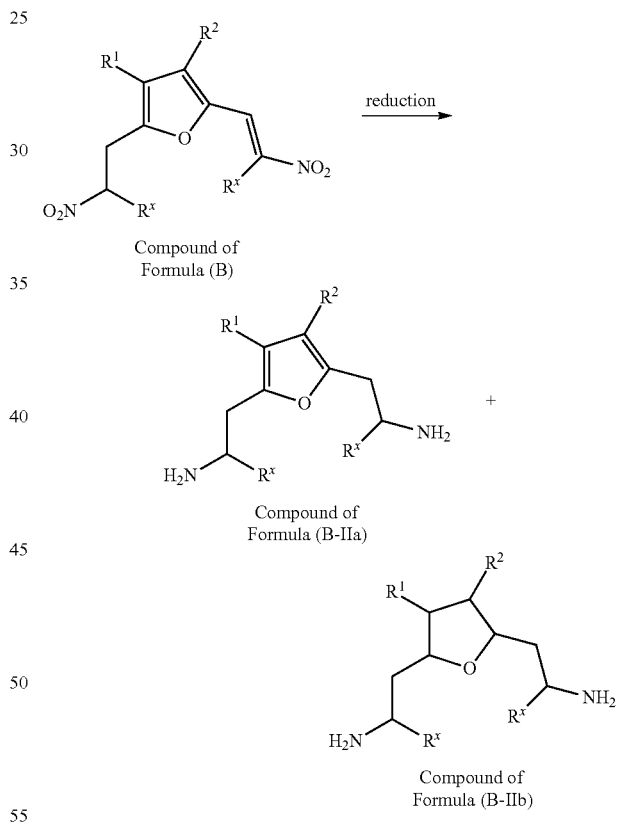

General Reaction Scheme B-II depicts an exemplary reaction to produce a furan of formula (B-IIa), wherein $R^1$ and $R^2$ are independently H or alkyl, and $R^x$ is H or alkyl; and a tetrahydrofuran of formula (B-IIb), wherein $R^1$ and $R^2$ are independently H or alkyl, and $R^x$ is H or alkyl; by reducing a compound of formula (B), wherein $R^1$ and $R^2$ are independently H or alkyl, and $R^x$ is H or alkyl, as is described above. It should be understood that while General Reaction Scheme B-II depicts the production of a furan of formula (B-IIa) and a tetrahydrofuran of formula (B-IIb), in some variations only a furan of formula (B-IIa) is produced.

In other variations, only a tetrahydrofuran of formula (B-IIb) is produced. In still other variations, a mixture of a furan of formula (B-IIa) and a tetrahydrofuran of formula (B-IIb) is produced.

In some variations of the reaction depicted in General Reaction Scheme B-II, the compound of formula (B) is reduced in the presence of hydrogen to produce the furan of formula (B-IIa) or tetrahydrofuran of formula (B-IIb), or combination thereof. The hydrogen may be provided in the form of hydrogen gas or by transfer hydrogenation (e.g., by addition of cyclohexene or cyclohexadiene to the reaction mixture as the hydrogen source).

In one variation, the compound of formula (B) is reduced at a pressure of at least 1 psi, or at least 10 psi; or between 1 psi and 1500 psi, between 1 psi and 1000 psi, between 500 psi and 1500 psi, between 1 psi and 50 psi, between 1 psi and 100 psi, between 1 psi and 80 psi, between 1 psi and 75 psi, or between 30 psi and 60 psi to produce the compound of formula (B-IIa), the compound of formula (B-IIb), or a combination thereof. It should be understood that the hydrogen gas may be dissolved, or at least partially dissolved, in the reagents and/or other solvents described herein.

In some variations, the furan of formula (B) is reduced in the presence of hydrogen and catalyst to produce the compound of formula (B-IIa) or (B-IIb). Any suitable catalyst may be used.

In certain variations, the catalyst includes a metal. In certain variations, the catalyst includes palladium, platinum, rhodium, rhenium, or a combination thereof. In one variation, the catalyst includes palladium, platinum, or a combination thereof. For example, the catalyst may be palladium on carbon (Pd/C) or platinum on carbon (Pt/C). In another variation, the catalyst includes rhodium, rhenium, or a combination thereof. For example, the catalyst may be Rh—Re/SiO$_2$.

In some variations, the catalyst further includes a solid support. In certain variation, the catalyst includes a solid acid support. For example, in one variation, the catalyst may include fluorosulfonic acid polymer on amorphous silica (e.g., Nafion® SAC-13).

In some variations, the compound of formula (B) is reduced to produce the compound of formula (B-IIa) or (B-IIb) at a temperature between 0° C. to 100° C. In certain variations, the compound of formula (B) is reduced to produce the compound of formula (B-IIa) or (B-IIb) at a temperature between 10° C. to 60° C., or between 10° C. to 50° C.

Thus, in certain aspects, provided herein are methods of producing a compound of formula (B-IIa), a compound of formula (B-IIb), or a combination thereof by:
reducing a compound of formula (B) to produce a furan of formula (B-IIa), a tetrahydrofuran of formula (B-IIb), or a combination thereof.

Compounds of Formula (B-III)

In other aspects, provided herein are alkyldiamine compounds of formula (B-III):

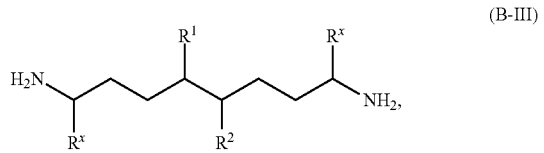

(B-III)

wherein:
R$^x$ is H or alkyl; and
R$^1$ and R$^2$ are independently H or alkyl.

In some variations, R$^x$ is H. In other variations, R$^x$ is alkyl. In certain variations, R$^x$ is C$_{1-20}$ alkyl, or C$_{1-10}$ alkyl, or C$_{1-5}$ alkyl. In some variations, R$^x$ is methyl, ethyl, propyl or butyl.

In some variations, R$^1$ and R$^2$ are both H. In other variations, at least one of R$^1$ and R$^2$ is alkyl. For example, in some variations, R$^1$ is H and R$^2$ is alkyl. In other variations R$^1$ is alkyl and R$^2$ is H. In yet other variations, both R$^1$ and R$^2$ are independently alkyl. In certain variations, R$^1$ and R$^2$ are independently H or C$_{1-20}$ alkyl, C$_{1-10}$ alkyl, or C$_{1-5}$ alkyl. In other variations, R$^1$ and R$^2$ are independently H or methyl, ethyl, propyl or butyl.

It should be generally understood that any of the variations for the R$^x$, R$^1$, and R$^2$ described herein may be combined the same as if each and every combination for the variables were specifically and individually listed.

In some variations, R$^1$ and R$^2$ are H, and the alkyldiamine of formula (B-III) is:

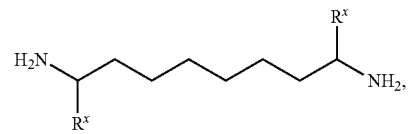

wherein R$^x$ is H or alkyl.

In other embodiments, R$^x$, R$^1$ and R$^2$ are all H, and the compound of formula (B-III) is:

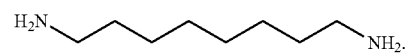

In yet other embodiments, R$^x$ is methyl, R$^1$ and R$^2$ are both H, and the compound of formula (B-III) is:

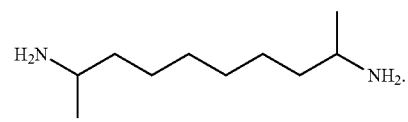

Methods of Producing Compounds of Formula (B-III)

In certain aspects, provided herein are also methods of producing alkyldiamines, including, for example, the compounds of formula (B-III). With reference again to FIG. 1, process 120 depicts an exemplary process to produce alkyldiamines from the reduction of an example of a compound of formula (B). In process 120, an example of a dinitro vinyl furan of formula (B) is reduced to produce an alkyldiamine of formula (B-III), wherein the furan of formula (B) is as described above. Thus, in one aspect, provided is a method that includes: reducing a furan of formula (B) to produce alkyldiamines of formula (B-III). It should be understood that while process 120 depicts compounds of formulae (B) and (B-III) in which R$^1$ and R$^2$ are both H, in some variations of process 120, at least one of R$^1$ and R$^2$ are alkyl. In other variations, both R$^1$ and R$^2$ are alkyl.

Variations of the methods of producing alkyldiamines, including, for example, the compounds of formula (B-III), are exemplified in General Reaction Scheme B-III described below.

General Reaction Scheme B-III

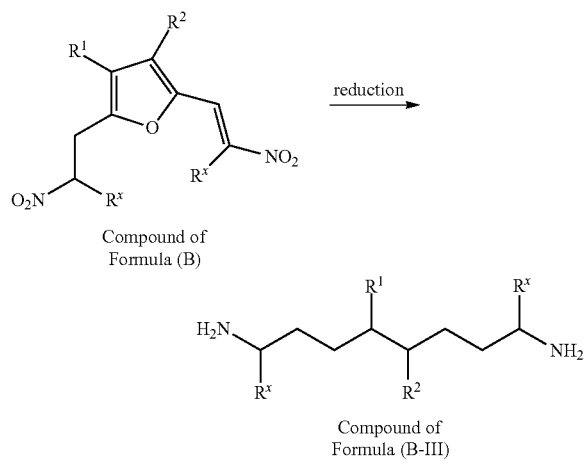

Compound of Formula (B)

Compound of Formula (B-III)

General Reaction Scheme B-III depicts an exemplary reaction to produce a compound of formula (B-III), wherein $R^1$ and $R^2$ are independently H or alkyl, and $R^x$ is H or alkyl, by reducing a compound of formula (B), wherein $R^1$ and $R^2$ are independently H or alkyl, and $R^x$ is H or alkyl, as is described above.

In some variations of the reaction depicted in General Reaction Scheme B-III, the compound of formula (B) is reduced in the presence of hydrogen to produce the compound of formula (B-III). The hydrogen may be provided in the form of hydrogen gas or by transfer hydrogenation (e.g., by addition of cyclohexene or cyclohexadiene to the reaction mixture as the hydrogen source).

In one variation, the compound of formula (B) is reduced at a pressure of at least 1 psi, or at least 10 psi; or between 1 psi and 1500 psi, between 1 psi and 1000 psi, between 500 psi and 1500 psi, between 1 psi and 50 psi, between 1 psi and 100 psi, between 1 psi and 80 psi, between 1 psi and 75 psi, or between 30 psi and 60 psi to produce the compound of formula (B-I). It should be understood that the hydrogen gas may be dissolved, or at least partially dissolved, in the reagents and/or other solvents described herein.

In some variations, the furan of formula (B) is reduced in the presence of hydrogen and catalyst to produce the compound of formula (B-III). Any suitable catalyst may be used.

In certain variations, the catalyst includes a metal. In certain variations, the catalyst includes palladium, platinum, rhodium, rhenium, or a combination thereof. In one variation, the catalyst includes palladium, platinum, or a combination thereof. For example, the catalyst may be palladium on carbon (Pd/C) or platinum on carbon (Pt/C). In another variation, the catalyst includes rhodium, rhenium, or a combination thereof. For example, the catalyst may be Rh—Re/SiO$_2$.

In some variations, the catalyst further includes a solid support. In certain variation, the catalyst includes a solid acid support. For example, in one variation, the catalyst may include fluorosulfonic acid polymer on amorphous silica (e.g., Nafion® SAC-13).

In some variations, the compound of formula (B) is reduced to produce the compound of formula (B-III) at a temperature between 0° C. to 100° C. In certain variations, the compound of formula (B) is reduced to produce the compound of formula (B-III) at a temperature between 10° C. to 60° C., or between 10° C. to 50° C.

Thus, in certain aspects, provided herein are methods of producing a compound of formula (B-III) by:
reducing a compound of formula (B) to produce a compound of formula (B-III).

It should be understood that when the compound of formula (B) is used to produce an alkyldiamine of formula (B-III), $R^1$, $R^2$, and $R^x$ in formulae (B) and (B-III) are the same.

In some variations of the compounds of formulae (B) and (B-III), $R^1$ and $R^2$ are H, and $R^x$ is H. Thus, in some variations:
the furan of formula (B) is:

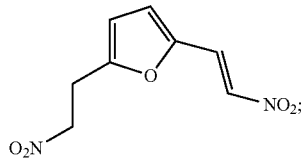 [SMILES: O=[N+]([O-])/C=C/c1ccc(CC[N+](=O)[O-])o1]

and
the alkyldiamine of formula (B-III) is:

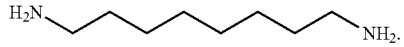

In other variations of the compounds of formulae (B) and (B-III), $R^x$ is alkyl. In certain variations of the compounds of formulae (B) and (B-III), $R^x$ is $C_{1-20}$ alkyl, or $C_{1-10}$ alkyl, or $C_{1-5}$ alkyl. In certain variations, $R^x$ is methyl, ethyl, propyl or butyl.

In some aspects, provided herein are methods of producing a furan of formula (B-I), a furan of formula (B-IIa), a tetrahydrofuran of formula (B-IIb), an alkyldiamine of formula (B-M), or any mixtures thereof, by:
reducing a furan of formula (B) to produce a furan of formula (B-I), a furan of formula (B-IIa), a tetrahydrofuran of formula (B-IIb), an alkyldiamine of formula (B-III), or any mixtures thereof.

Compounds of Formula (C)

In other aspects, provided herein are (phenylene)dinitro compounds of formula (C):

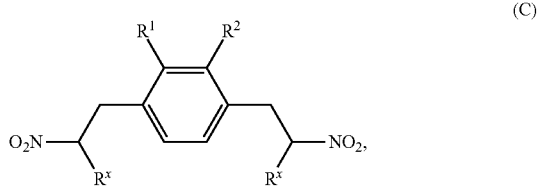

wherein:
$R^x$ is H or alkyl; and
$R^1$ and $R^2$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

For example, in certain embodiments, $R^1$ and $R^2$ are H, and the compound of formula (C) is:

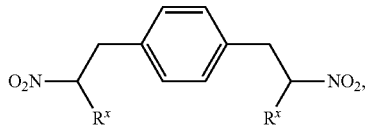

wherein $R^x$ is H or alkyl.

In other embodiments, $R^x$, $R^1$ and $R^2$ are all H, and the compound of formula (C) is:

In yet other embodiments, $R^x$ is methyl, $R^1$ and $R^2$ are both H, and the compound of formula (C) is:

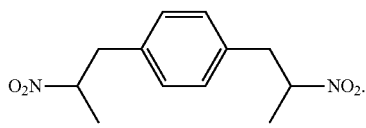

Methods of Producing Compounds of Formula (C)

In certain aspects, provided herein are also methods of producing (phenylene)dinitro compounds, including, for example, the compounds of formula (C). With reference to FIG. 1, process 100 depicts an exemplary pathway to produce an example of a compound of formula (C). In process 100, an example of a dinitro furan of formula (B-I) undergoes a Diels-Alder reaction with ethylene in step 104 to produce an example of a compound of formula (C), wherein the furan of formula (B-I) is as described above. It should be understood that while process 100 depicts examples of compounds of formulae (B-I) and (C) in which $R^1$ and $R^2$ are both H, in some variations of process 100, at least one of $R^1$ and $R^2$ are alkyl. In other variations, both $R^1$ and $R^2$ are alkyl.

Variations of the methods of producing (phenylene)dinitro compounds, including, for example, the compounds of formula (C), are exemplified in General Reaction Scheme C described below.

General Reaction Scheme C

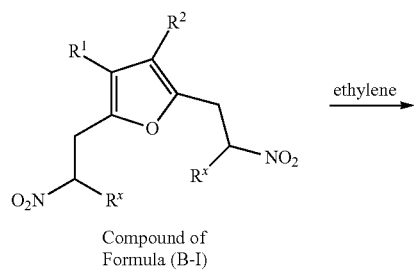

Compound of Formula (B-I)

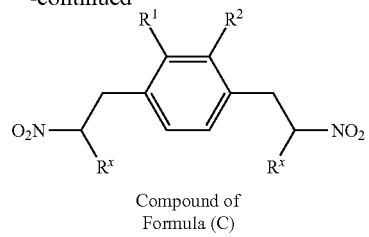

Compound of Formula (C)

General Reaction Scheme C depicts an exemplary reaction to convert a compound of formula (B-I), wherein $R^1$ and $R^2$ are independently H or alkyl, and $R^x$ is H or alkyl, to a compound of formula (C), wherein $R^1$ and $R^2$ are independently H or alkyl, and $R^x$ is H or alkyl, by Diels-Alder reaction with ethylene.

In some variations of the reaction depicted in General Reaction Scheme C, the compound of formula (B-I) is reacted with ethylene at an initial ethylene pressure between 800 to 1500 psia. In certain variations, the initial ethylene pressure is between 800 to 1400 psia. In one variation the initial ethylene pressure is 1000 psia. In some variations, the compound of formula (B-I) is reacted with ethylene at an initial ethylene pressure between 800 to 1500 psi. In certain variations, the initial ethylene pressure is between 800 to 1400 psi. In one variation the initial ethylene pressure is 1000 psi. In some variations, the compound of formula (B-I) is reacted with ethylene in the additional presence of solvent. In certain embodiments, the ethylene may be dissolved, or at least partially dissolved, in one or more solvents. In other variations, the compound of formula (B-I) is reacted with ethylene to produce the compound of formula (C), wherein the ethylene may also be provided at supercritical pressures and/or supercritical temperatures.

In some variations of the reaction depicted in General Reaction Scheme C, the compound of formula (B-I) is reacted with ethylene in the presence of a catalyst to produce the compound of formula (C). Any suitable catalyst may be used. For example, the catalysts may be selected from one or more classes of catalysts, including (i) metal-containing catalysts, including metal-containing salts that are catalytic or may convert in situ into a catalytic species, and (ii) acids (e.g., Lewis acids, weak acids, sulfonic acids, and heteropolyacids). In some embodiments, the catalyst is a metal triflate. In one embodiment, the catalyst is triflic acid.

In some variations, the compound of formula (B-I) is converted to a compound of formula (C) by Diels-Alder reaction with ethylene at a temperature between 200° C. to 400° C. In certain variations, the compound of formula (B-I) is converted to a compound of formula (C) by Diels-Alder reaction with ethylene at a temperature between 250° C. to 350° C. In one variation, the temperature is 350° C.

Thus, in certain aspects, provided herein are methods of producing a compound of formula (C) by:

combining the furan of formula (B-I) with ethylene to produce a compound of formula (C).

It should be understood that when the compound of formula (B-I) is used to produce the compound of formula (C), $R^1$, $R^2$, and $R^x$ in formulae (B-I) and (C) are the same.

Compounds of Formula (C-I)

In other aspects, provided herein are (phenylene)dialkanamine compounds of formula (C-I):

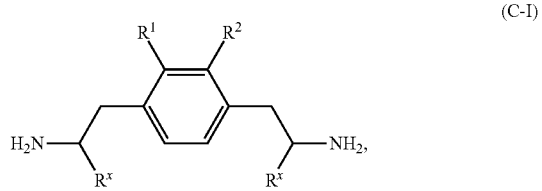

(C-I)

wherein:
$R^x$ is H or alkyl; and
$R^1$ and $R^2$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

For example, in certain embodiments, $R^1$ and $R^2$ are H, and the compound of formula (C-I) is:

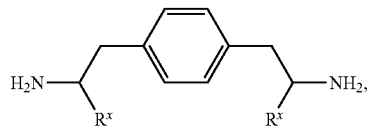

wherein $R^x$ is H or alkyl.

In other embodiments, $R^x$, $R^1$ and $R^2$ are all H, and the compound of formula (C-I) is:

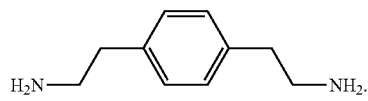

In yet other embodiments, $R^x$ is methyl, $R^1$ and $R^2$ are both H, and the compound of formula (C-I) is:

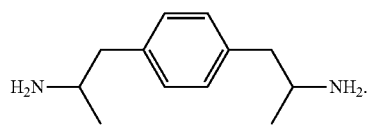

Methods of Producing Compounds of Formula (C-I)

In certain aspects, provided herein are also methods of producing (phenylene)dialkanamine compounds, including, for example, the compounds of formula (C-I).

For example, process 100 (FIG. 1) depicts one pathway to produce examples of (phenylene)dialkanamines of formula (C-I) from examples of furans of formula (C) in step 106.

With reference again to FIG. 1, process 110 depicts another pathway to produce examples of (phenylene)dialkanamines of formula (C-I) from examples of furans of formula (B-IIa) in step 114.

Variations of the methods of producing (phenylene)dialkanamine compounds, including, for example, the compounds of formula (C-I), are exemplified in General Reaction Scheme C-I described below.

General Reaction Scheme C-I

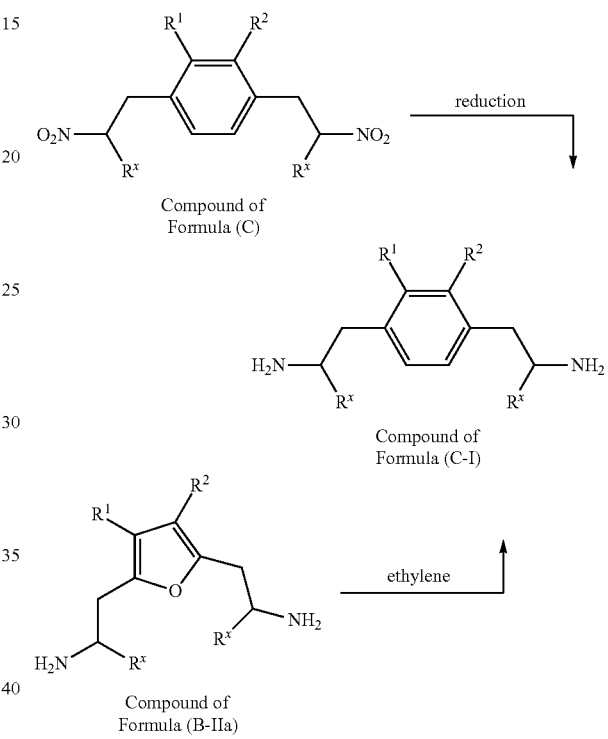

Depicted in General Reaction Scheme C-I are two exemplary reactions to produce a compound of formula (C-I). In one exemplary reaction, a compound of formula (C), wherein $R^1$ and $R^2$ are independently H or alkyl, and $R^x$ is H or alkyl, is reduced to produce a compound of formula (C-I), wherein $R^1$ and $R^2$ are independently H or alkyl, and $R^x$ is H or alkyl. In another exemplary reaction, a compound of formula (B-IIa), wherein $R^1$ and $R^2$ are independently H or alkyl, and $R^x$ is H or alkyl, is converted to a compound of formula (C-I) by Diels-Alder reaction with ethylene.

In some variations of the reaction depicted in General Reaction Scheme C-I, the compound of formula (C) is reduced in the presence of hydrogen to produce the compound of formula (C-I). The hydrogen may be provided in the form of hydrogen gas or by transfer hydrogenation (e.g., by addition of cyclohexene or cyclohexadiene to the reaction mixture as the hydrogen source).

In one variation, the compound of formula (C) is reduced at a pressure of at least 1 psi, or at least 10 psi; or between 1 psi and 1500 psi, between 1 psi and 1000 psi, between 500 psi and 1500 psi, between 1 psi and 50 psi, between 1 psi and 100 psi, between 1 psi and 80 psi, between 1 psi and 75 psi, or between 30 psi and 60 psi to produce the compound of formula (B-I). It should be understood that the hydrogen gas may be dissolved, or at least partially dissolved, in the reagents and/or other solvents described herein.

In some variations, the furan of formula (C) is reduced in the presence of hydrogen and catalyst to produce the compound of formula (C-I). Any suitable catalyst may be used.

In certain variations, the catalyst includes a metal. In certain variations, the catalyst includes palladium, platinum, rhodium, rhenium, or a combination thereof. In one variation, the catalyst includes palladium, platinum, or a combination thereof. For example, the catalyst may be palladium on carbon (Pd/C) or platinum on carbon (Pt/C). In another variation, the catalyst includes rhodium, rhenium, or a combination thereof. For example, the catalyst may be Rh—Re/SiO$_2$.

In some variations, the catalyst further includes a solid support. In certain variation, the catalyst includes a solid acid support. For example, in one variation, the catalyst may include fluorosulfonic acid polymer on amorphous silica (e.g., Nafion® SAC-13).

In some variations, the compound of formula (C) is reduced to produce the compound of formula (C-I) at a temperature between 0° C. to 100° C. In certain variations, the compound of formula (C) is reduced to produce the compound of formula (C-I) at a temperature between 10° C. to 60° C., or between 10° C. to 50° C.

Thus, in one aspect, provided is a method that includes:
  reducing a compound of formula (C) to produce a (phenylene)dialkanamine of formula (C-I).

In some variations of the reaction depicted in General Reaction Scheme C-I, the compound of formula (B-IIa) is converted to a compound of formula (C-I) by Diels-Alder reaction with ethylene. In some variations, the compound of formula (B-IIa) is reacted with ethylene at an initial ethylene pressure between 800 psia to 1500 psia. In certain variations, the initial ethylene pressure is 1000 psia. In some variations, the compound of formula (B-IIa) is reacted with ethylene at an initial ethylene pressure between 800 psi to 1500 psi. In certain variations, the initial ethylene pressure is 1000 psi. In some variations, the compound of formula (B-IIa) is reacted with ethylene in the additional presence of solvent. In certain embodiments, the ethylene may be dissolved, or at least partially dissolved, in one or more solvents. In other variations, the compound of formula (B-IIa) is reacted with ethylene to produce the compound of formula (C-I), wherein the ethylene may also be provided at supercritical pressures and/or supercritical temperatures.

In some variations of the reaction depicted in General Reaction Scheme C-I, the compound of formula (B-IIa) is reacted with ethylene in the presence of a catalyst to produce the compound of formula (C-I). Any suitable catalyst may be used. For example, the catalyst or catalysts may be selected from one or more classes of catalysts, including (i) metal-containing catalysts, including metal-containing salts that are catalytic or may convert in situ into a catalytic species, and (ii) acids (e.g., Lewis acids, weak acids, sulfonic acids, and heteropolyacids). In some embodiments, the catalyst is a metal triflate. In one embodiment, the catalyst is triflic acid.

In some variations, the compound of formula (B-IIa) is converted to a compound of formula (C-I) by Diels-Alder reaction with ethylene at a temperature between 200° C. to 400° C. In certain variations, the compound of formula (B-IIa) is converted to a compound of formula (C-I) by Diels-Alder reaction with ethylene at a temperature between 250° C. to 350° C. In one variation, the temperature is 300° C.

Thus, in another aspect, provided is a method that includes:
  combining a furan of formula (B-IIa) with ethylene to produce a compound of formula (C-I).

It should be understood that when the compound of formula (B-IIa) is used to produce the compound of formula (C-I), $R^1$, $R^2$, and $R^x$ in formulae (B-IIa) and (C-I) are the same.

As previously discussed, a compound of formula (B) may be converted to a compound of formula (B-IIa); and a compound of formula (B) may be converted to a compound of formula (B-I), which may be converted to a compound of formula (C). Thus, in some aspects, provided herein are methods of producing a compound of formula (C-I) from a compound of formula (B).

For example, process 100 depicts one pathway to produce examples of (phenylene)dialkanamines of formula (C-I) from examples of furans of formula (B). Thus, in one aspect, provided is a method that includes:
  reducing a furan of formula (B) to produce a furan of formula (B-I) in step 102;
  combining the furan of formula (B-I) with ethylene to produce a compound of formula (C) in step 104; and
  reducing the compound of formula (C) in step 106 to produce the (phenylene)dialkanamines of formula (C-I).

In some variations, $R^1$ and $R^2$ are both H. Thus, in some variations, the furan of formula (B) is:

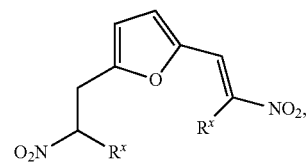

(B)

wherein $R^x$ is H or alkyl.
In some variations, the furan of formula (B-I) is:

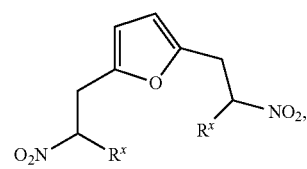

(B-I)

wherein $R^x$ is H or alkyl.
In some variations, the compound of formula (C) is:

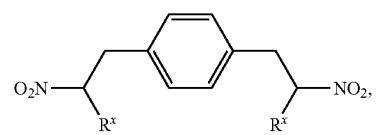

(C)

wherein $R^x$ is H or alkyl.

It should be understood that when the compound of formulae (B), (B-I) and (C) are used to produce (phenylene)dialkanamines of formula (C-I), $R^1$, $R^2$, and $R^x$ in formulae (B), (B-I), (C) and (C-I) are the same.

In some variations of the compounds of formulae (B), (B-I), (C) and (C-I), $R^1$ and $R^2$ are each H, and $R^x$ is H. Thus, in some variations:

the furan of formula (B) is:

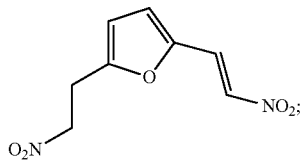

the furan of formula (B-I) is:

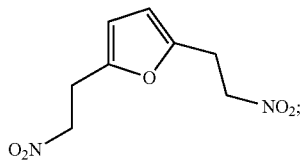 [SMILES: O=[N+]([O-])CCc1ccc(CC[N+](=O)[O-])o1]

the compound of formula (C) is:

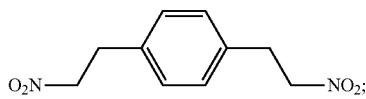

and
the compound of formula (C-I) is:

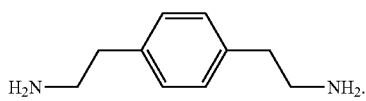

In other variations of the compounds of formulae (B), (B-I), (C) and (C-I), $R^x$ is alkyl. In certain variations of the compounds of formulae (B), (B-I), (C) and (C-I), $R^x$ is $C_{1-20}$ alkyl, or $C_{1-10}$ alkyl, or $C_{1-5}$ alkyl. In certain variations, $R^x$ is methyl, ethyl, propyl or butyl.

With reference again to FIG. 1, process 110 depicts another pathway to produce examples of (phenylene)dialkanamines of formula (C-I) from examples of furans of formula (B). Thus, in another aspect, provided is a method that includes:

reducing a furan of formula (B) to produce a furan of formula (B-IIa) in step 112; and combining the furan of formula (B-IIa) and ethylene to produce a compound of formula (C-I) in step 114.

In some variations, $R^1$ and $R^2$ are H. Thus, in some variations, the furan of formula (B-IIa) is:

(B-IIa)

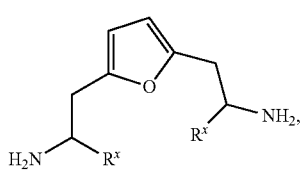

wherein $R^x$ is H or alkyl.

It should be understood that when the compound of formulae (B) and (B-IIa) are used to produce (phenylene) dialkanamines of formula (C-I), $R^1$, $R^2$, and $R^x$ in formulae (B), (B-IIa), and (C-I) are the same.

In some variations of the compounds of formulae (B), (B-IIa), and (C-I), $R^1$ and $R^2$ are each H, and $R^x$ is H. Thus, in some variations:

the furan of formula (B) is:

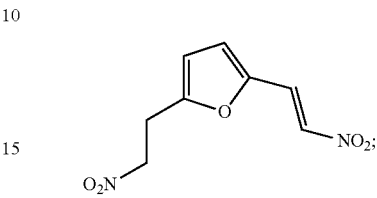

the furan of formula (B-IIa) is:

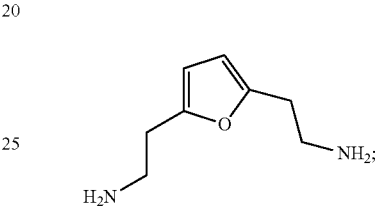

and
the compound of formula (C-I) is:

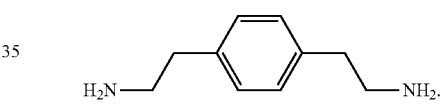

In other variations of the compounds of formulae (B), (B-IIa), and (C-I), $R^x$ is alkyl. In certain variations of the compounds of formulae (B), (B-IIa), and (C-I), $R^x$ is $C_{1-20}$ alkyl, or $C_{1-10}$ alkyl, or $C_{1-5}$ alkyl. In certain variations, $R^x$ is methyl, ethyl, propyl or butyl.

Compounds of Formula (Q)

In other aspects, provided herein are haloalkyl(furan) nitroethanol compounds. In some variations, the haloalkyl (furan)nitroethanol compounds are compounds of formula (Q):

(Q)

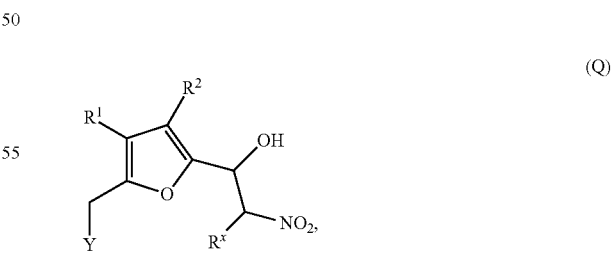

wherein:
Y is halo; and
$R^1$, $R^2$ and $R^x$ are independently H or alkyl.

In some variations, Y is chloro. In other variations, Y is bromo, iodo, or fluoro. For example, in certain variations, Y is chloro, and the compound of formula (Q) is:

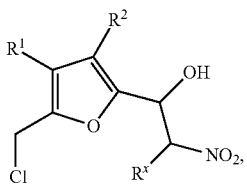

wherein $R^1$, $R^2$, and $R^x$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the Y, $R^x$, $R^1$, and $R^2$ described herein may be combined the same as if each and every combination for the variables were specifically and individually listed.

For example, in certain embodiments, $R^1$ and $R^2$ are H, and the compound of formula (Q) is:

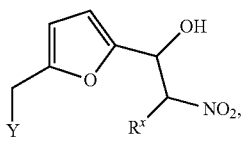

wherein Y is halo, and $R^x$ is H or alkyl.

In other embodiments, $R^x$, $R^1$ and $R^2$ are all H, and the compound of formula (Q) is:

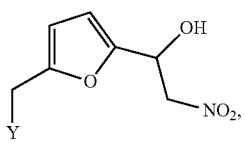

wherein Y is halo.

In yet other embodiments, $R^x$, $R^1$ and $R^2$ are all H, Y is chloro, and the compound of formula (Q) is:

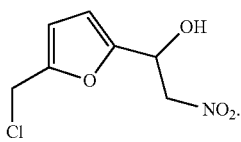 [SMILES: O=[N+]([O-])CC(O)c1ccc(CCl)o1]

Methods of Producing Compounds of Formula (Q)

Figure 4:
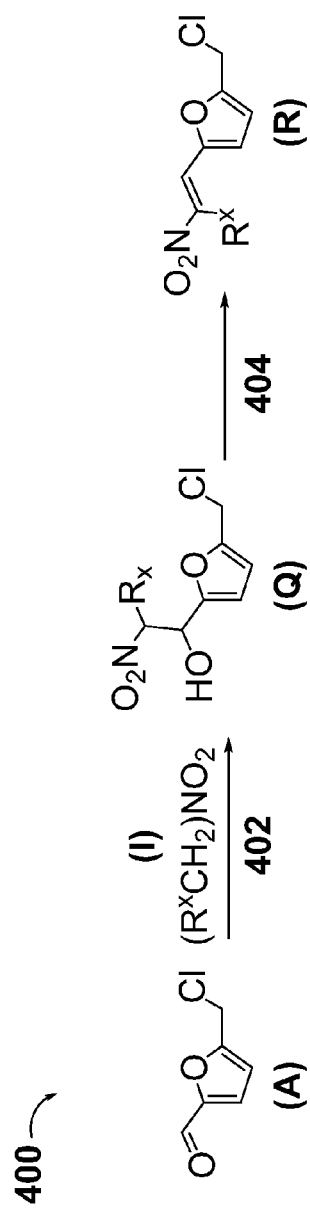
FIG. 4 depicts an exemplary process to produce exemplary chloromethyl(furan)nitroethanol compounds of formula (Q), and exemplary chloromethyl(furan)nitrovinyl compounds of formula (R) from 5-(chloromethyl)furfural.

In certain aspects, provided herein are also methods of producing haloalkyl(furan)nitroethanol compounds, including, for example, the compounds of formula (Q). For example, with reference to FIG. 4, process 400 depicts an exemplary pathway to produce an example of a furan of formula (Q) from 5-(chloromethyl)furfural (one example of a compound of formula (A) wherein $R^1$ and $R^2$ are H, and Y is chloro). In step 402, 5-(chloromethyl)furfural is combined with an example of a nitroalkane of formula (I) to produce an example of a furan of formula (Q), wherein $R^1$ and $R^2$ are H. In some variations of process 400, the furan of formula (A) is combined with a nitroalkane of formula (I) in the presence of a base and optionally solvent to produce the furan of formula (Q). It should be understood that while FIG. 4 depicts the compounds of formulae (A) and (Q) wherein Y is chloro, in other variations Y is bromo, fluoro, or iodo. It should be further understood that while FIG. 4 depicts the compound of formula (Q) wherein $R^1$ and $R^2$ are both H, in other variations at least one of $R^1$ and $R^2$ is alkyl, while in certain other variations $R^1$ and $R^2$ are both alkyl.

Variations of the methods of producing haloalkyl(furan)nitroethanol compounds, including, for example, the compounds of formula (Q), are exemplified in General Reaction Scheme Q described below.

General Reaction Scheme Q

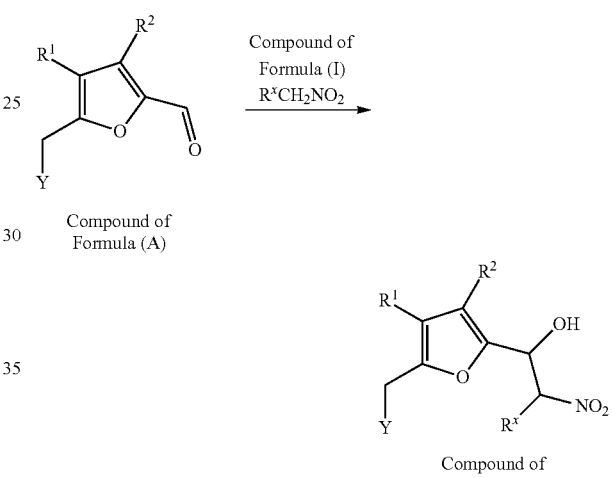

General Reaction Scheme Q depicts an exemplary reaction to produce a furan of formula (Q), wherein $R^1$ and $R^2$ are independently H or alkyl, and $R^x$ is H or alkyl, from a compound of formula (A), wherein $R^1$ and $R^2$ are independently H or alkyl, and Y is halo, and a compound of formula (I), wherein $R^x$ is H or alkyl.

In some variations of the reaction depicted in General Reaction Scheme Q, the compound of formula (A) and the nitroalkane of formula (I) are combined in the presence of a base and optionally a solvent to produce the compound of formula (Q). Any suitable base may be used.

For example, in some variations, the base is a non-nucleophilic base. In certain variations, the base is a non-nucleophilic base that forms a weak acid upon protonation. In certain variations, the base is cesium carbonate ($CsCO_3$) or an amine, such as triethylamine. In other variations, the base is ammonium acetate or alumina. A combination of any of the bases described herein may also be used.

In some variations, the solvent includes an aromatic solvent or an alkyl acetate solvent. In one variation, the solvent is toluene, methyl acetate, ethyl acetate, or propyl acetate. A combination of any of the solvents described herein may also be used.

In some variations, the compound of formula (A) is combined with the nitroalkane of formula (I) to produce the furan of formula (Q) at a temperature between 0° C. and 100° C., between 10° C. and 100° C., between 10° C. and 50° C., between 10° C. and 30° C., or between 20° C. and 30° C. In some variations, the compound of formula (A) is combined with the nitroalkane of formula (I) to produce the furan of formula (Q) at a pressure between 1 atma to 2 atma.

Thus, in certain aspects, provided herein are methods of producing a compound of formula (Q) by:

combining a compound of formula (A) with a nitroalkane of formula (I), to produce a furan of formula (Q).

In some variations, the furan of formula (A) is:

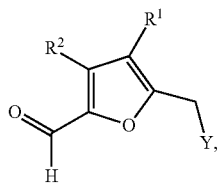

(A)

wherein:
Y is halo; and
$R^1$ and $R^2$ are independently H or alkyl.

In some variations, Y is chloro. In other variations, Y is bromo, iodo, or fluoro.

In some variations, the nitroalkane compound of formula (I) is:

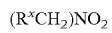

$(R^xCH_2)NO_2$     (I), wherein $R^x$ is H or alkyl.

It should be understood that when the compound of formula (A) is used to produce the furan of formula (Q), $R^1$, $R^2$, and Y in formulae (A) and (Q) are the same. It should be further understood that when a compound of formula (I) is used to produce the furan of formula (Q), IV in formula (I) and formula (Q) are the same. In some variations, the furan of formula (A) is combined with the nitroalkane of formula (I) in the presence of a base and optionally a solvent to produce the furan of formula (Q).

In some variations, combining a compound of formula (A) and a nitroalkane of formula (I) produces a compound of formula (Q); a compound of formula (AB) as described above; a compound of formula (B) as described above; or a compound of formula (R); or any combinations thereof. The compound of formula (R) is described in further detail below.

Compounds of Formula (R)

In other aspects, provided herein are haloalkyl(furan) nitrovinyl compounds. In some variations, the haloalkyl (furan)nitrovinyl compounds are compounds of formula (R):

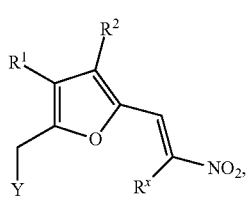

(R)

wherein:
Y is halo; and
$R^1$, $R^2$ and $R^x$ are independently H or alkyl.

In some variations, Y is chloro. In other variations, Y is bromo, iodo, or fluoro. For example, in certain variations, Y is chloro, and the compound of formula (R) is:

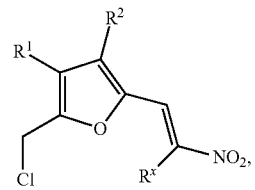

wherein $R^1$, $R^2$, and $R^x$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the Y, $R^x$, $R^1$, and $R^2$ described herein may be combined the same as if each and every combination for the variables were specifically and individually listed.

For example, in certain embodiments, $R^1$ and $R^2$ are H, and the compound of formula (R) is:

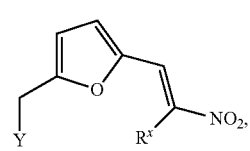

wherein Y is halo, and $R^x$ is H or alkyl.

In other embodiments, $R^x$, $R^1$ and $R^2$ are all H, and the compound of formula (R) is:

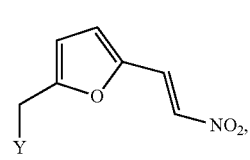

wherein Y is halo.

In yet other embodiments, $R^x$, $R^1$ and $R^2$ are all H, Y is chloro, the compound is the (E) isomer, the compound of formula (R) is 2-(chloromethyl)-5-[(E)-2-nitroethenyl]furan (or (E)-2-(chloromethyl)-5-(2-nitrovinyl)furan):

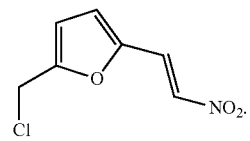

In yet other embodiments, $R^x$, $R^1$ and $R^2$ are all H, Y is chloro, the compound is the (Z) isomer, and the compound of formula (R) is 2-(chloromethyl)-5-[(Z)-2-nitroethenyl]furan (or (Z)-2-(chloromethyl)-5-(2-nitrovinyl)furan).

Provided herein are also solid forms of 2-(chloromethyl)-5-[(E)-2-nitroethenyl]furan, a compound of formula (R) wherein $R^x$, $R^1$ and $R^2$ are all H, and Y is chloro. In one aspect, provided is a crystalline form of 2-(chloromethyl)-5-[(E)-2-nitroethenyl]furan. In another aspect, compositions that include the crystalline form of 2-(chloromethyl)-5-[(E)-2-nitroethenyl]furan are also provided.

Figure 5:
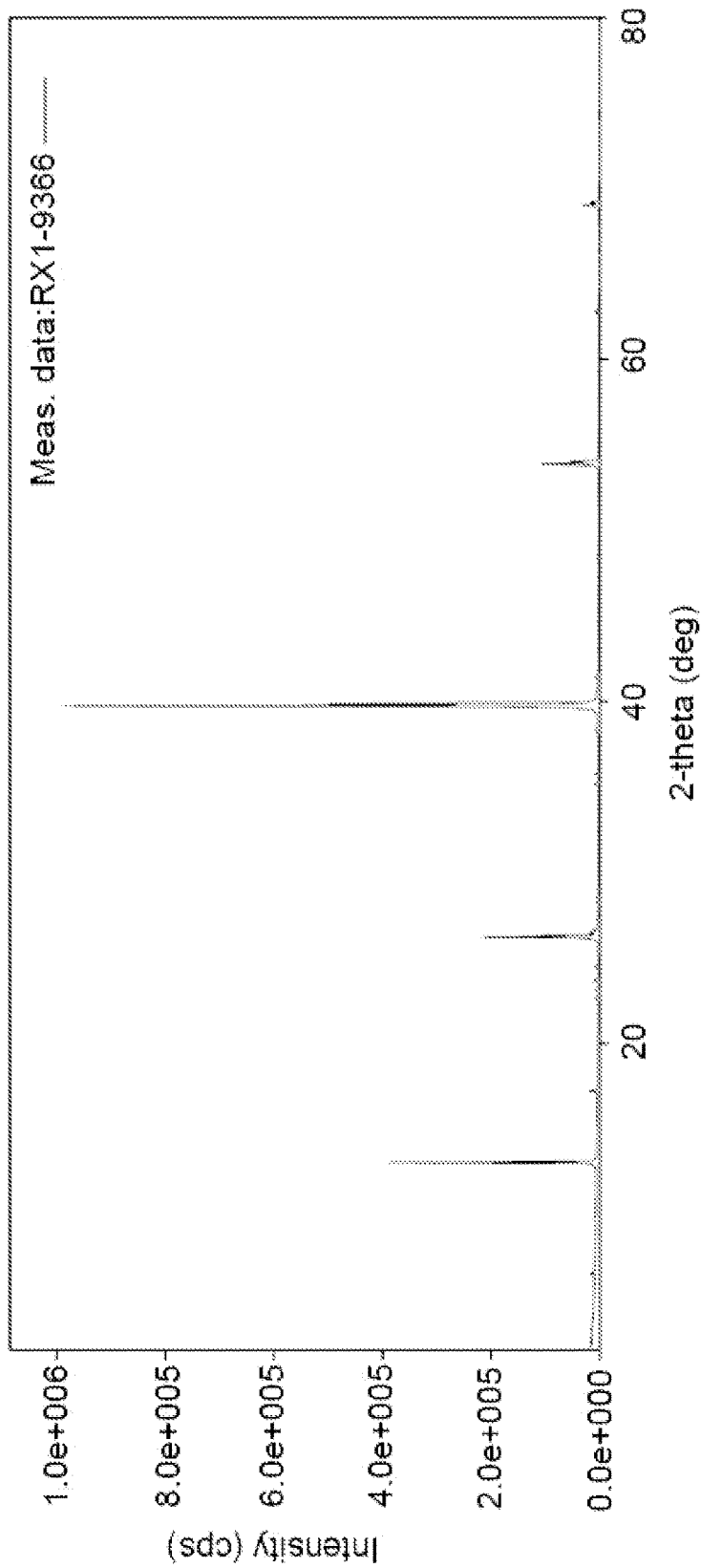
FIG. 5 depicts an X-ray powder diffraction (XRPD) pattern of 2-(chloromethyl)-5-[(E)-2-nitroethenyl]furan.

In a certain aspect, provided is the compound of 2-(chloromethyl)-5-[(E)-2-nitroethenyl]furan, having an X-ray powder diffraction pattern substantially as shown in FIG. 5. The term "substantially as shown in" when referring to an XRPD (such as an XRPD of 2-(chloromethyl)-5-[(E)-2-nitroethenyl]furan) means that a pattern that is not necessarily identical to those depicted herein, but that falls within the limits of experimental error or deviations, when considered by one of ordinary skill in the art.

In some embodiments, 2-(chloromethyl)-5-[(E)-2-nitroethenyl]furan has an X-ray powder diffraction pattern displaying at least two, at least three, at least four, or at least five, of the largest peaks as the X-ray powder diffraction pattern substantially as shown in FIG. 5.

In some embodiments, 2-(chloromethyl)-5-[(E)-2-nitroethenyl]furan has an X-ray powder diffraction pattern that includes at least one peak at about 39.8 degrees 2θ. In certain embodiments, 2-(chloromethyl)-5-[(E)-2-nitroethenyl]furan has an X-ray powder diffraction pattern that further includes at least one additional peak at about 13.0 degrees 2θ, about 26.2 degrees 2θ, about 53.9 degrees 2θ, or about 69.0 degrees 2θ. In certain embodiments, 2-(chloromethyl)-5-[(E)-2-nitroethenyl]furan has an X-ray powder diffraction pattern that further includes at least two additional peaks, at least three additional peaks, or at least four additional peaks independently selected from at about 13.0 degrees 2θ, at about 26.2 degrees 2θ, at about 53.9 degrees 2θ, or at about 69.0 degrees 2θ.

For example, in one embodiment, 2-(chloromethyl)-5-[(E)-2-nitroethenyl]furan has an X-ray powder diffraction pattern that includes at least peaks at about 13.0 degrees 2θ, about 26.2 degrees 2θ, about 39.8 degrees 2θ, about 53.9 degrees 2θ, and about 69.0 degrees 2θ. The use of the term "about" includes and describes the value or parameter per se. For example, "about x" includes and describes "x" per se. With reference to the example provided above regarding the X-ray powder diffraction pattern of 2-(chloromethyl)-5-[(E)-2-nitroethenyl]furan, the use of the term "about" is intended and understood to include an X-ray powder diffraction pattern with at least peaks at 13.0 degrees 2θ, at 26.2 degrees 2θ, at 39.8 degrees 2θ, at 53.9 degrees 2θ, and at 69.0 degrees 2θ.

It should be understood that relative intensities can vary depending on a number of factors, including sample preparation, mounting, and the instrument and analytical procedure and settings used to obtain the spectrum. As such, the peak assignments listed herein are intended to encompass variations of +/−0.5 degrees 2θ, +/−0.4 degrees 2θ, +/−0.33 degrees 2θ, +/−0.3 degrees 2θ, or +/−0.2 degrees 2θ. In other words, "about x degrees 2θ" is intended to encompass variations of +/−0.5 degrees 2θ, +/−0.4 degrees 2θ, +/−0.33 degrees 2θ, +/−0.3 degrees 2θ, +/−0.2 degrees 2θ, or +/−0.01 degrees 2θ to 0.03 degrees 2θ. In other instances, the term "about" when used in association with other measurements, or used to modify a value, a unit, a constant, or a range of values, refers to variations of +/−5%.

Methods of Producing Compounds of Formula (R)

In certain aspects, provided herein are also methods of producing haloalkyl(furan)nitrovinyl compounds, including, for example, the compounds of formula (R). For example, with reference to FIG. 4, process 400 depicts an exemplary pathway to produce an example of a furan of formula (R) from an example of a furan of formula (Q), wherein Y is chloro and $R^1$ and $R^2$ are both H. In step 404, the furan of formula (Q) is undergoes elimination (is dehydrated) via acid catalysis to produce the furan of formula (R).

It should be understood that while FIG. 4 depicts the compounds of formulae (Q) and (R) wherein Y is chloro, in other variations Y is bromo, fluoro, or iodo. It should be further understood that while FIG. 4 depicts the compounds of formulae (Q) and (R) wherein $R^1$ and $R^2$ are both H, in other variations at least one of $R^1$ and $R^2$ is alkyl, while in certain other variations $R^1$ and $R^2$ are both alkyl. It should also be understood that while FIG. 4 depicts the (E)-isomer of the compound of formula (R), the compound of formula (R) may be the (E)-isomer, the (Z)-isomer, or a mixture thereof.

Variations of the methods of producing haloalkyl(furan)nitrovinyl compounds, including, for example, the compounds of formula (R), are exemplified in General Reaction Scheme R described below.

General Reaction Scheme R

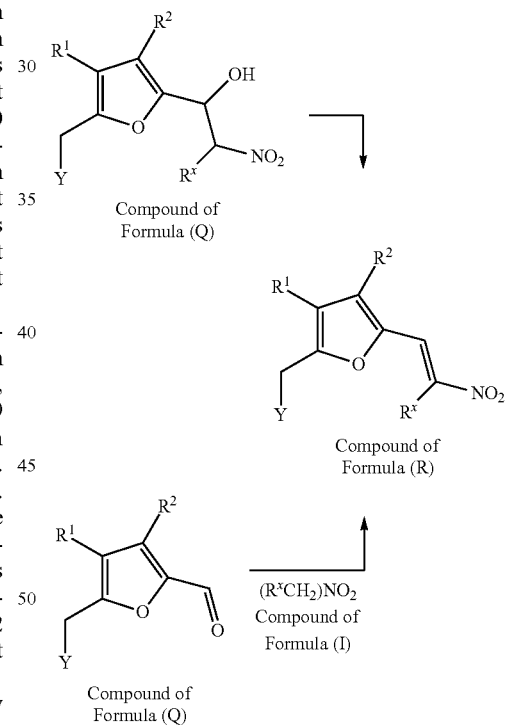

General Reaction Scheme R depicts an exemplary reaction to produce a furan of formula (R), wherein $R^1$ and $R^2$ are independently H or alkyl, and $R^x$ is H or alkyl, from a compound of formula (Q), wherein $R^1$ and $R^2$ are independently H or alkyl, and Y is halo. Also depicted in General Reaction Scheme R is an exemplary reaction to produce a furan of formula (R), wherein $R^1$ and $R^2$ are independently H or alkyl, and $R^x$ is H or alkyl, from a compound of formula (A), wherein $R^1$ and $R^2$ are independently H or alkyl, and Y is halo, and a compound of formula (I), wherein $R^x$ is H or alkyl.

In some variations, the furan of formula (Q) undergoes elimination at a pH below or equal to 2 to produce a compound of formula (R). In some variations, an acid catalyst is combined with the furan of formula (Q) to produce the furan of formula (R). Any suitable acid catalyst may be used. Suitable acid catalysts may include, for example, mineral acids (such as phosphoric acid or HCl) or carboxylic acids. In some variations, the acid catalyst is HCl or acetic acid. In some variations, the furan of formula (Q) undergoes elimination to produce a compound of formula (R) in the presence of HCl at a concentration between 2 to 12.5 M, between 5 to 12.5 M, between 8 to 12.5 M, between 10 to 12.5 M, between 11.5 to 12.5 M, between 3 to 8 M, between 4 to 7 M, at 6 M, or at 12 M.

The furan of formula (Q) may undergo elimination via acid catalysis at any suitable temperature to produce the furan of formula (R). In some variations, the furan of formula (Q) undergoes elimination at a temperature below 25° C., below 50° C., below 75° C., above 75° C., between −25° C. and 125° C., between 0° C. and 100° C., between −25° C. and 25° C., between 0° C. and 25° C., between 75° C. and 125° C., or between 75° C. and 100° C. In certain variations, the furan of formula (Q) is combined with HCl at a temperature below 25° C. to produce the compound of formula (R), while in other variations the furan of formula (Q) is combined with acetic acid at a temperature above 75° C. to produce the furan of formula (R).

In some variations, the compound of formula (Q) is dehydrated to produce the furan of formula (R) at a temperature of 25° C. In some variations, the compound of formula (Q) is dehydrated at a pH below or equal to 2 to produce the furan of formula (R). In certain variations, the compound of formula (Q) is combined with an acid catalyst to produce the furan of formula (R).

Thus, in certain aspects, provided herein are methods of producing a compound of formula (R) by:
converting a compound of formula (Q) to a compound of formula (R).

It should be understood that when the compound of formula (Q) is used to produce the furan of formula (R), $R^1$, $R^2$, $R^x$, and Y in formulae (Q) and (R) are the same.

As described above, a furan of formula (Q) may be produced by combining a furan of formula (A) with a nitroalkane of formula (I). Thus, in one aspect, provided herein is a method that includes:
converting a furan of formula (A) to a furan of formula (Q) by a nitro-aldol reaction; and
converting the furan of formula (Q) to a furan of formula (R).

It should be understood that when the compound of formula (A) is used to produce the furans of formulae (Q) and (R), $R^1$, $R^2$ and Y in formulae (A), (Q), and (R) are the same.

In some variations of formulae (A), (Q), and (R), Y is chloro. In some variations of formulae (Q) and (R), $R^1$, $R^2$, and $R^x$ are H. In certain variations of formulae (A), (Q), and (R), Y is chloro and $R^1$, $R^2$, and $R^x$ are H. Thus, in some variations,
the furan of formula (A) is:

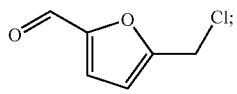

the furan of formula (Q) is:

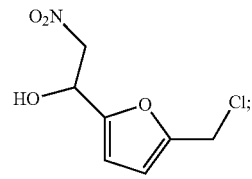 [SMILES: O=[N+]([O-])CC(O)c1ccc(CCl)o1]

and
the furan of formula (R) is:

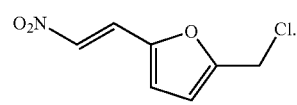 [SMILES: O=[N+]([O-])/C=C/c1ccc(CCl)o1]

In other variations of the compounds of formulae (Q) and (R), $R^x$ is alkyl. In certain variations of the compounds of formulae (Q) and (R), $R^x$ is $C_{1-20}$ alkyl, or $C_{1-10}$ alkyl, or $C_{1-5}$ alkyl. In certain variations, $R^x$ is methyl, ethyl, propyl or butyl.

In some variations of the reaction depicted in General Reaction Scheme R, the compound of formula (A) and the nitroalkane of formula (I) are combined in the presence of a base and optionally a solvent to produce the compound of formula (R). Any suitable base may be used.

In certain variations, a furan of formula (A) is combined with a nitroalkane of formula (I) in the presence of a base and optionally solvent to produce a reaction mixture, and an acid is added to the reaction mixture to produce the furan of formula (R). Any suitable base and acid may be used. In some embodiments, the acid is a mineral acid (such as phosphoric acid or HCl) or a carboxylic acid. For example, in one embodiment, a furan of formula (A) is combined with a nitroalkane of formula (I) in the presence of n-butyllithium and optionally solvent to form a reaction mixture, then HCl is added to the reaction mixture to produce the furan of formula (R). In certain embodiments, 12 M HCl is added to the reaction mixture.

For example, in some variations, the base is a non-nucleophilic base. In certain variations, the base is a non-nucleophilic base that forms a weak acid upon protonation. In certain variations, the base is cesium carbonate ($CsCO_3$) or an amine, such as triethylamine. In other variations, the base is ammonium acetate or alumina. A combination of any of the bases described herein may also be used.

In some variations, the solvent includes an aromatic solvent or an alkyl acetate solvent. In one variation, the solvent is toluene, methyl acetate, ethyl acetate, or propyl acetate. A combination of any of the solvents described herein may also be used.

In some variations, the compound of formula (A) is combined with the nitroalkane of formula (I) to produce the furan of formula (R) at a temperature between 0° C. and 100° C., between 10° C. and 100° C., between 10° C. and 50° C., between 10° C. and 30° C., or between 20° C. and 30° C. In some variations, the compound of formula (A) is combined with the nitroalkane of formula (I) to produce the furan of formula (R) at a pressure between 1 atma to 2 atma.

Thus, in certain aspects, provided herein are methods of producing a compound of formula (R) by:
combining a compound of formula (A) with a nitroalkane of formula (I), to produce a furan of formula (R).

In some variations, the furan of formula (A) is:

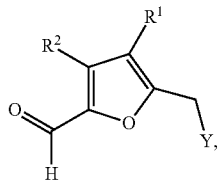

(A)

wherein:

Y is halo; and

R$^1$ and R$^2$ are independently H or alkyl.

In some variations, Y is chloro. In other variations, Y is bromo, iodo, or fluoro.

In some variations, the nitroalkane compound of formula (I) is:

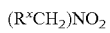

(I), wherein R$^x$ is H or alkyl.

It should be understood that when the compound of formula (I) is used to produce the furan of formula (R), R$^1$, R$^2$, and Y in formulae (I) and (R) are the same. In some variations, the furan of formula (A) is combined with the nitroalkane of formula (I) in the presence of a base and optionally a solvent to produce the furan of formula (R).

In some variations, combining a compound of formula (A) and a nitroalkane of formula (I) produces (R) as described above; a compound of formula (Q) as described above; a compound of formula (AB) as described above; or a compound of formula (B) as described above; or any combinations thereof.

Compounds of Formula (M)

In other aspects, provided herein are (furan)acetonitrile compounds. In some variations, the (furan)acetonitrile compounds are compounds of formula (M):

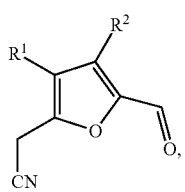

(M)

wherein:

R$^1$ and R$^2$ are independently H or alkyl.

In some variations, R$^1$ and R$^2$ are both H. In other variations, at least one of R$^1$ and R$^2$ is alkyl. For example, in some variations, R$^1$ is H and R$^2$ is alkyl. In other variations R$^1$ is alkyl and R$^2$ is H. In yet other variations, both R$^1$ and R$^2$ are alkyl. In certain variations, R$^1$ and R$^2$ are independently H or C$_{1-20}$ alkyl, C$_{1-10}$ alkyl, or C$_{1-5}$ alkyl. In other variations, R$^1$ and R$^2$ are independently H or methyl, ethyl, propyl, or butyl.

In certain embodiments, R$^1$ and R$^2$ are H, and the compound of formula (M) is:

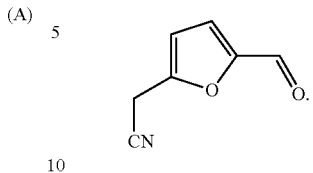

Methods of Producing Compounds of Formula (M)

In certain aspects, provided herein are also methods of producing (furan)acetonitrile compounds, including, for example, the compounds of formula (M).

Figure 2:
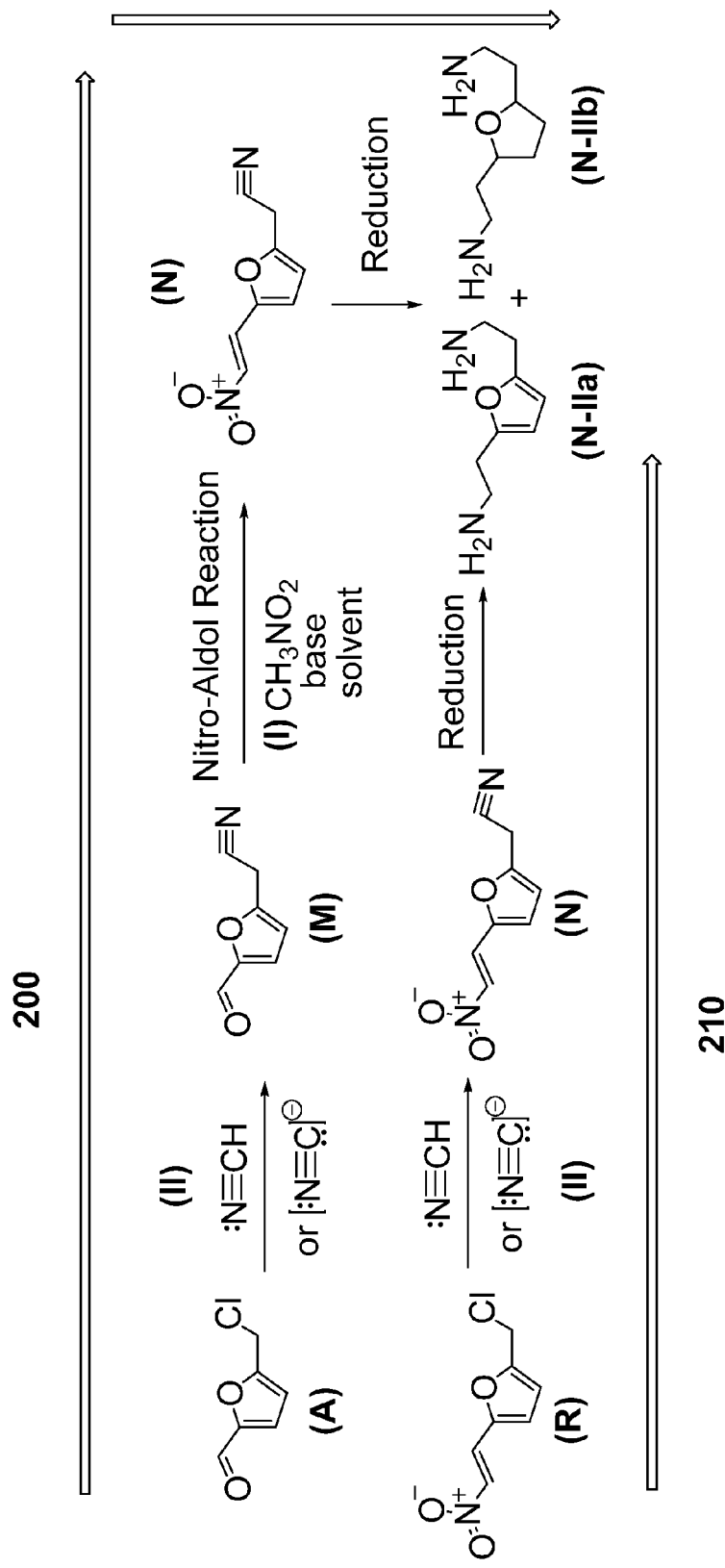
FIG. 2 depicts an exemplary process to produce 2,2'-(furan-2,5-diyl)diethanamine and 2,2'-(tetrahydrofuran-2,5-diyl)diethanamine from 5-(chloromethyl)furan-2-carbaldehyde or 2-(chloromethyl)-5-(2-nitrovinyl)furan.

For example, with reference to FIG. 2, process 200 depicts an exemplary pathway to produce an example of a compound of formula (M) from an example of a compound of formula (A). In the first step of process 200, 5-(chloromethyl)furfural (one example of a compound of formula (A) wherein R$^1$ and R$^2$ are H, and Y is chloro) is combined with N≡CH or N≡C$^-$ (examples of a compound of formula (II)) to produce 2-(5-formylfuran-2-yl)acetonitrile (one example of a compound of formula (M) wherein R$^1$ and R$^2$ are H).

It should be understood that the N≡CH or N≡C$^-$ may be added to the reaction mixture, or generated in situ. It should further be understood that while process 200 in FIG. 2 depicts compound of formula (A) wherein Y is chloro, in other embodiments Y is bromo, iodo or fluoro. It should also be understood that while FIG. 2 depicts the compounds of formulae (A) and (M) wherein R$^1$ and R$^2$ are H, in other embodiments at least one of R$^1$ and R$^2$ is alkyl. In certain embodiments, both R$^1$ and R$^2$ are alkyl.

Variations of the methods of producing (furan)acetonitrile compounds, including, for example, the compounds of formula (M), are exemplified in General Reaction Scheme M described below.

General Reaction Scheme M

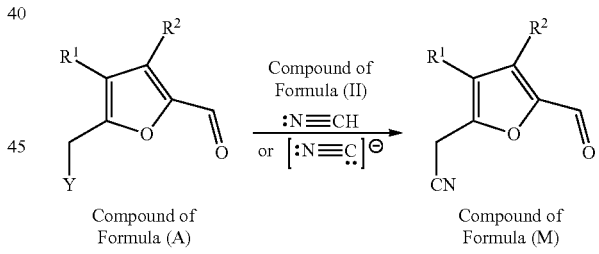

Compound of Formula (A)    Compound of Formula (M)

General Reaction Scheme M depicts an exemplary reaction to produce a furan of formula (M), wherein R$^1$ and R$^2$ are independently H or alkyl, from a compound of formula (A), wherein R$^1$ and R$^2$ are independently H or alkyl, and Y is halo, and a compound of formula (II) having the structure of either N≡CH or N≡C$^-$.

In some embodiments, the compound of formula (II) is N≡CH or N≡C$^-$. In other embodiments, the compound of formula (II) comprises N≡C$^-$. In some embodiments, the compound of formula (II) comprises a salt of N≡C$^-$. For example, in some embodiments, the compound of formula (II) comprises N≡C$^-$ and one or more cations. In certain variations, the compound of formula (II) comprises N≡C$^-$ and one or more Group I cations or one or more Group II cations, or any mixtures thereof. For example, in certain embodiments, the compound of formula (II) comprises N≡C$^-$ and Na$^+$, or N≡C$^-$ and K$^+$, or a mixture thereof.

In some variations, the compound of formula (A) is combined with the compound of formula (II) at a temperature between −25° C. to 400° C., between 100° C. to 400° C., between 200° C. to 400° C., between 300° C. to 400° C., between 0° C. to 300° C., between 0° C. to 200° C., or between 0° C. to 100° C. to produce the furan of formula (M).

In some variations, the compound of formula (A) is combined with the compound of formula (II) in the additional presence of solvent to produce the furan of formula (M).

Thus, in certain aspects, provided herein is a method that includes:
combining a furan of formula (A) with a compound of formula (II) having the structure of either N≡CH or N≡C⁻ to produce a furan of formula (M).

It should be understood that when the compound of formula (A) is used to produce the furan of formula (M), $R^1$ and $R^2$ in formulae (A) and (M) are the same.

Compounds of Formula (MN)

In other aspects, provided herein are nitroethanol(furan) acetonitrile compounds. In some variations, the nitroethanol (furan)acetonitrile compounds are compounds of formula (MN):

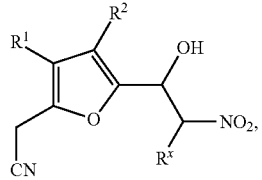

(MN)

wherein:
$R^1$, $R^2$, and $R^x$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

In certain embodiments, $R^1$ and $R^2$ are both H, and the compound of formula (MN) is:

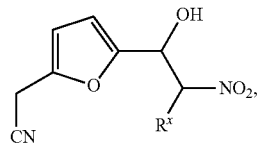

wherein $R^x$ is H or alkyl.

In other embodiments, $R^1$, $R^2$, and $R^x$ are each H, and the compound of formula (MN) is:

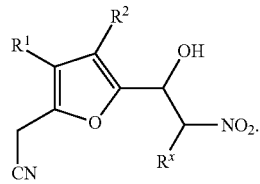

Methods of Producing Compounds of Formula (MN)

In certain aspects, provided herein are also methods of producing nitroethanol(furan)acetonitrile compounds, including, for example, the compounds of formula (MN). Variations of the methods of producing nitroethanol(furan) acetonitrile compounds, including, for example, the compounds of formula (MN), are exemplified in General Reaction Scheme MN described below.

General Reaction Scheme MN

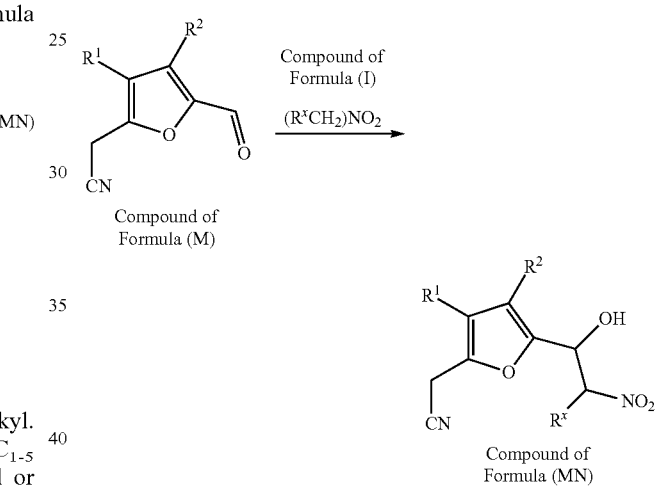

General Reaction Scheme MN depicts an exemplary reaction to produce a furan of formula (MN), wherein $R^1$, $R^2$, and $R^x$ are independently H or alkyl, from a compound of formula (M), wherein $R^1$ and $R^2$ are independently H or alkyl, and a compound of formula (I), wherein $R^x$ is H or alkyl.

In some variations of the reaction depicted in General Reaction Scheme MN, the compound of formula (M) and the nitroalkane of formula (I) are combined in the presence of a base and optionally a solvent to produce the compound of formula (MN). Any suitable base may be used.

For example, in some variations, the base is a non-nucleophilic base. In certain variations, the base is a non-nucleophilic base that forms a weak acid upon protonation. In certain variations, the base is cesium carbonate ($CsCO_3$) or an amine, such as triethylamine. In other variations, the base is ammonium acetate or alumina. A combination of any of the bases described herein may also be used.

In some variations, the solvent includes an aromatic solvent or an alkyl acetate solvent. In one variation, the solvent is toluene, methyl acetate, ethyl acetate, or propyl acetate. A combination of any of the solvents described herein may also be used.

In some variations, the compound of formula (M) is combined with the nitroalkane of formula (I) to produce the furan of formula (MN) at a temperature between 0° C. and 100° C., between 10° C. and 100° C., between 10° C. and 50° C., between 10° C. and 30° C., or between 20° C. and 30° C. In some variations, the compound of formula (M) is combined with the nitroalkane of formula (I) to produce the furan of formula (MN) at a pressure between 1 atma to 2 atma.

Thus, in certain aspects, provided herein are methods of producing a compound of formula (MN) by:
combining a compound of formula (M) with a nitroalkane of formula (I), to produce a furan of formula (MN).

In some variations, the furan of formula (M) is:

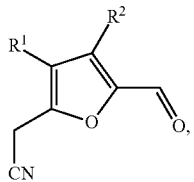

(M)

wherein:
R¹ and R² are independently H or alkyl.
In some variations, the nitroalkane compound of formula (I) is:

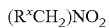

(R$^x$CH$_2$)NO$_2$  (I), wherein R$^x$ is H or alkyl.

It should be understood that when the compound of formula (M) is used to produce the furan of formula (MN), R¹ and R² in formulae (M) and (MN) are the same. It should be further understood that when the compound of formula (I) is used to produce the furan of formula (MN), R$^x$ in formulae (I) and (MN) are the same.

As described above, in some variations, a furan of formula (M) may be produced by combining a furan of formula (A) with a compound of formula (II) having the structure of either N≡CH or N≡C⁻ to produce a furan of formula (M).

Thus, in certain aspects, provided herein is a method that includes:
combining a furan of formula (A) with a compound of formula (II) having the structure of either N≡CH or N≡C⁻ to produce a furan of formula (M); and
combining the furan of formula (M) with a nitroalkane of formula (I) to produce a furan of formula (MN).

It should be understood that when a furan of formula (A) is used to produce a furan of formula (M) and/or (MN), R¹ and R² in formulae (A), (M), and (MN) are the same.

Compounds of Formula (N)

In other aspects, provided herein are nitrovinyl(furan) acetonitrile compounds. In some variations, the nitrovinyl (furan)acetonitrile compounds are compounds of formula (N):

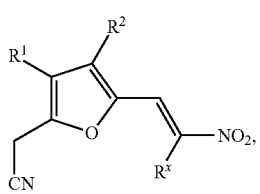

(N)

wherein:
R¹, R², and R$^x$ are independently H or alkyl.
In some variations, R$^x$ is H. In other variations, R$^x$ is alkyl. In certain variations, R$^x$ is C$_{1-20}$ alkyl, or C$_{1-10}$ alkyl, or C$_{1-5}$ alkyl. In some variations, R$^x$ is methyl, ethyl, propyl or butyl.

In some variations, R¹ and R² are both H. In other variations, at least one of R¹ and R² is alkyl. For example, in some variations, R¹ is H and R² is alkyl. In other variations R¹ is alkyl and R² is H. In yet other variations, both R¹ and R² are independently alkyl. In certain variations, R¹ and R² are independently H or C$_{1-20}$ alkyl, C$_{1-10}$ alkyl, or C$_{1-5}$ alkyl. In other variations, R¹ and R² are independently H or methyl, ethyl, propyl or butyl.

It should be generally understood that any of the variations for the R$^x$, R¹, and R² described herein may be combined the same as if each and every combination for the variables were specifically and individually listed.

In certain embodiments, R¹ and R² are both H, and the compound of formula (N) is:

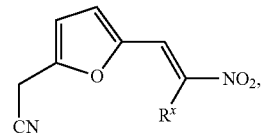

wherein R$^x$ is H or alkyl.
In other embodiments, R¹, R², and R$^x$ are each H, and the compound of formula (N) is:

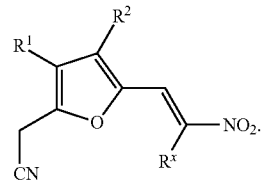

Methods of Producing Compounds of Formula (N)

In certain aspects, provided herein are also methods of producing nitrovinyl(furan)acetonitrile compounds, including, for example, the compounds of formula (N).

For example, with reference to FIG. 2, process 200 depicts one pathway to produce an example of a compound of formula (N). In the second step of process 200, 2-(5-formylfuran-2-yl)acetonitrile (an example of a compound of formula (M)) undergoes a nitro-aldol reaction with nitromethane (an example of a compound of formula (I)) to produce 2-(5-(2-nitrovinyl)furan-2-yl)acetonitrile (an example of a compound of formula (N)). As depicted in FIG. 2, the 2-(5-formylfuran-2-yl)acetonitrile may be combined with a nitroalkane of formula (I) in the presence of a base and solvent to produce the furan of formula (N).

With reference again to FIG. 2, process 210 depicts another pathway to produce an example of a compound of formula (N). In the first step of process 210, 2-(chloromethyl)-5-(2-nitrovinyl)furan (an example of a compound of formula (R)) is combined with N≡CH or N≡C⁻ (examples of a compound of formula (II)) to produce 2-(5-(2-nitrovinyl) furan-2-yl)acetonitrile (an example of a compound of formula (N)). It should be understood that the N≡CH or N≡C⁻ may be added to the reaction mixture, or generated in situ.

It should also be understood that while process 200 and process 210 in FIG. 2 depict the (E)-isomer of 2-(5-(2-nitrovinyl)furan-2-yl)acetonitrile (an example of a compound of formula (N)), the compound of formula (N) may be the (E)-isomer, the (Z)-isomer, or a mixture thereof.

It should further be understood that while FIG. 2 depicts the compounds of formulae (R), (M), and (N) wherein $R^1$ and $R^2$ are H, in other embodiments at least one of $R^1$ and $R^2$ is alkyl. In certain embodiments, both $R^1$ and $R^2$ are alkyl. While FIG. 2 depicts formulae (I) and (N) wherein $R^x$ is H, in some embodiments $R^x$ is alkyl.

General Reaction Scheme N

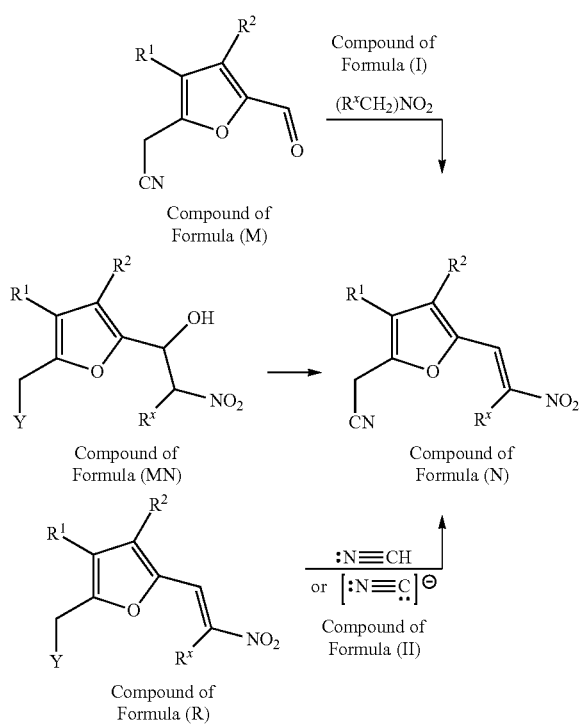

General Reaction Scheme N depicts three exemplary reactions to produce a furan of formula (N), wherein $R^1$, $R^2$, and $R^x$ are independently H or alkyl.

In one variation, a furan of formula (N), wherein $R^1$, $R^2$, and $R^x$ are independently H or alkyl, is produced from a compound of formula (R), wherein $R^1$ and $R^2$ are independently H or alkyl, and Y is halo, and a compound of formula (II) having the structure of either N≡CH or N≡C⁻.

In some embodiments, the compound of formula (II) is N≡CH or N≡C⁻. In other embodiments, the compound of formula (II) comprises N≡C⁻. In some embodiments, the compound of formula (II) comprises a salt of N≡C⁻. For example, in some embodiments, the compound of formula (II) comprises N≡C⁻ and one or more cations. In certain variations, the compound of formula (II) comprises N≡C⁻ and one or more Group I cations or one or more Group II cations, or any mixtures thereof. For example, in certain embodiments, the compound of formula (II) comprises N≡C⁻ and Na⁺, or N≡C⁻ and K⁺, or a mixture thereof.

In some variations, the compound of formula (R) is combined with the compound of formula (II) at a temperature between −25° C. to 400° C., between 100° C. to 400° C., between 200° C. to 400° C., between 300° C. to 400° C., between 0° C. to 300° C., between 0° C. to 200° C., or between 0° C. to 100° C. to produce the furan of formula (N).

In some variations, the compound of formula (R) is combined with the compound of formula (II) in the additional presence of solvent to produce the furan of formula (N).

General Reaction Scheme N also depicts an exemplary reaction to produce a furan of formula (N), wherein $R^1$, $R^2$, and $R^x$ are independently H or alkyl, from a compound of formula (M), wherein $R^1$ and $R^2$ are independently H or alkyl, by nitro-aldol reaction with a compound of formula (I).

In some variations of the reaction depicted in General Reaction Scheme N, the compound of formula (M) and the nitroalkane of formula (I) are combined in the presence of a base and optionally a solvent to produce the compound of formula (N). Any suitable base may be used.

For example, in some variations, the base is a non-nucleophilic base. In certain variations, the base is a non-nucleophilic base that forms a weak acid upon protonation. In certain variations, the base is cesium carbonate ($CsCO_3$) or an amine, such as triethylamine. In other variations, the base is ammonium acetate or alumina. A combination of any of the bases described herein may also be used.

In certain variations, a compound of formula (M) is combined with a nitroalkane of formula (I) in the presence of a base and optionally solvent to produce a reaction mixture, and an acid is added to the reaction mixture to produce the furan of formula (N). Any suitable base and acid may be used. In some embodiments, the acid is a mineral acid (such as phosphoric acid or HCl) or a carboxylic acid. For example, in one embodiment, a compound of formula (M) is combined with a nitroalkane of formula (I) in the presence of n-butyllithium and optionally solvent to form a reaction mixture, then HCl is added to the reaction mixture to produce the furan of formula (N). In some embodiments, the solvent is hexane. In certain embodiments, 12 M HCl is added to the reaction mixture. In some variations, the solvent includes an aromatic solvent or an alkyl acetate solvent. In one variation, the solvent is toluene, methyl acetate, ethyl acetate, or propyl acetate. A combination of any of the solvents described herein may also be used.

In some variations, the compound of formula (M) is combined with the nitroalkane of formula (I) to produce the furan of formula (N) at a temperature of between 10° C. ans=d 100° C., between 10° C. and 50° C., between 10° C. and 30° C., or between 20° C. and 30° C. In some variations, the compound of formula (M) is combined with the nitroalkane of formula (I) to produce the furan of formula (N) at a pressure of between 1 atma to 2 atma.

General Reaction Scheme N also depicts an exemplary reaction to produce a furan of formula (N), wherein $R^1$, $R^2$, and $R^x$ are independently H or alkyl, from a compound of formula (MN), wherein $R^1$, $R^2$, and $R^x$ are independently H or alkyl.

In some variations, the compound of formula (MN) is combined with an acid catalyst to produce the furan of formula (N). Any suitable acid catalyst may be used. For example, in some embodiments, a mineral acid (such as phosphoric acid or HCl) catalyst is used. In one embodiment, HCl is used as an acid catalyst. In some variations, the compound of formula (MN) is dehydrated to produce the furan of formula (N) at a temperature of 25° C. In some variations, the compound of formula (MN) is dehydrated at a pH below or equal to 2 to produce the furan of formula (N).

Thus, in one aspect, provided herein are methods of producing a compound of formula (N) by:
  combining a furan of formula (R) with a compound of formula (II) having the structure of either N≡CH or N≡C⁻ to produce a furan of formula (N).

As discussed above, the furan of formula (R) may be produced from a furan of formula (Q). Thus, in certain aspects, provided herein are methods of producing a compound of formula (R) by:
  converting a compound of formula (Q) to a compound of formula (R); and
  combining the furan of formula (R) with a compound of formula (II) having the structure of either N≡CH or N≡C⁻ to produce a furan of formula (N).

As described above, a furan of formula (Q) may be produced by combining a furan of formula (A) with a nitroalkane of formula (I). Thus, in another aspect, provided herein are methods of producing a compound of formula (R) by:
  combining a compound of formula (A) with a nitroalkane of formula (I), to produce a furan of formula (Q);
  converting the compound of formula (Q) to a compound of formula (R); and
  combining a furan of formula (R) with a compound of formula (II) having the structure of either N≡CH or N≡C⁻ to produce a furan of formula (N).

It should be understood that when a compound of formula (A), (Q), and/or (R) is used to produce the furan of formula (N), $R^1$ and $R^2$ in formulae (A), (Q), (R), and (N) are the same. When a compound of formula (Q) and/or (R) is used to produce the furan of formula (N), IV and in formulae (Q), (R), and (N) are the same.

In other aspects, provided is a method that includes:
  converting a furan of formula (M) to a furan of formula (N) by a nitro-aldol reaction as described above and in further detail herein.

As described above, a furan of formula (M) may be produced by combining a furan of formula (A) with a compound of formula (II) having the structure of either N≡CH or N≡C⁻. Thus, in another aspect, provided herein are methods of producing a compound of formula (N) by:
  combining a furan of formula (A) with a compound of formula (II) having the structure of either N≡CH or N≡C⁻ to produce a furan of formula (M); and
  converting the furan of formula (M) to a furan of formula (N) by a nitro-aldol reaction as described above and in further detail herein.

In some embodiments, a furan of formula (N) may be produced in a one-pot reaction by combining a furan of formula (A) with a compound of formula (II) having the structure of either N≡CH or N≡C⁻ and a nitroalkane of formula (I). Thus, in yet other aspects, provided herein is a method that includes:
  combining a furan of formula (A) with a nitroalkane of formula (I), and a compound of formula (II) having the structure of either N≡CH or N≡C⁻ to produce a furan of formula (N).

In some embodiments, the furan of formula (A), the nitroalkane of formula (I), and the compound of formula (II) are further combined in the presence of base and optionally a solvent. In certain embodiment, the furan of formula (A), the nitroalkane of formula (I), the compound of formula (II), the base and optionally a solvent are combined to form a reaction mixture, and an acid is then added to the reaction mixture to produce the furan of formula (N).

In other aspects, provided herein are methods of producing a compound of formula (N) by:
  converting a compound of formula (MN) to a compound of formula (N).

It should be understood that when the compound of formula (MN) is used to produce the furan of formula (N), $R^1$, $R^2$, and $R^x$ in formulae (MN) and (N) are the same.

It should be understood that when a compound of formula (A), (M), or (MN) is used to produce the furan of formula (N), $R^1$ and $R^2$ in formulae (A), (M), (MN) and (N) are the same.

Compounds of Formula (N-I)

In other aspects, provided herein are nitroalkyl(furan) acetonitrile compounds. In some variations, the nitroalkyl(furan)acetonitrile compounds are compounds of formula (N-I):

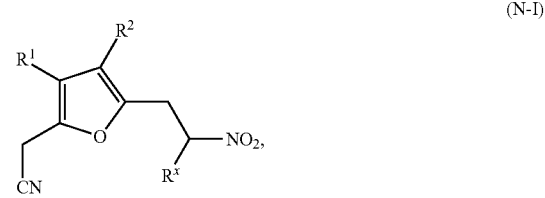

(N-I)

wherein:
  $R^1$, $R^2$, and $R^x$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

In certain embodiments, $R^1$ and $R^2$ are both H, and the compound of formula (N-I) is:

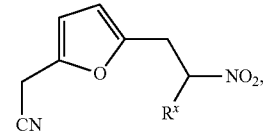

wherein $R^x$ is H or alkyl.

In other embodiments, $R^1$, $R^2$, and $R^x$ are each H, and the compound of formula (N-I) is:

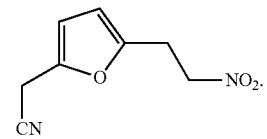 [SMILES: N#CCc1ccc(CC[N+](=O)[O-])o1]

Methods of Producing Compounds of Formula (N-I)

In certain aspects, provided herein are also methods of producing nitroalkyl(furan)acetonitrile compounds, including, for example, the compounds of formula (N-I).

For example, process 300 (FIG. 3) depicts an exemplary pathway to produce nitroalkyl(furan)acetonitrile compound of formula (N-I) from furans of formula (N) in step 302.

Variations of the methods of producing nitroalkyl(furan) acetonitrile compounds, including, for example, the compounds of formula (N-I), are exemplified in General Reaction Scheme N-I described below.

General Reaction Scheme N-I

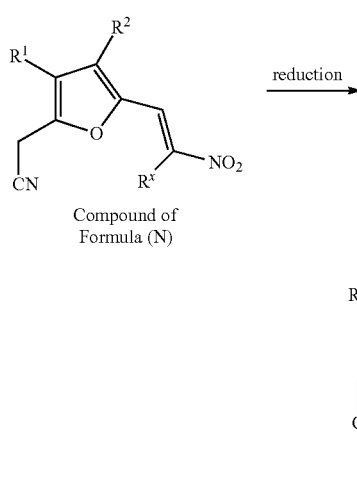

Compound of Formula (N)

Compound of Formula (N-I)

Depicted in General Reaction Scheme N-I is an exemplary reaction to produce a compound of formula (N-I), wherein $R^1$, $R^2$, and $R^x$ are independently H or alkyl, by reducing a compound of formula (N), wherein $R^1$, $R^2$, and $R^x$ are independently H or alkyl.

In some variations of the reaction depicted in General Reaction Scheme N-I, the compound of formula (N) is reduced in the presence of hydrogen to produce the compound of formula (N-I). The hydrogen may be provided in the form of hydrogen gas or by transfer hydrogenation (e.g., by addition of cyclohexene or cyclohexadiene to the reaction mixture as the hydrogen source).

In one variation, the compound of formula (N) is reduced at a pressure of at least 1 psi, or at least 10 psi; or between 1 psi and 1500 psi, between 1 psi and 1000 psi, between 500 psi and 1500 psi, between 1 psi and 50 psi, between 1 psi and 100 psi, between 1 psi and 80 psi, between 1 psi and 75 psi, or between 30 psi and 60 psi to produce the compound of formula (N-I). It should be understood that the hydrogen gas may be dissolved, or at least partially dissolved, in the reagents and/or other solvents described herein.

In some variations, the furan of formula (N) is reduced in the presence of hydrogen and catalyst to produce the compound of formula (N-I). Any suitable catalyst may be used.

In certain variations, the catalyst includes a metal. In certain variations, the catalyst includes palladium, platinum, rhodium, rhenium, or a combination thereof. In one variation, the catalyst includes palladium, platinum, or a combination thereof. For example, the catalyst may be palladium on carbon (Pd/C) or platinum on carbon (Pt/C). In another variation, the catalyst includes rhodium, rhenium, or a combination thereof. For example, the catalyst may be Rh—Re/SiO$_2$.

In some variations, the catalyst further includes a solid support. In certain variation, the catalyst includes a solid acid support. For example, in one variation, the catalyst may include fluorosulfonic acid polymer on amorphous silica (e.g., Nafion® SAC-13).

In some variations, the compound of formula (N) is reduced to produce the compound of formula (N-I) at a temperature between 0° C. to 100° C. In some embodiments, the compound of formula (N) is reduced to produce the compound of formula (N-I) at a temperature between 10° C. to 60° C., or between 10° C. to 50° C.

Thus, in one aspect, provided is a method that includes:
    reducing a compound of formula (N) to produce a compound of formula (N-I).

It should be understood that when a compound of formula (N) is used to produce a compound of formula (N-I), $R^1$, $R^2$, and $R^x$ in formulae (N) and (N-I) are the same.

Compounds of Formula (N-IIa)

In other aspects, provided herein are bis(aminoalkyl)furan compounds. In some variations, the bis(aminoalkyl)furan compounds are compounds of formula (N-IIa):

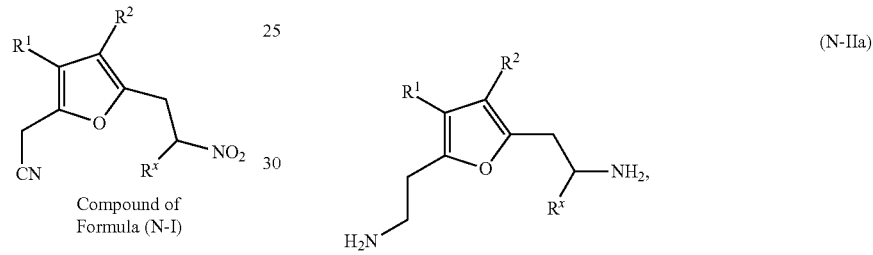

(N-IIa)

wherein:

$R^1$, $R^2$, and $R^x$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

In certain embodiments, $R^1$ and $R^2$ are both H, and the compound of formula (N-IIa) is:

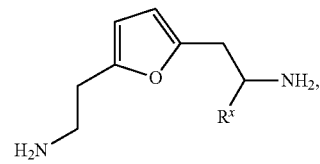

wherein $R^x$ is H or alkyl.

In other embodiments, $R^1$, $R^2$, and $R^x$ are each H, and the compound of formula (N-IIa) is:

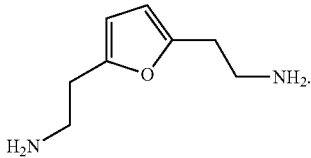

In yet other embodiments, $R^1$ and $R^2$ are both H, $R^x$ is methyl, and the compound of formula (N-IIa) is:

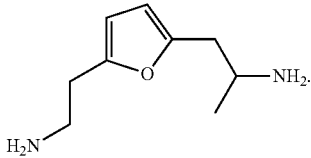

Compounds of Formula (N-IIb)

In other aspects, provided herein are bis(aminoalkyl) tetrahydrofuran compounds. In some variations, the bis (aminoalkyl)tetrahydrofuran compounds are compounds of formula (N-IIb):

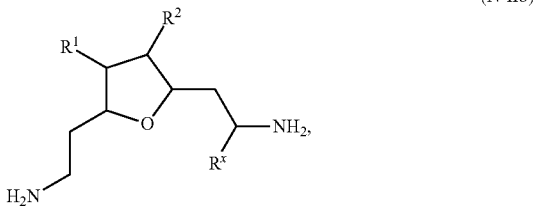

(N-IIb)

wherein:
$R^1$, $R^2$, and $R^x$ are independently H or alkyl.

In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

In certain embodiments, $R^1$ and $R^2$ are both H, and the compound of formula (N-IIb) is:

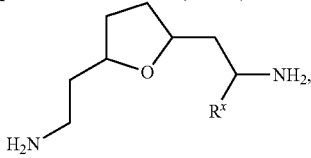

wherein $R^x$ is H or alkyl.

In other embodiments, $R^1$, $R^2$, and $R^x$ are each H, and the compound of formula (N-IIb) is:

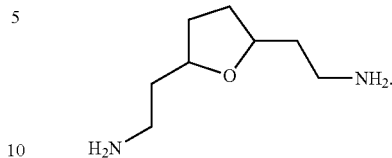

In yet other embodiments, $R^1$ and $R^2$ are both H, $R^x$ is methyl, and the compound of formula (N-IIb) is:

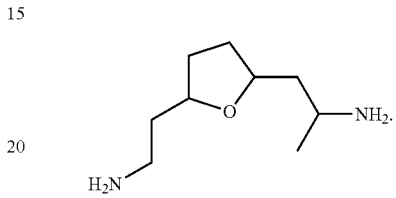

Methods of Producing Compounds of Formula (N-IIa) and Formula (N-IIb)

In certain aspects, provided herein are also methods of producing bis(aminoalkyl)furan and bis(aminoalkyl)tetrahydrofuran compounds, including, for example, the compounds of formula (N-IIa) and formula (N-IIb).

For example, with reference to FIG. 2, process 200 depicts an exemplary pathway to produce 2,2'-(furan-2,5-diyl)diethanamine (an example of a compound of formula (N-IIa)) and 2,2'-(tetrahydrofuran-2,5-diyl)diethanamine (an example of a compound of formula (N-IIb)). In the first step of process 200, 5-(chloromethyl)furfural is combined with N≡CH or N≡C⁻ to produce 2-(5-formylfuran-2-yl)acetonitrile (an example of a compound of formula (M)). The 2-(5-formylfuran-2-yl)acetonitrile can undergo a nitro-aldol reaction to produce 2-(5-(2-nitrovinyl)furan-2-yl)acetonitrile (an example of a compound of formula (N)). As depicted in FIG. 2, the 2-(5-formylfuran-2-yl)acetonitrile may be combined with a nitroalkane, such as $CH_3NO_2$ (an example of a compound of formula (I)) in the presence of a base and solvent to produce the 2-(5-(2-nitrovinyl)furan-2-yl)acetonitrile, which can then be reduced to produce 2,2'-(furan-2,5-diyl)diethanamine (an example of a compound of formula (N-IIa)) and 2,2'-(tetrahydrofuran-2,5-diyl)diethanamine (an example of a compound of formula (N-IIb)).

It should be understood that the N≡CH or N≡C⁻ may be added to the reaction mixture, or generated in situ. It should also be understood that while process 200 of FIG. 2 depicts the (E)-isomer of 2-(5-(2-nitrovinyl)furan-2-yl)acetonitrile (an example of a compound of formula (N)), the compound of formula (N) may be the (E)-isomer, the (Z)-isomer, or a mixture thereof. It should further be understood that while process 200 of FIG. 2 depicts the production of a mixture of a furan of formula (N-IIa) and a tetrahydrofuran of formula (N-IIb), in some embodiments a furan of formula (N-IIa) is produced, while in other embodiments only a tetrahydrofuran of formula (N-IIb) is produced.

Variations of the methods of producing bis(aminoalkyl)furan and bis(aminoalkyl)tetrahydrofuran compounds, including, for example, the compounds of formula (N-IIa) and formula (N-IIb), are exemplified in General Reaction Scheme N-II described below.

General Reaction Scheme N-II

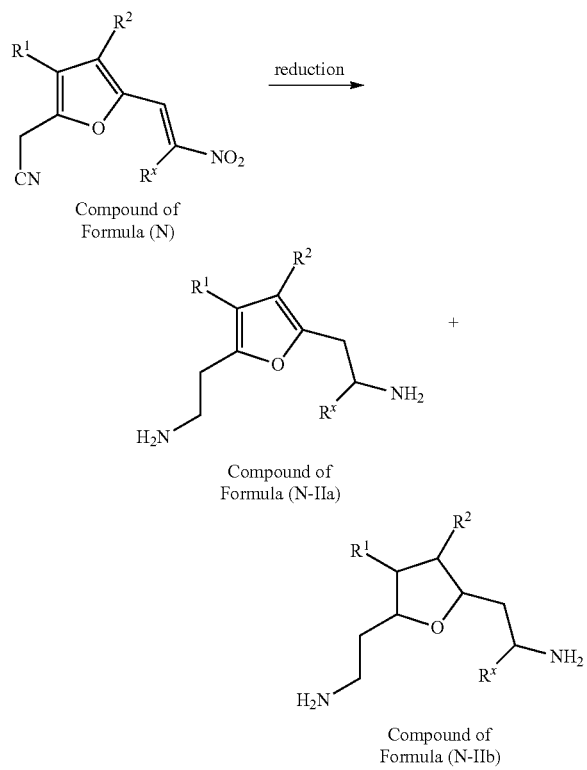

Compound of Formula (N)

Compound of Formula (N-IIa)

Compound of Formula (N-IIb)

General Reaction Scheme N-II depicts an exemplary reaction to produce a furan of formula (N-IIa), wherein $R^1$, $R^2$, and $R^x$ are independently H or alkyl; and a tetrahydrofuran of formula (N-IIb), wherein $R^1$, $R^2$, and $R^x$ are independently H or alkyl; by reducing a compound of formula (N), wherein $R^1$, $R^2$, and $R^x$ are independently H or alkyl, as is described above. It should be understood that while General Reaction Scheme N-II depicts the production of a furan of formula (N-IIa) and a tetrahydrofuran of formula (N-IIb), in some variations only a furan of formula (N-IIa) is produced. In other variations, only a tetrahydrofuran of formula (N-IIb) is produced. In still other variations, a mixture of a furan of formula (N-IIa) and a tetrahydrofuran of formula (N-IIb) is produced.

In some variations of the reaction depicted in General Reaction Scheme N-II, the compound of formula (N) is reduced in the presence of hydrogen to produce the furan of formula (N-IIa) or tetrahydrofuran of formula (N-IIb), or combination thereof. The hydrogen may be provided in the form of hydrogen gas or by transfer hydrogenation (e.g., by addition of cyclohexene or cyclohexadiene to the reaction mixture as the hydrogen source).

In one variation, the compound of formula (N) is reduced at a pressure of at least 1 psi, or at least 10 psi; or between 1 psi and 1500 psi, between 1 psi and 1000 psi, between 500 psi and 1500 psi, between 1 psi and 50 psi, between 1 psi and 100 psi, between 1 psi and 80 psi, between 1 psi and 75 psi, or between 30 psi and 60 psi to produce the compound of formula (N-I), the compound of formula (N-IIb), or a combination thereof. It should be understood that the hydrogen gas may be dissolved, or at least partially dissolved, in the reagents and/or other solvents described herein.

In some variations, the furan of formula (N) is reduced in the presence of hydrogen and catalyst to produce the compound of formula (N-IIa) or (N-IIb). Any suitable catalyst may be used.

In certain variations, the catalyst includes a metal. In certain variations, the catalyst includes palladium, platinum, rhodium, rhenium, or a combination thereof. In one variation, the catalyst includes palladium, platinum, or a combination thereof. For example, the catalyst may be palladium on carbon (Pd/C) or platinum on carbon (Pt/C). In another variation, the catalyst includes rhodium, rhenium, or a combination thereof. For example, the catalyst may be Rh—Re/SiO$_2$.

In some variations, the catalyst further includes a solid support. In certain variation, the catalyst includes a solid acid support. For example, in one variation, the catalyst may include fluorosulfonic acid polymer on amorphous silica (e.g., Nafion® SAC-13).

In some variations, the compound of formula (N) is reduced to produce the compound of formula (N-IIa) or (N-IIb) at a temperature between 10° C. to 100° C. In certain variations, the compound of formula (N) is reduced to produce the compound of formula (N-IIa) or (N-IIb) at a temperature between 10° C. to 60° C., or between 10° C. to 50° C.

Thus, in certain aspects, provided herein are methods of producing a compound of formula (N-IIa), a compound of formula (N-IIb), or a combination thereof by:

reducing a compound of formula (N) to produce a furan of formula (N-IIa), a tetrahydrofuran of formula (N-IIb), or a combination thereof.

It should be understood that when the compound of formula (N) is used to produce a furan of formula (N-IIa) or a tetrahydrofuran of formula (N-IIb), $R^1$, $R^2$, and $R^x$ in formulae (N), (N-IIa) and (N-IIb) are the same.

Provided herein are also methods for producing 2,2'-(furan-2,5-diyl)dialkanamines and 2,2'-(tetrahydrofuran-2,5-diyl)dialkanamines from 5-(haloalkyl)furfurals and 2-(haloalkyl)-5-(2-nitrovinyl)furans. Thus, in one aspect, provided is a method that includes: reducing a furan of formula (N) to produce a furan of formula (N-IIa) or a tetrahydrofuran of formula (N-IIb). In some embodiments, provided is a method that includes: converting a furan of formula (M) to a furan of formula (N) by a nitro-aldol reaction; and reducing the furan of formula (N) to produce a furan of formula (N-IIa) or a tetrahydrofuran of formula (N-IIb), or a combination thereof. In some variations of the nitro-aldol reaction, the furan of formula (M) may be combined with a nitroalkane of formula (I):

$$(R^xCH_2)NO_2 \qquad (I),$$

to produce the furan of formula (N). In some variations, the furan of formula (M) and the nitroalkane of formula (I) may be combined in the presence of a base and optionally solvent to produce the furan of formula (N).

In certain embodiments, provided is a method that includes: combining a furan of formula (A) with a compound of formula (II) having the structure of either N≡CH or N≡C$^-$ to produce a furan of formula (M); converting the furan of formula (M) to a furan of formula (N) by a nitro-aldol reaction as described above and in further detail herein; and reducing the furan of formula (N) to produce a furan of formula (N-IIa) or a furan of formula (N-IIb), or a combination thereof.

In some variations, $R^1$ and $R^2$ are H. Thus, in some variations, the furan of formula (A) is:

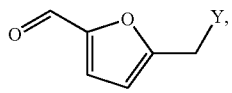

wherein Y is halo.

In some variations, the furan of formula (M) is:

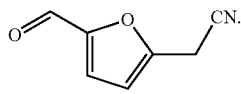

In some variations, the compound of formula (N) is:

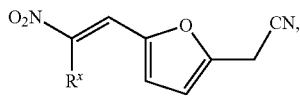

wherein $R^x$ is H or alkyl.

In some variations, the compound of formula (N-IIa) is:

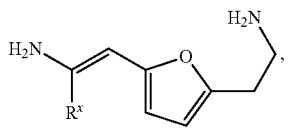

wherein $R^x$ is H or alkyl.

In some variations, the compound of formula (N-IIb) is:

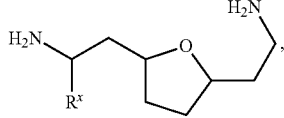

wherein $R^x$ is H or alkyl.

In some variations of the compounds of formula (A), $R^1$ and $R^2$ are H, and Y is chloro. Thus, in some variations, the compound of formula (A) is:

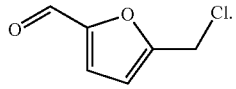

In other embodiments, Y is bromo, fluoro, or iodo.

In some variations of the compounds of formulae (N), (N-IIa), and (N-IIb), $R^1$, $R^2$, and $R^x$ are H. Thus, in some variations:

the compound of formula (N) is:

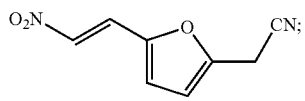 [SMILES: N#CCc1ccc(/C=C/[N+](=O)[O-])o1]

the compound of formula (N-IIa) is:

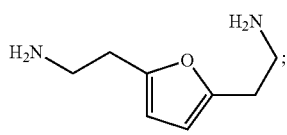 [SMILES: NCCc1ccc(CCN)o1]

and
the compound of formula (N-IIb) is:

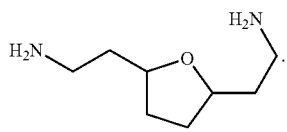

In other variations of the compounds of formulae (N), (N-IIa) and (N-IIb), $R^x$ is alkyl. In certain variations of the compounds of formulae (N), (N-IIa) and (N-IIb), $R^x$ is $C_{1-20}$ alkyl, or $C_{1-10}$ alkyl, or $C_{1-5}$ alkyl. In certain variations, $R^x$ is methyl, ethyl, propyl or butyl.

For example, with reference to FIG. 2, process 200 depicts an exemplary pathway to produce 2,2'-(furan-2,5-diyl)diethanamine (an example of a compound of (N-IIa)) and 2,2'-(tetrahydrofuran-2,5-diyl)diethanamine (an example of a compound of formula (N-IIb)) from 5-(chloromethyl)furfural (an example of a compound of formula (A)). In the first step of process 200, 5-(chloromethyl) furfural is combined with N≡CH or N≡C⁻ to produce 2-(5-formylfuran-2-yl)acetonitrile (an example of a compound of formula (M)). The 2-(5-formylfuran-2-yl)acetonitrile can undergo a nitro-aldol reaction to produce 2-(5-(2-nitrovinyl) furan-2-yl)acetonitrile (an example of a compound of formula (N)). As depicted in FIG. 2, the 2-(5-formylfuran-2-yl)acetonitrile may be combined with a nitroalkane, such as $CH_3NO_2$ (an example of a compound of formula (I)) in the presence of a base and solvent to produce the 2-(5-(2-nitrovinyl)furan-2-yl)acetonitrile, which can then be reduced to produce 2,2'-(furan-2,5-diyl)diethanamine (an example of a compound of formula (N-IIa)) and 2,2'-(tetrahydrofuran-2,5-diyl)diethanamine (an example of a compound of formula (N-IIb)).

It should be understood that the N≡CH or N≡C⁻ may be added to the reaction mixture, or generated in situ. It should also be understood that while process 200 of FIG. 2 depicts the (E)-isomer of 2-(5-(2-nitrovinyl)furan-2-yl)acetonitrile (an example of a compound of formula (N)), the compound of formula (N) may be the (E)-isomer, the (Z)-isomer, or a mixture thereof.

It should further be understood that while process 200 of FIG. 2 depicts the production of a mixture of a furan of formula (N-IIa) and a tetrahydrofuran of formula (N-IIb), in some embodiments only a furan of formula (N-IIa) is produced, while in other embodiments only a tetrahydrofuran of formula (N-IIb) is produced.

In another aspect, provided is a method that includes: combining a furan of formula (R) with a compound of formula (II) having the structure of either N≡CH or N≡C⁻ to produce a furan of formula (N); and reducing the furan of formula (N) to produce a furan of formula (N-IIa) or a tetrahydrofuran of formula (N-IIb), or a combination thereof.

In some variations, the compound of formula (R) is:

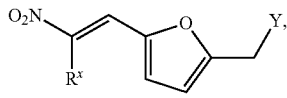

wherein R$^x$ is H or alkyl, and Y is halo.

In some variations of the compound of formula (R), Y is chloro. In other variations, Y is bromo, fluoro, or iodo. In some variations of the compound of formula (R), R$^x$ is H. In other variations of the compound of formula (R), R$^x$ is alkyl. In certain variations of the compound of formula (R), R$^x$ is C$_{1-20}$ alkyl, or C$_{1-10}$ alkyl, or C$_{1-5}$ alkyl. In certain variations, R$^x$ is methyl, ethyl, propyl or butyl.

In one variation of the compound of formula (R), Y is chloro, and R$^1$, R$^2$, and R$^x$ are H. Thus, in one variation, the compound of formula (R) is:

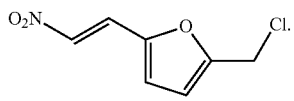 [SMILES: O=[N+]([O-])/C=C/c1ccc(CCl)o1]

For example, with reference again to FIG. 2, process 210 depicts another exemplary pathway to produce 2,2'-(furan-2,5-diyl)diethanamine (an example of a compound of formula (N-IIa)) and 2,2'-(tetrahydrofuran-2,5-diyl)diethanamine (an example of a compound of formula (N-IIb)) from 2-(chloromethyl)-5-(2-nitrovinyl)furan (an example of a compound of formula (R)). In the first step of process 210, 2-(chloromethyl)-5-(2-nitrovinyl)furan is combined with N≡CH or N≡C⁻ (examples of a compound of formula (II)) to produce 2-(5-(2-nitrovinyl)furan-2-yl)acetonitrile (an example of a compound of formula (N)), which may be reduced to produce 2,2'-(furan-2,5-diyl)diethanamine and 2,2'-(tetrahydrofuran-2,5-diyl)diethanamine.

It should be understood that the N≡CH or N≡C⁻ may be added to the reaction mixture, or generated in situ. It should also be understood that while process 210 in FIG. 2 depicts the (E)-isomer of 2-(5-(2-nitrovinyl)furan-2-yl)acetonitrile (an example of a compound of formula (N), the compound of formula (N) may be the (E)-isomer, the (Z)-isomer, or a mixture thereof. It should further be understood that while process 210 in FIG. 2 depicts the production of a mixture of a furan of formula (N-IIa) and a tetrahydrofuran of formula (N-IIb), in some embodiments only a furan of formula (N-IIa) is produced, while in other embodiments only a tetrahydrofuran of formula (N-IIb) is produced.

Compounds of Formula (P)

In other aspects, provided herein are (phenylene)dialkanamine compounds of formula (P):

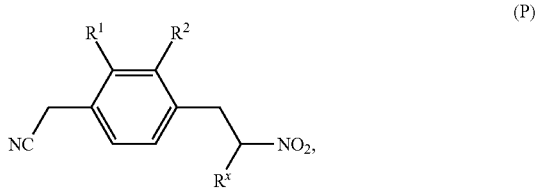

wherein:
R$^1$, R$^2$, and R$^x$ are independently H or alkyl.

In some variations, R$^x$ is H. In other variations, R$^x$ is alkyl. In certain variations, R$^x$ is C$_{1-20}$ alkyl, or C$_{1-10}$ alkyl, or C$_{1-5}$ alkyl. In some variations, R$^x$ is methyl, ethyl, propyl or butyl.

In some variations, R$^1$ and R$^2$ are both H. In other variations, at least one of R$^1$ and R$^2$ is alkyl. For example, in some variations, R$^1$ is H and R$^2$ is alkyl. In other variations R$^1$ is alkyl and R$^2$ is H. In yet other variations, both R$^1$ and R$^2$ are independently alkyl. In certain variations, R$^1$ and R$^2$ are independently H or C$_{1-20}$ alkyl, C$_{1-10}$ alkyl, or C$_{1-5}$ alkyl. In other variations, R$^1$ and R$^2$ are independently H or methyl, ethyl, propyl or butyl.

It should be generally understood that any of the variations for the R$^x$, R$^1$, and R$^2$ described herein may be combined the same as if each and every combination for the variables were specifically and individually listed.

For example, in certain embodiments, R$^1$ and R$^2$ are H, and the compound of formula (P) is:

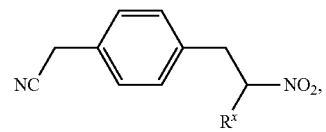

wherein R$^x$ is H or alkyl.

In other embodiments, R$^x$, R$^1$ and R$^2$ are all H, and the compound of formula (P) is:

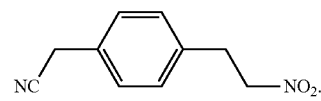

In yet other embodiments, R$^x$ is methyl, R$^1$ and R$^2$ are both H, and the compound of formula (P) is:

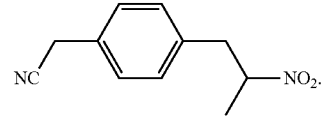

Methods of Producing Compounds of Formula (P)

Figure 3:
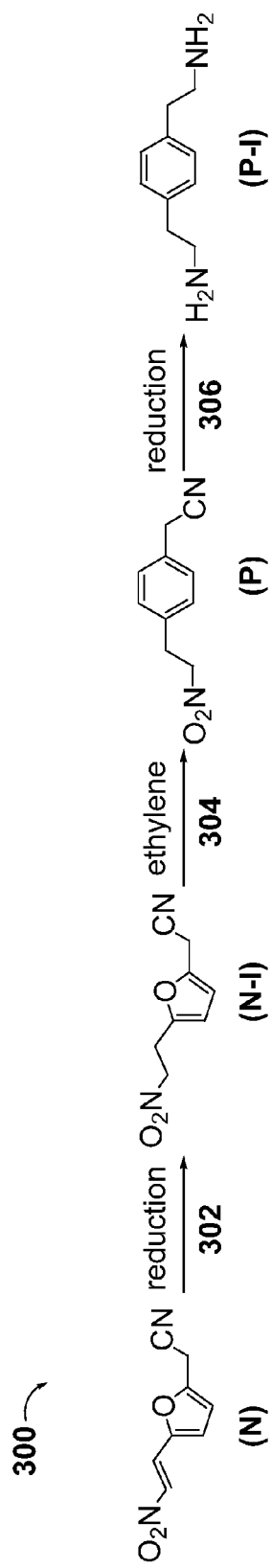
FIG. 3 depicts an exemplary process to produce 2-(5-(2-nitroethyl)furan-2-yl)acetonitrile, 2-(4-(2-nitroethyl)phenyl)acetonitrile, and 2,2'-(1,4-phenylene)bis(ethan-1-amine) from 2-(5-(2-nitrovinyl)furan-2-yl)acetonitrile.

In certain aspects, provided herein are also methods of producing (phenylene)dialkanamine compounds, including, for example, the compounds of formula (P). With reference to FIG. 3, process 300 depicts an exemplary pathway to produce a compound of formula (P). In process 300, a nitroalkyl(furan)nitrile of formula (N-I) undergoes a Diels-Alder reaction with ethylene in step 304 to produce compound of formula (P), wherein the furan of formula (N-I) is as described above. It should be understood that while process 300 depicts compounds of formulae (N-I) and (P) in which R$^1$ and R$^2$ are both H, in some variations of process 300, at least one of R$^1$ and R$^2$ are alkyl. In other variations, both R$^1$ and R$^2$ are alkyl.

Variations of the methods of producing (phenylene)dialkanamine compounds, including, for example, the compounds of formula (P), are exemplified in General Reaction Scheme P described below.

General Reaction Scheme P

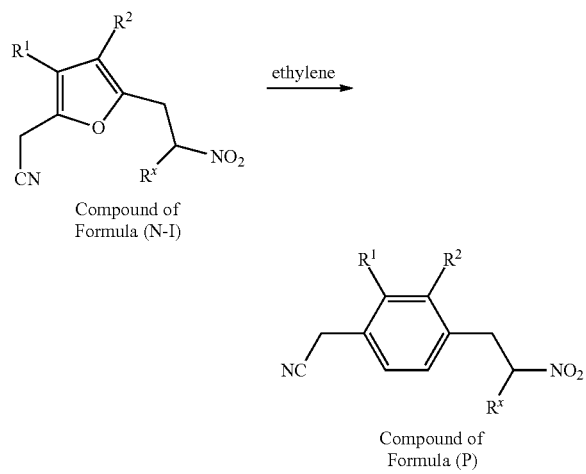

Compound of Formula (N-I)

Compound of Formula (P)

General Reaction Scheme P depicts an exemplary reaction to convert a compound of formula (N-I), wherein $R^1$, $R^2$, and $R^x$ are independently H or alkyl, to a compound of formula (C), wherein $R^1$, $R^2$, and $R^x$ are independently H or alkyl, by Diels-Alder reaction with ethylene.

In some variations of the reaction depicted in General Reaction Scheme P, the compound of formula (N-I) is reacted with ethylene at an initial ethylene pressure of between 800 psia to 1500 psia. In certain variations, the initial ethylene pressure is 1000 psia. In some variations of the reaction depicted in General Reaction Scheme P, the compound of formula (N-I) is reacted with ethylene at an initial ethylene pressure of between 800 psi to 1500 psi. In certain variations, the initial ethylene pressure is 1000 psi. In some variations, the compound of formula (N-I) is reacted with ethylene in the additional presence of solvent. In certain embodiments, the ethylene may be dissolved, or at least partially dissolved, in one or more solvents. In other variations, the compound of formula (N-I) is reacted with ethylene to produce the compound of formula (P), wherein the ethylene may also be provided at supercritical pressures and/or supercritical temperatures.

In some variations of the reaction depicted in General Reaction Scheme C, the compound of formula (N-I) is reacted with ethylene in the presence of a catalyst to produce the compound of formula (P). Any suitable catalyst may be used. For example, the catalysts may be selected from one or more classes of catalysts, including (i) metal-containing catalysts, including metal-containing salts that are catalytic or may convert in situ into a catalytic species, and (ii) acids (e.g., Lewis acids, weak acids, sulfonic acids, and heteropolyacids). In some embodiments, the catalyst is a metal triflate. In one embodiment, the catalyst is triflic acid.

In some variations, the compound of formula (N-I) is converted to a compound of formula (P) by Diels-Alder reaction with ethylene at a temperature between 250° C. to 350° C. In one embodiment, the temperature is 300° C.

Thus, in certain aspects, provided herein are methods of producing a compound of formula (P) by:
combining the furan of formula (N-I) with ethylene to produce a compound of formula (P).

It should be understood that when the compound of formula (N-I) is used to produce the compound of formula (P), $R^1$, $R^2$, and $R^x$ in formulae (N-I) and (P) are the same.

Compounds of Formula (P-I)

In other aspects, provided herein are (phenylene)dialkanamine compounds of formula (P-I):

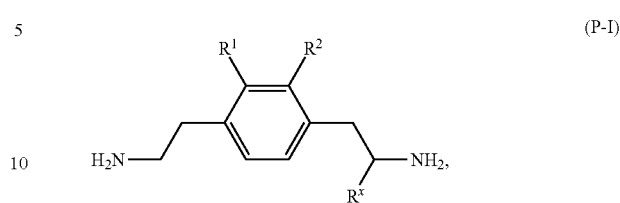

wherein:
$R^1$, $R^2$, and $R^x$ are independently H or alkyl.
In some variations, $R^x$ is H. In other variations, $R^x$ is alkyl. In certain variations, $R^x$ is $C_{1-20}$ alkyl, or $C_{1-10}$ alkyl, or $C_{1-5}$ alkyl. In some variations, $R^x$ is methyl, ethyl, propyl or butyl.

In some variations, $R^1$ and $R^2$ are both H. In other variations, at least one of $R^1$ and $R^2$ is alkyl. For example, in some variations, $R^1$ is H and $R^2$ is alkyl. In other variations $R^1$ is alkyl and $R^2$ is H. In yet other variations, both $R^1$ and $R^2$ are independently alkyl. In certain variations, $R^1$ and $R^2$ are independently H or $C_{1-20}$ alkyl, $C_{1-10}$ alkyl, or $C_{1-5}$ alkyl. In other variations, $R^1$ and $R^2$ are independently H or methyl, ethyl, propyl or butyl.

It should be generally understood that any of the variations for the $R^x$, $R^1$, and $R^2$ described herein may be combined the same as if each and every combination for the variables were specifically and individually listed.

For example, in certain embodiments, $R^1$ and $R^2$ are H, and the compound of formula (P-I) is:

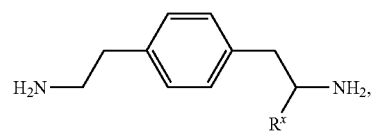

wherein $R^x$ is H or alkyl.
In other embodiments, $R^x$, $R^1$ and $R^2$ are all H, and the compound of formula (P-I) is:

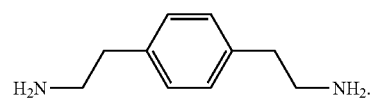

In yet other embodiments, $R^x$ is methyl, $R^1$ and $R^2$ are both H, and the compound of formula (P-I) is:

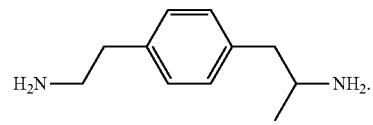

Methods of Producing Compounds of Formula (P-I)

In certain aspects, provided herein are also methods of producing (phenylene)dialkanamine compounds, including, for example, the compounds of formula (P-I).

For example, process 300 (FIG. 3) depicts an exemplary pathway to produce (phenylene)dialkanamines of formula (P-I) from furans of formula (P) in step 306.

Variations of the methods of producing (phenylene)dialkanamine compounds, including, for example, the compounds of formula (P-I), are exemplified in General Reaction Scheme P-I described below.

General Reaction Scheme P-I

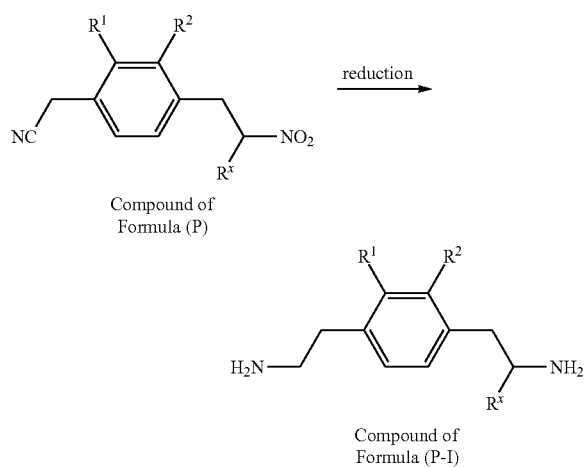

Compound of
Formula (P)

Compound of
Formula (P-I)

Depicted in General Reaction Scheme P is an exemplary reaction to produce a compound of formula (P-I). In the exemplary reaction, a compound of formula (P), wherein $R^1$, $R^2$, and $R^x$ are independently H or alkyl, is reduced to produce a compound of formula (P-I), wherein $R^1$, $R^2$, and $R^x$ are independently H or alkyl.

In some variations of the reaction depicted in General Reaction Scheme P-I, the compound of formula (P) is reduced in the presence of hydrogen to produce the compound of formula (P-I). The hydrogen may be provided in the form of hydrogen gas or by transfer hydrogenation (e.g., by addition of cyclohexene or cyclohexadiene to the reaction mixture as the hydrogen source).

In one variation, the compound of formula (P) is reduced at a pressure of at least 1 psi, or at least 10 psi; or between 1 psi and 1500 psi, between 1 psi and 1000 psi, between 500 psi and 1500 psi, between 1 psi and 50 psi, between 1 psi and 100 psi, between 1 psi and 80 psi, between 1 psi and 75 psi, or between 30 psi and 60 psi to produce the compound of formula (P-I). It should be understood that the hydrogen gas may be dissolved, or at least partially dissolved, in the reagents and/or other solvents described herein.

In some variations, the furan of formula (P) is reduced in the presence of hydrogen and catalyst to produce the compound of formula (P-I). Any suitable catalyst may be used.

In certain variations, the catalyst includes a metal. In certain variations, the catalyst includes palladium, platinum, rhodium, rhenium, or a combination thereof. In one variation, the catalyst includes palladium, platinum, or a combination thereof. For example, the catalyst may be palladium on carbon (Pd/C) or platinum on carbon (Pt/C). In another variation, the catalyst includes rhodium, rhenium, or a combination thereof. For example, the catalyst may be Rh—Re/SiO$_2$.

In some variations, the catalyst further includes a solid support. In certain variation, the catalyst includes a solid acid support. For example, in one variation, the catalyst may include fluorosulfonic acid polymer on amorphous silica (e.g., Nafion® SAC-13).

In some variations, the compound of formula (P) is reduced to produce the compound of formula (P-I) at a temperature between 0° C. to 100° C. In certain variations, the compound of formula (P) is reduced to produce the compound of formula (P-I) at a temperature between 10° C. to 60° C. In one variation, the compound of formula (P) is reduced to produce the compound of formula (P-I) at 50° C.

Thus, in one aspect, provided is a method that includes: reducing a compound of formula (P) to produce a (phenylene)dialkanamine of formula (P-I).

As described above, compounds of formula (P) may be produced from compounds of formula (N-I), which may be produced from compounds of formula (N). Thus, in one aspect, provided herein is a method that includes: reducing a furan of formula (N) to produce a furan of formula (N-I); converting the furan of formula (N-I) to a compound of formula (P) through Diels-Alder reaction with ethylene; and reducing the compound of formula (P) to produce a compound of formula (P-I). In some variations, the furan of formula (M) may be combined with a nitroalkane of formula (I):

$$(R^xCH_2)NO_2 \qquad (I),$$

to produce the furan of formula (N). In some variations, the furan of formula (M) and the nitroalkane of formula (I) may be combined in the presence of a base and optionally solvent to produce the furan of formula (N). Any of the compounds of formulae (N), (N-I), (M), or (P) described above may be used to produce a compound of formula (P-I).

In some variations, $R^1$ and $R^2$ are both H. Thus, in some variations, the furan of formula (N) is:

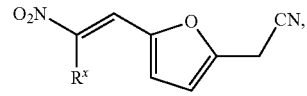

wherein $R^x$ is H or alkyl.
In some variations, the furan of formula (N-I) is:

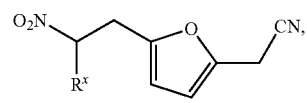

wherein $R^x$ is H or alkyl.
In some variations, the compound of formula (P) is:

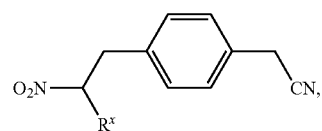

wherein $R^x$ is H or alkyl.
In some variations, the compound of formula (P-I) is:

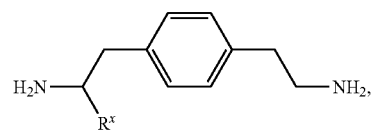

wherein $R^x$ is H or alkyl.

It should be understood that when the compound of formula (N) is used to produce a furan of formula (N-I), a compound of formula (P), or a compound of formula (P-I), $R^1$, $R^2$, and IV in formulae (N), (N-I), (P) and (P-I) are the same.

In some variations of the compounds of formulae (N), (N-I), (P) and (P-I), $R^1$, $R^2$, and IV are H. Thus, in some variations:

the compound of formula (N) is:

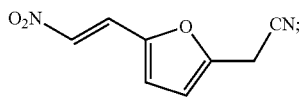 [SMILES: N#CCc1ccc(/C=C/[N+](=O)[O-])o1]

the compound of formula (N-I) is:

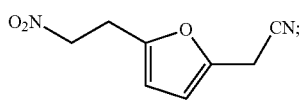 [SMILES: N#CCc1ccc(CC[N+](=O)[O-])o1]

the compound of formula (P) is:

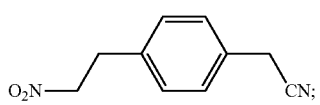

and
the compound of formula (P-I) is:

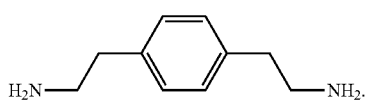

In other variations of the compounds of formulae (N), (N-I), (P) and (P-I), $R^x$ is alkyl. In certain variations of the compounds of formulae (N), (N-I), (P) and (P-I), $R^x$ is $C_{1-20}$ alkyl, or $C_{1-10}$ alkyl, or $C_{1-5}$ alkyl. In certain variations, $R^x$ is methyl, ethyl, propyl or butyl.

For example, with reference to FIG. 3, process 300 depicts an exemplary pathway to produce 2,2'-(1,4-phenylene)bis(ethan-1-amine) (an example of a compound of formula (P-I)) from (E)-2-(5-(2-nitrovinyl)furan-2-yl)acetonitrile (an example of a compound of formula (N)). In the first step of process 300, (E)-2-(5-(2-nitrovinyl)furan-2-yl) acetonitrile is reduced to produce 2-(5-(2-nitroethyl)furan-2-yl)acetonitrile (an example of a compound of formula (N-I)). The 2-(5-(2-nitroethyl)furan-2-yl)acetonitrile can undergo a Diels-Alder reaction with ethylene to produce 2-(4-(2-nitroethyl)phenyl)acetonitrile (an example of a compound of formula (P)). The 2-(4-(2-nitroethyl)phenyl)acetonitrile can then be reduced to produce 2,2'-(1,4-phenylene)bis(ethan-1-amine).

It should be understood that while FIG. 3 depicts the (E)-isomer of 2-(5-(2-nitrovinyl)furan-2-yl)acetonitrile (an example of a compound of formula (N)), the compound of formula (N) may be the (E)-isomer, the (Z)-isomer, or a mixture thereof.

With reference to FIG. 1, (phenylene)dialkanamines of formula (P-I), (furan)dialkanamines of formula (B-IIa), (tetrahydrofuran)dialkanamines of formula (B-IIb), and alkyldiamines of formula (B-III) may be produced from furans of formula (B) by various pathways.

Each of the steps in exemplary processes 100, 110, 120, 200, 210, 300 and 400 are described in further detail below.

I. Reduction Reactions

With reference again to FIG. 1, the exemplary furan of formula (B) depicted in process 100 may be reduced to produce a furan of formula (B-I) (step 102 of process 100), a furan of formula (B-IIa) and/or a tetrahydrofuran of formula (B-IIb) (step 112 of process 110), or any alkyldiamine of formula (B-III) (process 120), or a combinations thereof. The furan of formula (C) may be reduced to produce a furan of formula (C-I) (step 106 of process 100).

With reference again to FIG. 2, the exemplary furan of formula (N) depicted in process 200 and process 210 may be reduced to produce a furan of formula of (N-IIa), a furan of formula (N-IIb), or a combination thereof.

With reference again to FIG. 3, the exemplary furan of formula (N) depicted in process 300 may be reduced to produce a furan of formula (N-I) (step 302 of process 300), and the compound of formula (P) may be reduced to produce a compound of formula (P-I) (step 306 of process 300).

a) Hydrogen

In some variations, the compounds of formulae (B), (C), (N), and (P) may be reduced in the presence of hydrogen. The hydrogen may be provided in the form of hydrogen gas or by transfer hydrogenation (e.g., by addition of cyclohexene or cyclohexadiene to the reaction mixture as the hydrogen source).

In certain variations, the compound of formula (B) is reduced to produce the compounds of formulae (B-I), (B-IIa), (B-IIb) or (B-III), or any mixtures thereof, in the presence of hydrogen gas. In certain variations, the compound of formula (C) is reduced to produce the compound of formula (C-I) in the presence of hydrogen gas. In certain variations, the compound of formula (N) is reduced to produce compounds of formulae (N-I), (N-IIa) or (N-IIb), or any mixtures thereof, in the presence of hydrogen gas. In certain variations, the compound of formula (P) is reduced to produce the compound of formula (P-I) in the presence of hydrogen gas.

In some variations, the compounds of formulae (B), (C), (N), and (P) are reduced at a pressure of at least 1 psi, or at least 10 psi; or between 1 psi and 1500 psi, between 1 psi and 1000 psi, between 500 psi and 1500 psi, between 1 psi and 50 psi, between 1 psi and 100 psi, between 1 psi and 80 psi, between 1 psi and 75 psi, or between 30 psi and 60 psi. In some variations the compounds of formulae (B), (C), (N), and (P) are reduced at a pressure between 10 to 100 psig, between 10 to 75 psig, between 10 to 350 psig, or at about 300 psig.

It should be understood that the hydrogen gas may be dissolved, or at least partially dissolved, in the reagents and/or other solvents described herein.

The reduction reactions as described herein may be carried out at any suitable temperature. In some variations, the reduction is performed between 50° C. and 500° C., between 100° C. and 400° C., between 200° C. and 300° C., between 300° C. and 400° C., or between 100° C. and 200° C.

b) Catalysts

In some variations, the compounds of formulae (B), (C), (N), and (P) may be reduced in the presence of a reducing agent and catalyst. In some variations, the reducing agent is hydrogen or a hydrogen donor.

In certain variations, the catalyst comprises a metal. In certain variations, the catalyst comprises palladium, platinum, rhodium, nickel, copper, cobalt, zinc, iridium, rhenium, aluminum or zinc, or any combinations thereof. In one variation, the catalyst comprises palladium or platinum, or a combination thereof. In certain variations, the catalyst comprises two metals. In some variations, the catalyst comprises a bimetal. In certain variations, the catalyst is a bimetallic catalyst. In some variations, the catalyst further comprises sulfur or phosphorous, or a combination thereof.

For example, the catalyst may be palladium on carbon (Pd/C) or platinum on carbon (Pt/C). In another variation, the catalyst comprises rhodium, rhenium, or a combination thereof. For example, the catalyst may be Rh—Re/$SiO_2$, Pd/Ir, Pd/Rh, Raney Nickel, Ni—Co, copper chromite, or sulfide nickel.

In some variations, the catalyst further includes a solid support. In some embodiments, the solid support is a metal oxide, a polymer, or carbon, or a combination thereof. In certain embodiments, the solid support is zinc oxide, silica, or alumina, or a combination thereof. In certain variations, the catalyst includes a solid acid support. For example, in one variation, the catalyst may include fluorosulfonic acid polymer on amorphous silica (e.g., Nafion® SAC-13).

In some variations, the compounds of formulae (B), (C), (N), and (P) may be reduced in the further presence of an amine compound, a diamine compound, a phosphine compound, a phosphite compound, or a diphosphine compound, or combinations thereof. In some variations, the compounds may be reduced in the presence of an aqueous alkali solution, for example an aqueous solution of LiOH, NaOH, KOH, RbOH or CsOH, or any combinations thereof.

II. Diels-Alder Reactions

With reference again to FIG. 1, the furan of formula (B-I) may undergo a Diels-Alder reaction with ethylene to produce a compound of formula (C) (step 104 in process 100). Similarly, the furan of formula (B-IIa) may undergo a Diels-Alder reaction with ethylene to produce a compound of formula (C-I) (step 110 in process 110).

With reference again to FIG. 3, the furan of formula (N-I) may undergo a Diels-Alder reaction with ethylene to produce a compound of formula (P) (step 304 in process 300).

Thus, in some variations, the methods include combining a furan of formula (B-I) with ethylene and catalyst to form a reaction mixture; and producing a compound of formula (C) from at least a portion of the furan of formula (B-I) and ethylene in the reaction mixture. In certain variations, the method further includes combining the furan of formula (B-I), the ethylene, the catalyst with a solvent to form the reaction mixture. In yet other variations, the method further includes isolating the compound of formula (C) from the reaction mixture. In yet other variations, the method further includes purifying the compound of formula (C).

In some variations, the method includes combining a furan of formula (B-IIa) with ethylene and catalyst to form a reaction mixture; and producing a compound of formula (C-I) from at least a portion of the furan of formula (B-IIa) and ethylene in the reaction mixture. In certain variations, the method further includes combining the furan of formula (B-IIa), the ethylene, the catalyst with a solvent to form the reaction mixture. In yet other variations, the method further includes isolating the compound of formula (C-I) from the reaction mixture. In yet other variations, the method further includes purifying the compound of formula (C-I).

In some variations, the method includes combining a furan of formula (N-I) with ethylene and catalyst to form a reaction mixture; and producing a compound of formula (P) from at least a portion of the furan of formula (N-I) and ethylene in the reaction mixture. In certain variations, the method further includes combining the furan of formula (N-I), the ethylene, the catalyst with a solvent to form the reaction mixture. In yet other variations, the method further includes isolating the compound of formula (P) from the reaction mixture. In yet other variations, the method further includes purifying the compound of formula (P).

The ethylene, catalyst and solvent used in the Diels-Alder reaction are described in further detail below.

a) Ethylene

The ethylene used in the methods described herein may be obtained from any source (including any commercially available sources). For example, ethylene can be obtained from fossil fuel sources or renewable sources, such as by dehydration of ethanol (e.g., fermentation-based ethanol).

The ethylene used in the methods described herein may be added using any suitable methods or techniques to the reactor. For example, in certain embodiments, ethylene may be added as a gas into the reactor.

The initial ethylene pressure refers to the pressure at which ethylene (as a gas) is added to the reactor. The ethylene may be added at an initial pressure such that the concentration of this reactant is sufficiently high in the solvent for optimal reaction rates. In some embodiments, the initial ethylene pressure is at least 10 psi, at least 50 psi, at least 75 psi, at least 100 psi, at least 200 psi, at least 250 psi, at least 300 psi, or at least 400 psi. In certain embodiments, the initial ethylene pressure is between 50 psi and 20,000 psi, or between 100 psi and 20,000 psi, or between 300 psi and 20,000 psi, or between 400 psi and 1,000 psi, or between 400 psi and 800 psi, between 600 psi and 1000 psi, between 600 and 6000 psi, or between, between 760 psi and 6000 psi, or between 1000 psi to 6000 psi.

In other embodiments, ethylene may be dissolved, or at least partially dissolved, in one or more solvents described herein and added to the reactor. In certain embodiments, the ethylene solubility in the solvent is between about 0 mol/L and about 0.82 mol/L, between about 0.82 mol/L and about 1.2 mol/L, or between about 1.2 mol/L and about 4.0 mol/L, when ethylene solubility is measured at temperature of about 23° C.

The ethylene may also be provided at supercritical pressures and/or supercritical temperatures.

b) Catalysts

Various catalysts may be used in the methods described herein (e.g., for the Diels-Alder reaction). For example, the catalysts may be selected from one or more classes of catalysts, including (i) metal-containing catalysts, including metal-containing salts that are catalytic or may convert in situ into a catalytic species, and (ii) acids (e.g., Lewis acids, weak acids, sulfonic acids, and heteropolyacids).

It should be understood, however, that the catalyst may fall into one or more classes listed herein. For example, the catalyst may be copper triflate, which is a metal-containing catalyst and also a Lewis acid. The catalyst may also be supported or unsupported. The catalyst may also be homogeneous or heterogeneous based on the solvent used in the reaction. The catalysts may also be in the form of a solvate, including, for example, a hydrate. The catalysts may also be a polymer.

It should also be understood that the catalyst increases the rate of the chemical reaction, and such increase may be caused directly or indirectly (e.g., by conversion in situ into a different catalyst species). For example, the catalyst used may be copper triflate. Without wishing to be bound by any theory, under certain reaction conditions, the copper triflate may yield triflic acid, which may contribute to the increase in rate of the chemical reaction. In another example, the catalyst used may be triflimide. In another example, without wishing to be bound by any theory, the triflimide may yield triflic acid in the reaction mixture, which may contribute to the increase in rate of the chemical reaction.

The catalysts provided for the methods described herein may be obtained from any sources (including any commercially available sources), or may be prepared by any methods or techniques known in the art. It should also be understood that providing a catalyst includes providing the catalyst itself, or a precursor that forms a catalytic species (e.g., in situ) that may contribute to the increase in rate of the chemical reaction.

Metal Catalysts

In some embodiments, the catalyst is a metal catalyst. A metal catalyst can be any catalyst that is a metal or contains a metal ligand. The metals may include, for example, alkali metals, alkali earth metals, transition metals or lanthanides. In one embodiment, the metals may include transition metals or lanthanides. In certain embodiments, the metal is selected from Group 3, Group 9, Group 10, Group 11, and the lanthanide series. In certain embodiments, the metal is selected from Group 3, Group 9, Group 11, and the lanthanide series.

In some embodiments, the metal is aluminum, bismuth, copper, chromium, iron, gadolinium, indium, nickel, neodymium, lithium, sodium, potassium, rubidium, cesium, beryllium, magnesium, calcium, strontium, barium, lanthanum, scandium, titanium, vanadium, yttrium, zinc, platinum, palladium, silver, gold, thallium, rhenium, mercury, tin, boron, gallium, lead, cobalt, germanium, and cerium.

Without wishing to be bound by any theory, under certain conditions, the catalytic species in the reactions described herein may also be formed in situ by providing suitable precursors. For example, copper metal and chlorine gas may be provided to the reaction to produce copper chloride in situ. It should also be understood that the catalytic species may be formed in situ by reaction between the metal precursor and the ethylene provided in the reaction. For example, under certain conditions, copper triflate is provided to the reaction, and may form a catalytic species with ethylene.

In one embodiment, the metal catalyst is a metal-containing catalyst. Metal-containing catalysts have one or more metal cations and one or more counterions or ligands. For example, the catalyst may be a metal-centered catalyst. In certain embodiments, the metal cation in a metal-containing catalyst may be a transition metal cation or a lanthanide cation. In certain embodiments, the metal cation in a metal-containing catalyst is selected from Group 3, Group 9, Group 10, Group 11, and the lanthanide series. In certain embodiments, the metal cation is selected from Group 3, Group 9, Group 11 and or the lanthanide series. In one embodiment, the metal cation is a Group 11 cation. It should be understood that the group number used for the metals follow the IUPAC or long-form nomenclature, which is well-known in the art.

In some embodiments, the catalyst may have a monovalent metal cation. For example, in certain embodiments, the monovalent metal cation is $Cu^+$, $Li^+$, $Na^+$, $K^+$, $Rb^+$, $Cs^+$, $Ag^+$, $Tl^+$, or $Hg_2^{2+}$. In one embodiment, the monovalent metal cation is $Cu^{1+}$.

In other embodiments, the catalyst may have a divalent metal cation or a trivalent metal cation. For example, in some embodiments, the divalent metal cation is $Cu^{2+}$, $Ni^{2+}$, $Be^{2+}$, $Mg^{2+}$, $Ca^{2+}$, $Sr^{2+}$, $Ba^{2+}$, $Zn^{2+}$, $Pt^{2+}$, $Pd^{2+}$, $Hg^{2+}$, $Sn^{2+}$, $Pb^{2+}$, $Co^{2+}$, or $Ge^{2+}$. In certain embodiments, the divalent metal cation is $Cu^{2+}$, $Co^{2+}$, $Cr^{3+}$, $Ni^{2+}$, $Mg^{2+}$, or $Zn^{2+}$. In certain embodiments, the divalent metal cation is $Cu^{2+}$, $Co^{2+}$, $Ni^{2+}$, or $Zn^{2+}$. In one embodiment, the divalent metal cation is $Cu^{2+}$, $Co^{2+}$, or $Zn^{2+}$. In one embodiment, the divalent metal cation is $Cu^{2+}$.

In some embodiments, the trivalent metal cation is $Al^{3+}$, $Bi^{3+}$, $Cr^{3+}$, $Fe^{3+}$, $Gd^{3+}$, $In^{3+}$, $Nd^{3+}$, $La^{3+}$, $Sc^{3+}$, $Y^{3+}$, $Au^{3+}$, $Tl^{3+}$, $Re^{3+}$, $Sn^{3+}$, $B^{3+}$, $Ga^{3+}$, $Co^{3+}$, or $Ce^{3+}$. In certain embodiments, the trivalent metal cation is $Al^{3+}$, $Bi^{3+}$, $Fe^{3+}$, $Gd^{3+}$, $In^{3+}$, $Nd^{3+}$, $La^{3+}$, $Sc^{3+}$, or $Y^{3+}$. In certain embodiments, the trivalent metal cation is $Al^{3+}$, $Fe^{3+}$, $Gd^{3+}$, $In^{3+}$, $La^{3+}$, or $Y^{3+}$. In one embodiment, the trivalent metal cation is $Al^{3+}$, $Gd^{3+}$, $In^{3+}$, $La^{3+}$, or $Y^{3+}$. In another embodiment, the trivalent metal cation is $Gd^{3+}$, $In^{3+}$, $La^{3+}$, or $Y^{3+}$.

In yet other embodiments, the catalyst may have a tetravalent metal ion.

The metal cations may coordinate with one or more cations. For example, the divalent or trivalent metal cation of the catalyst may coordinate with two or three counterions, respectively. Each counterion may independently be selected from, for example, halides (e.g., chloride, bromide), triflates (—OTf), and carboxylates (e.g. formate, acetate, acetylacetonate). It should be understood, however, that any suitable counterion may be used. In one embodiment, the counterions may be chloride or triflate. It should be understood that the counterions may all be the same, the counterions may all be different, or two counterions may be the same and the third counterion may be different.

In some embodiments, the counterions may be ligands that coordinate with the metal. Ligands may be, cationic, anionic or neutral. For example, the catalyst may be $\eta^2$-ethylene-copper(II)triflate.

In some embodiments, the catalyst is aluminum chloride, aluminum bromide, aluminum triflate, bismuth chloride, bismuth bromide, bismuth triflate, copper chloride, copper bromide, copper triflate, cobalt chloride, cobalt bromide, cobalt triflate, chromium chloride, chromium bromide, chromium triflate, iron chloride, iron bromide, iron triflate, gadolinium chloride, gadolinium bromide, gadolinium triflate, indium chloride, indium bromide, indium triflate, nickel chloride, nickel bromide, nickel triflate, neodynium chloride, neodynium bromide, neodynium triflate, magnesium chloride, magnesium bromide, magnesium triflate, lanthanum chloride, lanthanum bromide, lanthanum triflate, scandium chloride, scandium bromide, scandium triflate, tin chloride, tin bromide, tin triflate, titanium chloride, titanium bromide, titanium triflate, vanadium chloride, vanadium bromide, vanadium triflate, yttrium chloride, yttrium bromide, yttrium triflate, zinc chloride, zinc bromide, zinc triflate, or any combinations thereof.

In certain embodiments, the catalyst is copper chloride, copper triflate, yttrium triflate, scandium triflate, lanthanum triflate, neodynium triflate, copper triflimide, or any combinations thereof. In other embodiments, the catalyst is aluminum chloride, copper chloride, copper triflate, yttrium triflate, or any combination thereof. In one embodiment, the catalyst is copper chloride or copper triflate, or a combination thereof. In another embodiment, the catalyst is copper (II) bis(trifluoromethylsulfonyl)imide (i.e., copper triflimide, also referred to as $Cu[N(Tf)_2]_2$).

In other embodiments, the catalyst is a metal-containing salt catalyst, including any such salts that may convert in situ into a species that is catalyst for the reactions described herein. For example, a metal salt catalyst may include a Group 11 metal with one or more counterion(s). The metal of the metal salt catalyst may be a copper cation. In one embodiment, the catalyst is copper acetate or copper acetylacetonate. As discussed above, any suitable counterions may be present in the metal-containing salt catalyst.

In certain embodiments, the catalyst comprises copper or a copper ion. In one embodiment, the catalyst comprises a copper (I) ion. In another embodiment, the catalyst comprises a copper (II) ion. In one embodiment, the catalyst is Cu[N(Tf)$_2$]$_2$, CuCl$_2$, Cu(OCOCH$_3$)$_2$, Cu(CH$_3$COCH$_2$COCH$_3$)$_2$, Cu(II)(BF$_4$)$_2$, Cu(I)(BF$_4$)(CH$_3$CN)$_4$, [Cu(I)OSO$_2$CF$_3$]$_2$C$_6$H$_6$, (Cu(I)OSO$_2$CF$_3$)(CH$_3$CN)$_4$, or any combination thereof. Such catalysts may be obtained from any commercially available source, or prepared by any suitable methods known in the art. Certain catalysts may also be formed in situ. For example, in one embodiment, copper metal may be provided as a precursor to generate CuCl$_2$ in situ. In another embodiment, copper oxide (Cu$_2$O) may be provided in combination with HBF$_4$ and CH$_3$CN to generate Cu(I)(BF$_4$)(CH$_3$CN)$_4$ in situ. In yet another embodiment, copper oxide (Cu$_2$O) may be provided in combination with CF$_3$SO$_3$H and CH$_3$CN to generate (Cu(I)OSO$_2$CF$_3$)(CH$_3$CN)$_4$ in situ.

Lewis Acids

In some embodiments, the catalyst is a Lewis acid. As used herein, a "Lewis acid" refers to an acid substance that can employ an electron lone pair from another molecule in completing the stable group of one of its own atoms.

It should be understood that one or more of catalysts (including the one or more the metal-containing catalysts) described above may be Lewis acids. For example, the catalyst may be a Lewis acid, such as aluminum chloride, zinc chloride, indium chloride, divalent transition metal ions of copper, nickel or cobalt or mixtures thereof such as CuCl$_2$ or CoCl$_2$, triflates such as the triflate of indium, copper, gadolinium or yttrium, trivalent metal ions from the lanthanide series of elements or mixtures thereof.

The catalyst may be a solvate, including hydrate, or anhydrous. For example, in one embodiment, the catalyst is CuCl$_2$×2H$_2$O. In another embodiment, the catalyst is CuCl$_2$, wherein less than 5%, less than 4%, less than 3%, less than 2%, or less than 1% of the catalyst is water.

In other embodiments, the catalysts may also include acetic acid, haloacetic acid (e.g., chloroacetic acid, dichloroacetic acid, trichloroacetic acid, fluoroacetic acid, and difluoroacetic acid, trifluoroacetic acid). These acids may be Lewis acids in the reaction. The acids may also be obtained from an anhydride that hydrolyzes into its corresponding acid form in the presence of water. For example, acetic anhydride may contain a small percentage of acetic acid, which acts as a catalyst for the reaction. Additionally, the acetic anhydride in the reaction mixture may further convert into acetic acid in the reaction.

Heteropolyacids

In other embodiments, the catalyst is a heteropolyacid. Heteropolyacids is a class of acids that includes a combination of hydrogen and oxygen atoms with certain metals and/or non-metals. The heteropolyacid typically includes at least one addenda atom, oxygen, a hetero atom, and acidic hydrogen atoms. In certain embodiments, the addenda atoms may be selected from one or more metals, including for example, tungsten, molybdenum, or vanadium. In certain embodiments, the hetero atom may be selected from p-block elements, such as silicon or phosphorous. It is understood that any description of the addenda atoms for the heteropolyacids for use in the methods described herein may be combined with any descriptions of the hetero atoms the same as if each and every combination were specifically and individually listed. Suitable heteropolyacids may include, for example, tungstosilicic acid, tungstophosphoric acid, molybdosilicic acid, molybdophosphoric acid. A mixture of heteropolyacids may also be used.

The heteropolyacids may have certain structures that are known in the art. In one embodiment, the heteropolyacid is a Keggin structure, having the formula H$_a$XM$_{12}$O$_{40}$, where X is the hetero atom, M is the addenda atom, and n is an integer greater than 0. In another embodiment, the heteropolyacid is a Dawson structure having the formula H$_n$X$_2$M$_{18}$O$_{62}$, where X is the hetero atom, M is the addenda atom, and n in an integer greater than 0.

In one embodiment, the catalyst is a heteropolyacid selected from 12-tungstophosphoric acid, 12-molybdophosphoric acid, 12-tungstosilicic acid, 12-molybdosilicic acid, and any combinations thereof.

In certain embodiments, the catalyst may be a solvate of a heteropolyacid. Suitable solvates may include hydrates or alcohol solvates.

In other embodiments that may be combined with any of the foregoing embodiments, the catalyst that is a heteropolyacid may be unsupported or supported. In one embodiment, the catalyst is a supported heteropolyacid. Suitable solid supports for the heteropolyacids may include, for example, carbon, alumina, silica, ceria, titania, zirconia, niobia, zeolite, magnesia, clays, iron oxide, silicon carbide, aluminosilicates, and any modifications, mixtures or combinations thereof.

Sulfonic Acids, Sulfonamides, and Sulfonimides

In some embodiments, the catalyst is a sulfonic acid, or a salt, ester, anhydride or resin thereof. Sulfonic acids used herein may have a structure of formula of R$^w$SO$_3$H. In certain embodiments, R$^w$ is alkyl, haloalkyl, cycloalkyl, heterocycloalkyl, aryl, or heteroaryl, wherein each alkyl, haloalkyl, cycloalkyl, heterocycloalkyl, aryl, or heteroaryl is optionally substituted with 1 to 8, or 1 to 5, or 1 to 3 substituents independently selected from alkyl, haloalkyl, cycloalkyl, heterocycloalkyl, aryl, heteroaryl, nitro, —OR$^u$, —C(O)OR$^u$, —C(O)NR$^u$R$^v$, —CHO, —COR$^u$, and cyano, and wherein each R$^u$ and R$^v$ is independently hydrogen, alkyl, or haloalkyl. In certain embodiments, R$^w$ is alkyl or haloalkyl. In another embodiment, R$^w$ is alkyl. In certain embodiments, R$^w$ is a C1-C10 alkyl, or a C1-C10 haloalkyl. In certain embodiments, R$^w$ is methyl, ethyl, propyl, CHF$_2$, CH$_2$F, or CF$_3$. In certain embodiments, the alkyl or haloalkyl may be further substituted with an ether moiety. For example, the alkyl or haloalkyl may be further substituted with —OR$^u$, where R$^u$ is alkyl or haloalkyl. In other embodiments, R$^w$ is alkyl, haloalkyl, or aryl optionally substituted with alkyl, haloalkyl, or nitro.

As used herein, "haloalkyl" refers to an unbranched or branched chain alkyl group, wherein one or more hydrogen atoms are replaced by a halogen. For example, where a residue is substituted with more than one halogen, it may be referred to by using a prefix corresponding to the number of halogen moieties attached. For example, dihaloalkyl or trihaloalkyl refers to alkyl substituted with two ("di") or three ("tri") halo groups, which may be, but are not necessarily, the same halogen; thus, for example, 2-chloro-2-fluorobutyl is within the scope of dihaloalkyl. An alkyl group in which each H is replaced with a halo group is referred to as a "perhaloalkyl". One example of a perhaloalkyl group is trifluoromethyl (—CF$_3$).

The sulfonic acids used in the methods described herein may include, for example, CF$_3$SO$_3$H (i.e., triflic acid), HCF$_2$CF$_2$SO$_3$H, C$_6$F$_5$SO$_3$H, 4-methylbenzenesulfonic acid (i.e., p-toluene-sulfonic acid), or 2,4-dinitrobenzenesulfonic acid. In one embodiment, the sulfonic acid is triflic acid. In yet another embodiment, the sulfonic acid is p-toluenesulfonic acid.

Salts of sulfonic acids used herein may have the structure of formula $Q^{r+}[R^uSO_3^-]_r$, wherein: Q is a cation; $R^u$ is as described above for sulfonic acids; and r is the charge of the cation. In some embodiments, $Q^{r+}$ is $Al^{3+}$, $Bi^{3+}$, $Cu^{2+}$, $Cu^+$, $Cr^{3+}$, $Fe^{3+}$, $Gd^{3+}$, $In^{3+}$, $Ni^{2+}$, $Nd^{3+}$, $Li^+$, $Na^+$, $K^+$, $Rb^+$, $Cs^+$, $Mg^{2+}$, $Ba^{2+}$, $Ca^{2+}$, $La^{3+}$, $Sc^{3+}$, $Ti^{4+}$, $V^{5+}$, $Y^{3+}$, $Zn^{2+}$, $Pt^{2+}$, $Pd^{2+}$, $Ag^+$, $Au^{3+}$, $Tl^{3+}$, $Tl^+$, $Re^{3+}$, $Hg_2^{2+}$, $Hg^{2+}$, $NH_4^+$, $Sn^{4+}$, $Sn^{3+}$, $Sn^{2+}$, $B^{3+}$, $Ga^{3+}$, $Pb^{4+}$, $Pb^{2+}$, $Co^{3+}$, $Co^{2+}$, $Ge^{4+}$, $Ge^{2+}$, $Ce^{4+}$, or $Ce^{3+}$.

The salts of the sulfonic acids used in the methods described herein may include, for example, is $Al(OTf)_3$, $Bi(OTf)_3$, $Cu(OTf)_2$, $Cu(OTf)$, $Cr(OTf)_3$, $Fe(OTf)_3$, $Gd(OTf)_3$, $In(OTf)_3$, $Ni(OTf)_2$, $Nd(OTf)_3$, $Rb(OTf)$, $Cs(OTf)$, $Mg(OTf)_2$, $La(OTf)_3$, $Sc(OTf)_3$, $Ti(OTf)_4$, $V(OTf)_5$, $Y(OTf)_3$, $Zn(OTf)_2$, $Pt(OTf)_2$, $Pd(OTf)_2$, $AgOTf$, $Au(OTf)_3$, $Tl(OTf)_3$, $Tl(OTf)$, $Re(OTf)_3$, $Hg_2(OTf)_2$, $Hg(OTf)_2$, $NH_4(OTf)$, $Sn(OTf)_4$, $Sn(OTf)_3$, $Sn(OTf)_2$, $B(OTf)_3$, $Ga(OTf)_3$, $Pb(OTf)_4$, $Pb(OTf)_2$, $Co(OTf)_3$, $Co(OTf)_2$, $Ge(OTf)_4$, $Ge(OTf)_3$, $Ge(OTf)_2$, $Ge(OTf)$, $Ce(OTf)_4$, $Ce(OTf)_3$, or any combinations thereof.

In certain embodiments, the sulfonic acid salt may be in the form of an ionic liquid. In yet other embodiments, the sulfonic acid may be a hydrate. In other embodiments, the sulfonic acid may be anhydrous. For example, the catalyst may be triflic anhydride. In other embodiments, the catalyst is a quaternary amine triflate.

In yet other embodiments, the sulfonic acid catalyst may be a sulfonic acid polymer, including for example, a sulfonic acid resin. In some embodiments, the sulfonic acid resin is a halosulfonic acid resin. In certain embodiments, the sulfonic acid resin is a fluorosulfonic acid resin. In one embodiment, the sulfonic acid resin is $R^{u1}CF_2SO_3H$, where $R^{u1}$ is alkyl or haloalkyl. For example, the sulfonic acid resin is a sulfonated tetrafluoroethylene polymer, such as Nafion.

The catalyst may, in some embodiments, be a sulfonate having the formula $R^uSO_3Si(R^{u1})_3$, wherein $R^u$ is as defined above for sulfonic acids; and $R^{u1}$ at each occurrence is independent alkyl or haloalkyl. For example, the salt of the sulfonic acid is trimethylsilyltrifluoromethanesulfonate.

In some embodiments, the catalyst is a sulfonamide, or a salt thereof. Sulfonamides used herein may have a structure of formula of $(R^{y1}SO_2)NH_2$ or $(R^{y1}SO_2)NH(R^z)$. In certain embodiments, $R^{y1}$ and $R^z$ are each independently alkyl, haloalkyl, cycloalkyl, heterocycloalkyl, aryl, or heteroaryl, wherein each alkyl, haloalkyl, cycloalkyl, heterocycloalkyl, aryl, or heteroaryl is optionally substituted with 1 to 8, or 1 to 5, or 1 to 3 substituents independently selected from alkyl, haloalkyl, cycloalkyl, heterocycloalkyl, aryl, heteroaryl, nitro, —$OR^u$, —$C(O)OR^u$, —$C(O)NR^uR^v$, —CHO, —$COR^u$, and cyano, and wherein each $R^u$ and $R^v$ is independently hydrogen, alkyl, or haloalkyl. In certain embodiments, $R^{y1}$ and $R^z$ are each independently alkyl or haloalkyl. In another embodiment, $R^{y1}$ and $R^z$ are each independently alkyl. In certain embodiments, $R^{y1}$ and $R^z$ are each independently a C1-C10 alkyl, or a C1-C10 haloalkyl. In certain embodiments, $R^{y1}$ and $R^z$ are each independently methyl, ethyl, propyl, $CHF_2$, $CH_2F$, or $CF_3$. In certain embodiments, the alkyl or haloalkyl may be further substituted with an ether moiety. For example, the alkyl or haloalkyl may be further substituted with —OR', where R' is alkyl or haloalkyl. In other embodiments, $R^{y1}$ and $R^z$ are each independently alkyl, haloalkyl, or aryl optionally substituted with alkyl, haloalkyl, or nitro.

Salts of the sulfonamides used herein may have the structure of formula $Q^{r+}[(R^{y1}SO_2)N(R^z)]_r$ or $Q^{r+}[(R^{y1}SO_2)NH]_r$, wherein: Q is a cation; $R^{y1}$ and $R^z$ (if present) is as described above for sulfonamides; and r is the charge of the cation. In some embodiments, $Q^{r+}$ is $Al^{3+}$, $Bi^{3+}$, $Cu^{2+}$, $Cu^+$, $Cr^{3+}$, $Fe^{3+}$, $Gd^{3+}$, $In^{3+}$, $Ni^{2+}$, $Nd^{3+}$, $Li^+$, $Na^+$, $K^+$, $Rb^+$, $Cs^+$, $Mg^{2+}$, $Ba^{2+}$, $Ca^{2+}$, $La^{3+}$, $Sc^{3+}$, $Ti^{4+}$, $V^{5+}$, $Y^{3+}$, $Zn^{2+}$, $Pt^{2+}$, $Pd^{2+}$, $Ag^+$, $Au^{3+}$, $Tl^{3+}$, $Tl^+$, $Re^{3+}$, $Hg_2^{2+}$, $Hg^{2+}$, $NH_4^+$, $Sn^{4+}$, $Sn^{3+}$, $Sn^{2+}$, $B^{3+}$, $Ga^{3+}$, $Pb^{4+}$, $Pb^{2+}$, $Co^{3+}$, $Co^{2+}$, $Ge^{4+}$, $Ge^{2+}$, $Ce^{4+}$, or $Ce^{3+}$.

In some embodiments, the catalyst is a sulfonimide, or a salt thereof. Sulfonimides used herein may have a structure of formula of $(R^{y1}SO_2)NH(SO_2R^{y2})$. In certain embodiments, $R^{y1}$ and $R^{y2}$ are each independently alkyl, haloalkyl, cycloalkyl, heterocycloalkyl, aryl, or heteroaryl, wherein each alkyl, haloalkyl, cycloalkyl, heterocycloalkyl, aryl, or heteroaryl is optionally substituted with 1 to 8, or 1 to 5, or 1 to 3 substituents independently selected from alkyl, haloalkyl, cycloalkyl, heterocycloalkyl, aryl, heteroaryl, nitro, —$OR^u$, —$C(O)OR^u$, —$C(O)NR^uR^v$, —CHO, —$COR^u$, and cyano, and wherein each $R^u$ and $R^v$ is independently hydrogen, alkyl, or haloalkyl. In certain embodiments, $R^{y1}$ and $R^{y2}$ are each independently alkyl or haloalkyl. In another embodiment, $R^{y1}$ and $R^{y2}$ are each independently alkyl. In certain embodiments, $R^{y1}$ and $R^{y2}$ are each independently a C1-C10 alkyl, or a C1-C10 haloalkyl. In certain embodiments, $R^{y1}$ and $R^{y2}$ are each independently methyl, ethyl, propyl, $CHF_2$, $CH_2F$, or $CF_3$. In certain embodiments, the alkyl or haloalkyl may be further substituted with an ether moiety. For example, the alkyl or haloalkyl may be further substituted with —$OR^u$, where $R^u$ is alkyl or haloalkyl. In other embodiments, $R^{y1}$ and $R^{y2}$ are each independently alkyl, haloalkyl, or aryl optionally substituted with alkyl, haloalkyl, or nitro.

The sulfonimides used in the methods described herein may include, for example, $NH(Tf)_2$ (i.e., triflimide). It should be understood that, as used herein, "-Tf" refers to triflyl.

Salts of sulfonimides used herein may have the structure of formula $Q^{r+}[(R^{y1}SO_2)N(R^{y2}SO_2)]_r$, wherein: Q is a cation; $R^{y1}$ and $R^{y2}$ are as described above for sulfonimides; and r is the charge of the cation. In some embodiments, $Q^{r+}$ is $Al^{3+}$, $Bi^{3+}$, $Cu^{2+}$, $Cu^+$, $Cr^{3+}$, $Fe^{3+}$, $Gd^{3+}$, $In^{3+}$, $Ni^{2+}$, $Nd^{3+}$, $Li^+$, $Na^+$, $K^+$, $Rb^+$, $Cs^+$, $Mg^{2+}$, $Ba^{2+}$, $Ca^{2+}$, $La^{3+}$, $Sc^{3+}$, $Ti^{4+}$, $V^{5+}$, $Y^{3+}$, $Zn^{2+}$, $Pt^{2+}$, $Pd^{2+}$, $Ag^+$, $Au^{3+}$, $Tl^{3+}$, $Tl^+$, $Re^{3+}$, $Hg_2^{2+}$, $Hg^{2+}$, $NH_4^+$, $Sn^{4+}$, $Sn^{3+}$, $Sn^{2+}$, $B^{3+}$, $Ga^{3+}$, $Pb^{4+}$, $Pb^{2+}$, $Co^{3+}$, $Co^{2+}$, $Ge^{4+}$, $Ge^{2+}$, $Ce^{4+}$, or $Ce^{3+}$.

The salts of sulfonimides used herein may include, for example, $Al[N(Tf)_2]_3$, $Bi[N(Tf)_2]_3$, $Cu[N(Tf)_2]_2$, $Cu[N(Tf)_2]$, $Cr[N(Tf)_2]_3$, $Fe[N(Tf)_2]_3$, $Gd[N(Tf)_2]_3$, $In[N(Tf)_2]_3$, $Ni[N(Tf)_2]_2$, $Nd[N(Tf)_2]_3$, $Li[N(Tf)_2]$, $Na[N(Tf)_2]$, $K[N(Tf)_2]$, $Rb[N(Tf)_2]$, $Cs[N(Tf)_2]$, $Mg[N(Tf)_2]_2$, $Ba[N(Tf)_2]_2$, $Ca[N(Tf)_2]_2$, $La[N(Tf)_2]_3$, $Sc[N(Tf)_2]_3$, $Ti[N(Tf)_2]_4$, $V[N(Tf)_2]_5$, $Y[N(Tf)_2]_3$, $Zn[N(Tf)_2]_2$, $Pt[N(Tf)_2]_2$, $Pd[N(Tf)_2]_2$, $Ag[N(Tf)_2]$, $Ag[N(Tf)_2]_2$, $Au[N(Tf)_2]_3$, $Tl[N(Tf)_2]_3$, $Tl[N(Tf)_2]$, $Re[N(Tf)_2]_3$, $Hg_2[N(Tf)_2]_2$, $Hg[N(Tf)_2]_2$, $NH_4[N(Tf)_2]$, $Sn[N(Tf)_2]_4$, $Sn[N(Tf)_2]_3$, $Sn[N(Tf)_2]_2$, $B[N(Tf)_2]_3$, $Ga[N(Tf)_2]_3$, $Pb[N(Tf)_2]_4$, $Pb[N(Tf)_2]_2$, $Co[N(Tf)_2]_3$, $Co[N(Tf)_2]_2$, $Ge[N(Tf)_2]_4$, $Ge[N(Tf)_2]_3$, $Ge[N(Tf)_2]_2$, $Ge[N(Tf)_2]$, $Ce[N(Tf)_2]_4$, $Ce[N(Tf)_2]_3$, or any combinations thereof. In other embodiments, the salt of the sulfonimide is ethyldimethylpropylammonium bis(trifluoromethylsulfonyl)imide, 1-butyl-1-methylpyrrolidinium bis (trifluoromethylsulfonyl)imide, 1-ethyl-3-methylimidazolium bis(trifluoromethylsulfonyl)imide, 1-butyl-3-methylimidazolium bis(trifluoromethylsulfonyl)imide, 1-allyl-3-methylimidazolium bis(trifluoromethylsulfonyl)

imide, triethylsulfonium bis(trifluoromethylsulfonyl)imide, trihexyltetradecylphosphonium bis(trifluoromethylsulfonyl) amide, 1,2-dimethyl-3-propylimidazolium bis(trifluoromethylsulfonyl)imide, $[(C_6H_{13})_3(C_{14}H_{29})P]^+[(CF_3SO_2)_2N]^-$, $[C_{11}H_{16}N]^+[N(SO_2CF_3)_2]^-$, $[C_8H_{15}N_2]^+[N(SO_2CF_3)_2]^-$, $[C_6H_{11}N_2]^+[N(SO_2CF_2CF_3)_2]^-$, $[C_6H_{11}N_2]^+[N(SO_2CF_3)_2]^-$, $[C_6H_{14}N]^+[N(SO_2CF_3)_2]^-$, 1-butyl-1-methylpyrrolidinium trifluoromethanesulfonate, 1-ethyl-3-methylimidazolium trifluoromethanesulfonate, 1-butyl-3-methylimidazolium trifluoromethanesulfonate, 1-butyl-3-methylimidazolium trifluoromethanesulfonate, or any combinations thereof. In one embodiment, the salt of the sulfonimide is bis(pentafluoroethylsulfonyl)imide salt.

In yet other embodiments, the salt of the sulfonic acid, sulfonamide, or sulfonimide has a cation, wherein the reduction of the cation to its elemental state (i.e., zero oxidation state) has a standard reduction potential greater than −0.2 eV relative to standard hydrogen potential. Any suitable methods or techniques known in the art may be used to measure standard reduction potential.

Other Acids

Other suitable acids may also be used as the catalyst in the methods described herein. In some embodiments, the acid has a pKa that is lower than the pKa of sulfuric acid. In other embodiments, the acid is $HClO_4$ or $H_2SO_4$.

Water-Tolerant Catalysts

In some embodiments, the catalysts may also be water-tolerant catalysts. As used herein, "a water-tolerant catalyst" refers to a catalyst that is not deactivated by the presence of water in a given reaction. One of skill in the art would recognize that a given catalyst may show water stability for the purposes of one reaction, but not toward another. Water-tolerant catalyst can improve recyclability of the catalyst used in the reaction on industrial scale, since water can often be produced as a by-product in the reaction. In some embodiments, the water-tolerant catalyst may have a $pK_h$ between 4.3 and 10.08. $K_h$ is the hydrolysis constant. $pK_h$ is defined as follows:

$$pK_h = -\log K_{xy}, \text{ where}$$

$$Kxy = \frac{[M_x(OH)_y^{(xz-y)+}][H^+]^y}{[M^{z+}]^x} * \frac{g_{xy}g_{H^+}^y}{g_{M^{z+}}^x a_{H_2O^y}},$$

based on the following reaction: $x\ M^{z+} + y\ H_2O \rightleftharpoons M_x(OH)_y^{(xz-y)} + y\ H^+$, where M is the metal cation. In other embodiments, the water-tolerant catalyst may have a water exchange rate constant of at least $3.2 \times 10^6\ M^{-1}s^{-1}$. See generally Kobayashi et al., *J. Am. Chem. Soc.* 1998, 120, 8287-8288.

Examples of water-tolerant catalysts may include those with a metal cation selected from Sc(III), Y(III), Ln(III), Fe(II), Cu(II), Zn(II), Cd(II), Pb(II), La(III), Ce(III), Pr(III), Nd(III), Sm(III), Eu(III), Gd(III), Tb(III), Dy(III), Ho(III), Er(III), Tm(III), Yb(III), and Lu(III). In certain embodiments, the catalyst may include Fe(II), Cu(II), Zn(II), Cd(II), Pb(II) Sc(III), Y(III), Ln(III), Mn(II), or Ag(I). Water-tolerant catalysts may include, for example, $ScCl_3$, $Sc(ClO_4)_3$, $Mn(ClO_4)_2$, $FeCl_2$, $Fe(ClO_4)_2$, $FeCl_3$, $Fe(ClO_4)_3$, $Co(ClO_4)_2$, $Ni(ClO_4)_2$, $CuCl_2$, $Cu(ClO_4)_2$, $ZnCl_2$, $Zn(ClO_4)_2$, $YCl_3$, $Y(ClO_4)_3$, $AgClO_4$, $CdCl_2$, $Cd(ClO_4)_2$, $InCl_3$, $In(ClO_4)_3$, $SnCl_2$, $La(OTf)_3$, $Ce(OTf)_3$, $Pr(OTf)_3$, $Nd(OTf)_3$, $Sm(OTf)_3$, $Eu(OTf)_3$, $Gd(OTf)_3$, $Tb(OTf)_3$, $Dy(OTf)_3$, $Ho(OTf)_3$, $Er(OTf)_3$, $Tm(OTf)_3$, $YbCl_3$, $Yb(ClO_4)_3$, $Yb(OTf)_3$, $Lu(OTf)_3$, $PbCl_2$, and $Pb(ClO_4)_2$.

Supported or Unsupported Catalysts

Any of the catalysts described above may be unsupported or supported. In one embodiment, the catalyst is unsupported. In another embodiment, the catalyst is supported by a solid support. Suitable supports may include, for example, carbon, alumina, silica, ceria, titania, zirconia, niobia, zeolite, magnesia, clays, iron oxide, silicon carbide, aluminosilicates, and any modifications, mixtures or combinations thereof. In certain embodiments, the support is silica, alumina, mordenite, carbon (including, for example, activated carbon), or zeolites (e.g., HY zeolite). Examples of supported catalyst may include copper on mordenite, alumina or zeolite. In one embodiment, the catalyst is copper (II) on mordenite, copper chloride on silica, copper chloride on alumina, or copper chloride on HY zeolite. In another embodiment, the support is activated carbon. The activated carbon may also be further treated, for example, acid treated (e.g., $H_3PO_4$ treated).

Solid supported catalysts can more easily be recovered, recycled, and used in a continuous process. When a catalyst support is used, the metals may be deposited using any procedures known in the art. See e.g., Schwarz et al., *Chem. Rev.* 95, 477-510, (1995).

Homogeneous or Heterogeneous Catalysts

In some embodiments, the catalyst is homogeneous in the reaction mixture. As used herein, a "homogeneous catalyst" refers to a catalyst that substantially dissolves in the reaction mixture under the reaction conditions. For example, acetic acid as the catalyst substantially dissolves in dioxane. In another example, copper triflate substantially dissolves in dodecane under the reaction conditions, but not at all conditions (e.g., at standard, temperature and pressure). A catalyst is "substantially dissolved" when the amount of dissolved catalyst exceeds the quantity of undissolved catalyst at the reaction conditions. In some embodiments, the catalyst is substantially dissolved when the ratio of amount of undissolved catalyst to the amount of dissolved catalyst is between 0:1 and 1:1 at the reaction conditions. In one embodiment, the ratio of amount of undissolved catalyst to the amount of dissolved catalyst is about 0 at the reaction conditions. Any suitable methods may be used to determine or quantify the solubility of catalyst.

In one embodiment, the homogeneous catalyst is a sulfonic acid, or a salt, ester, anhydride or resin thereof, a sulfonamide, or a salt thereof, or a sulfonimide, or a salt thereof.

In other embodiments, the catalyst is heterogeneous in the reaction. As used herein, a "heterogeneous catalyst" refers to any catalyst that is not a homogeneous catalyst as described above.

It should be understood that the homogeneity or heterogeneity of a catalyst may depend on the solvent or solvent mixtures used, as well as the reaction conditions.

Amount of Catalyst

The amount of catalyst used may vary depending on the catalyst, starting materials, solvent, and reaction conditions. As used herein, "catalyst loading" refers to the amount of catalyst used in relation to the amount of the furan of formula (B-I), (B-IIa), or (N-I) used, expressed as a weight ratio of the furan of formula (B-I), (B-IIa), or (N-I) (as the starting material) to the catalyst used. For example, in some embodiments, the catalyst loading is between 10 to 500, or between 10 to 300, or between 50 to 500, or between 100 to 500, or between 100 to 300, or between 200 to 500.

Further, it should be understood that in certain embodiments, one or more of the catalysts described herein may be used.

c) Solvents

A solvent, or a combination or mixture of solvents, may also be optionally added to the reaction mixture. The solvent(s) used in the methods described herein dissolve(s) at least a portion of ethylene, and/or the furan of formula (B-I), (B-IIa), or (N-I) as the case may be. The solvent(s) used in the methods described herein may be obtained from any source, including any commercially available sources. In some embodiments, the methods described herein use certain solvents to convert the furan of formula (B-I), (B-IIa), or (N-I) to a compound of formula (C), (C-I), or (P) respectively, with yields of at least 50%, at least 75%, at least 80%, at least 85%, at least 90%, at least 95%, or at least 99% on a molar basis.

The particular solvents used in the methods described herein typically can solubilize, or at least partially solubilize, the starting materials and/or catalysts, which can help to enhance the solvation effect and improve the reaction rate. For example, in some embodiments, the solvent has an ethylene solubility between about 0 mol/L and about 0.82 mol/L, between about 0.82 mol/L and about 1.2 mol/L, or between about 1.2 mol/L and about 4.0 mol/L, when ethylene solubility is measured a temperature of about 23° C.

The solvents used may also be selected based on their boiling points. The solvents may be selected based on their boiling points at standard pressure or operating pressure. In some embodiments, the solvent may have a boiling point of between 80° C. and 400° C., or between 150° C. and 350° C., or between 350° C. and 450° C. Further, the solvent, or the combination or mixture of solvents, selected may have a boiling point higher than the compound of formula (C), (C-I), or (P). This would allow the compound of formula (C), (C-I), or (P)) to be distilled from the reaction mixture, leaving the catalyst and solvent behind to be recycled and/or recovered.

Additionally, the solvents are typically stable to the process conditions, and preferably can be recycled for use again in the reaction. The recyclability of the solvent is particularly useful for performing the methods described herein on a commercial scale.

The solvents used herein may be aliphatic or aromatic. The solvents may also have one or more functional groups such as halo, ester, ether, and alcohol, or any combinations or mixtures thereof. The solvent may also be non-cyclic (including linear or branched) or cyclic. While the different classes of solvents are described below (e.g., aprotic solvents, aliphatic solvents, aromatic solvents, alkyl phenyl solvents, ether solvents, alcohol solvents, halogenated solvents, or ionic liquids), it should be understood that the solvent may fall within one or more classes described. For example, dioxane is an ether that is aprotic. In another example, Wibaryl® A is an aromatic solvent that can more specifically be classified as an alkyl phenyl solvent.

For example, in one embodiment, the solvent includes dimethylacetamide (e.g., N,N-dimethylacetamide), dimethylformamide (e.g., N,N-dimethylformamide), acetonitrile, sulfolane, dioxane, dioxane, dimethyl ether, diethyl ether, glycol dimethyl ether (monoglyme), ethylene glycol diethyl ether (ethyl glyme), diethylene glycol dimethyl ether (diglyme), diethylene glycol diethyl ether (ethyl digylme), triethylene glycol dimethyl ether (triglyme), diethylene glycol dibutyl ether (butyl diglyme), tetraethylene glycol dimethyl ether (tetraglyme), polygyme, proglyme, higlyme, tetrahydrofuran, ethylene glycol, diethylene glycol, triethylene glycol, polyethylene glycol, cyclobutanone, cyclopentanone, cyclohexanone, cycloheptanone, cyclooctanone, methyl acetate, ethyl acetate, propyl acetate, butyl acetate, methyl lactate, ethyl lactate, propyl lactate, butyl lactate, triacetin, dibutylphthalate, butane, pentane, cyclopentane, hexane, cyclohexane, heptane, cycloheptane, octane, cyclooctane, nonane, decane, undecane, dodecane, hexadecane, tetrachloride, chloroform, dichloromethane, nitromethane, toluene, anisole, nitrobenzene, bromobenzene, methylpyrrole (e.g., N-methylpyrrole), methylpyrrolidinone (e.g., N-methylpyrrolidinone), dimethylfuran (e.g., 2,5-dimethylfuran), dichlorobenzene (e.g., o-dichlorobenzene), or water.

Aprotic Solvents

In some embodiments, the solvent includes an aprotic solvent. For example, the aprotic solvent may have a dipole moment above 0.1. One of skill in the art would understand that the dipole moment is a measure of polarity of a solvent. The dipole moment of a liquid can be measured with a dipole meter. Suitable aprotic solvents may include, for example, dimethylacetamide, dimethylformamide (including, for example, N,N-dimethylformamide), methylpyrrolidinone (e.g., N-methylpyrrolidinone), dioxane, polyethers (including, for example, glyme, diglyme, triglyme, tetraglyme), acetonitrile, sulfolane, ethers (including, for example, tetrahydrofuran, dialkylether (e.g., dimethylether, diethylether), nitromethane, anisole, nitrobenzene, bromobenzene, chlorobenzene, or any combinations or mixtures thereof.

Aliphatic Solvents

In one embodiment, the solvent includes an aliphatic solvent. The aliphatic solvent may be linear, branched, or cyclic. The aliphatic solvent may also be saturated (e.g., alkane) or unsaturated (e.g., alkene or alkyne). In some embodiments, the solvent includes a C1-C20 aliphatic solvent, a C1-C10, aliphatic solvent, or a C1-C6 aliphatic solvent. In certain embodiments, the solvent includes a C4-C30 aliphatic solvent, a C6-C30 aliphatic solvent, a C6-C24 aliphatic solvent, or a C6-C20 aliphatic solvent. In certain embodiments, the solvent includes C8+ alkyl solvent, or a C8-C50 alkyl solvent, a C8-C40 alkyl solvent, a C8-C30 alkyl solvent, a C8-C20 alkyl solvent, or a C8-C16 alkyl solvent. Suitable aliphatic solvents may include, for example, butane, pentane, cyclopentane, hexane, cyclohexane, heptane, cycloheptane, octane, cyclooctane, nonane, decane, undecane, dodecane, hexadecane, or any combinations or mixtures thereof. In certain embodiments, the aliphatic solvent is linear.

The aliphatic solvent may be obtained from petroleum refining aliphatic fractions, including any isomers of the aliphatic solvents, and any mixtures thereof. For example, alkane solvents may be obtained from petroleum refining alkane fractions, including any isomers of the alkane solvents, and any mixtures thereof. In certain embodiments, the solvent includes petroleum refining alkane fractions.

Aromatic Solvents

In another embodiment, the solvent includes an aromatic solvent. In some embodiments, the solvent includes a C6-C20 aromatic solvent, a C6-C12 aromatic solvent, or a C13-C20 aromatic solvent. The aromatic solvent may be optionally substituted. Suitable aromatic solvents may include, for example, toluene, anisole, nitrobenzene, bromobenzene, chlorobenzene (including, for example, dichlorobenzene), dimethylfuran (including, for example, 2,5-dimethylfuran), and methylpyrrole (including, for example, N-methylpyrrole).

In some variations, the aromatic solvent may include at least one alkyl chain substituent, and such aromatic solvents may include monocyclic aromatic ring system or bicyclic or polyciclic aromatic systems (including fused ring systems).

Examples of such aromatic solvents include, for example, naphthalene, anthracene, Dowtherm® (mixture of biphenyl and diphenyl oxide), Dowtherm® G (di- and tri-aryl ethers), Dowtherm® Q (a mixture of diphenylethane and alkylated aromatics), and Dowtherm® MX (a mixture of alkylated aromatics). As discussed above, any combinations or mixtures of such solvents may also be used.

Alkyl Phenyl Solvents

As used herein, "an alkyl phenyl solvent" refers to a class of solvents that may have one or more alkyl chains and one or more phenyl or phenyl-containing ring systems. The alkyl phenyl solvent may be referred to as an alkylbenzene or a phenylalkane. One skilled in the art would recognize that certain phenylalkanes may also be interchangeably referred to as an alkylbenzene. For example, (1-phenyl)pentane and pentylbenzene refer to the same solvent.

In some embodiments, the solvent includes an alkylbenzene. Examples may include (monoalkyl)benzenes, (dialkyl)benzenes, and (polyalkyl)benzenes. In certain embodiments, the alkylbenzene has one alkyl chain attached to one benzene ring. The alkyl chain may have one or two points of attachment to the benzene ring. Examples of alkylbenzenes with one alkyl chain having one point of attachment to the benzene ring include pentylbenzene, hexylbenzene and dodecylbenzene. In embodiments where the alkyl chain has two points of attachment to the benzene ring, the alkyl chain may form a fused cycloalkyl ring to the benzene. Examples of alkylbenzenes with one alkyl having two points of attachment to the benzene ring include tetralin. It should be understood that the fused cycloalkyl ring may be further substituted with one or more alkyl rings.

In certain variations, the solvent includes para-xylene, mesitylene, dodecylbenzene, pentylbenzene, or hexylbenzene.

In other embodiments, the alkylbenzene has two or more alkyl chains (e.g., 2, 3, 4, 5, or 6 alkyl chains) attached to one benzene ring.

In yet other embodiments, the alkylbenzene is an alkyl-substituted fused benzene ring system. The fused benzene ring system may include benzene fused with one or more heterocyclic rings. In one embodiment, the fused benzene ring system may be two or more fused benzene rings, such as naphthalene. The fused benzene ring system may be optionally substituted by one or more alkyl chains.

In some embodiments, the solvent includes phenylalkane. Examples may include (monophenyl)alkanes, (diphenyl)alkanes, and (polyphenyl)alkanes. In certain embodiments, the phenylalkane has one phenyl ring attached to one alkyl chain. The phenyl ring may be attached to any carbon along the alkyl chain. For example, the phenyl alkyl having one alkyl chain may be (1-phenyl)pentane, (2-phenyl)pentane, (1-phenyl)hexane, (2-phenyl)hexane, (3-phenyl)hexane, (1-phenyl)dodecane, and (2-phenyl)dodecane.

In other embodiments, the phenylalkane has two or more phenyl rings attached to one alkyl chain.

In one variation, the solvent includes Wibaryl® (e.g., benzene substituted with $C_{10-13}$ alkyl chain), Wibaryl® F (heavy alkylate), Wibaryl® A (diphenylalkanes, wherein the alkyl chains are $C_{10-13}$ alkyl chains), Wibaryl® B (dialkylbenzenes, wherein the alkyl chains are $C_{10-13}$ alkyl chains), Wibaryl® AB (a mixture of diphenylalkanes and dialkylbenzenes), Wibaryl® R (oligo- and polyalkylbenzenes), Cepsa Petrelab® 500-Q (linear alkylbenzene containing side alkyl chains of 10-13 carbon atoms), Cepsa Petrelab® 550-Q (linear alkylbenzene containing side alkyl chains of 10-13 carbon atoms), Cepsa Petrene® 900-Q (heavy alkylbenzene containing primarily dialkylbenzenes), Synnaph® AB 3 (heavy alkyl benzene), Synnaph® DAB4 (dialkylbenzene), or Therminol® 55 (benzene substituted with $C_{13-30}$ alkyl chains).

In certain embodiments, the alkyl chain of a solvent may be 1 to 20 carbon atoms (e.g., $C_{1-20}$ alkyl). In one embodiment, the alkyl chain may be 4 to 15 carbons (e.g., $C_{4-15}$ alkyl), or 10 to 13 carbons (e.g., $C_{10-13}$ alkyl). The alkyl chain may be linear or branched. Linear alkyl chains may include, for example, n-propyl, n-butyl, n-hexyl, n-heptyl, n-octyl, n-nonanyl, n-decyl, n-undecyl, and n-dodecyl. Branched alkyl chains may include, for example, isopropyl, sec-butyl, isobutyl, tert-butyl, and neopentyl. In some embodiments where the solvent includes two or more alkyl chains, certain alkyl chains may be linear, whereas other alkyl chains may be branched. In other embodiments where the solvent includes two or more alkyl chains, all the alkyl chains may be linear or all the alkyl chains may be branched.

For example, the solvent includes a linear alkylbenzene ("LAB"). Linear alkylbenzenes are a class of solvents having the formula $C_6H_5C_nH_{2n+1}$. For example, in one embodiment, the linear alkylbenzene is dodecylbenzene. Dodecylbenzene is commercially available, and may be "hard type" or "soft type". Hard type dodecylbenzene is a mixture of branched chain isomers. Soft type dodecylbenzene is a mixture of linear chain isomers. In one embodiment, the solvent includes a hard type dodecylbenzene.

In some embodiments, the solvent includes any of the alkyl phenyl solvents described above, in which the phenyl ring is substituted with one or more halogen atoms. In certain embodiments, the solvent includes an alkyl(halobenzene). For example, the alkyl(halobenzene) may include alkyl(chlorobenzene). In one embodiment, the halo substituent for the phenyl ring may be, for example, chloro, bromo, or any combination thereof.

In other embodiments, the solvent includes naphthalene, naphthenic oil, alkylated naphthalene, diphenyl, polychlorinated biphenyls, polycyclic aromatic hydrocarbons, or halogenated hydrocarbons.

Ether Solvents

In other embodiments, the solvent includes an ether solvent, which refers to a solvent having at least one ether group. For example, the solvent includes a C2-C20 ether, or a C2-C10 ether. The ether solvent can be non-cyclic or cyclic. For example, the ether solvent may be alkyl ether (e.g., diethyl ether, glycol dimethyl ether (glyme), diethylene glycol dimethyl ether (diglyme), or triethylene glycol dimethyl ether (triglyme)). In another example, the ether solvent may be cyclic, such as dioxane (e.g., 1,4-dioxane), dioxin, tetrahydrofuran, or a cycloalkyl alkyl ether (e.g., cyclopentyl methyl ether).

The solvent may include an acetal such as dioxolane (e.g., 1,3-dioxolane).

The solvent may also include a polyether with two or more oxygen atoms. In some embodiments, the ether solvent has a formula as follows:

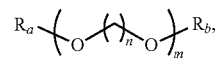

where each $R_a$ and $R_b$ are independently aliphatic moieties, and n and m are integers equal to or greater than 1. In some embodiments, each $R_a$ and $R_b$ are independently alkyl. In certain embodiments, each $R_a$ and $R_b$ are independently C1-C10 alkyl, or C1-C6 alkyl. $R_a$ and $R_b$ may be the same or different. In other embodiments, each n and m are independently 1 to 10, or 1 to 6, where n and m may be the same or different.

The formula above includes proglymes (such as dipropylene glycol dimethylether), or glymes (such as glycol diethers based on ethylene oxide). In one embodiment, the solvent includes glyme, diglyme, triglyme, or tetraglyme.

It should also be understood that a solvent having an ether group may also have one or more other functional groups. It should be understood, however, that the solvent may have an ether functional group in combination with one or more additional functional groups, such as alcohols. For example, the solvent includes alkylene glycols (e.g., ethylene glycol, diethylene glycol, triethylene glycol, polyethylene glycol), phenyl ethers (e.g., diphenyl ether, polyphenyl ethers), or alkylphenylethers (e.g., alkyldiphenyl ether).

Phenyl Ether Solvents

In other embodiments, the solvent includes phenyl ethers. In certain variations, the solvent includes monophenyl ethers, diphenyl ethers, or polyphenyl ethers. In some variations, the solvent includes diphenyl ether, methyldiphenyl ether, or ethyldiphenyl ether, or any combinations or mixtures thereof.

In certain embodiments, the solvent includes a polyphenyl ether that includes at least one phenoxy or at least one thiophenoxy moiety as the repeating group in ether linkages.

In one variation, the solvent includes Santovac® 5 or Santovac® 7.

Ester Solvents

In yet other embodiments, the solvent includes an ester solvent, which refers to a solvent having at least one ester group. For example, the solvent includes a C2-C20 ester, or a C2-C10 ester. The ester solvent can be non-cyclic (linear or branched) or cyclic. For example, non-cyclic ester solvents may include alkyl acetate (e.g., methyl acetate, ethyl acetate, propyl acetate, butyl acetate), triacetin, and dibutylphthalate. An example of cyclic ester is, for example, propylene carbonate. It should be understood, however, that a solvent having an ester group may also have one or more other functional groups. The ester solvent may also include alkyl lactate (e.g., methyl lactate, ethyl lactate, propyl lactate, butyl lactate), which has both an ester group as well as a hydroxyl group.

Alcohol Solvents

In yet other embodiments, the solvent includes an alcohol, which refers to a solvent having at least hydroxyl group. For example, the solvent can be a C1-C20 alcohol, a C1-C10 alcohol, or a C1-C6 alcohol. Alcohol solvents may include, for example, methanol, ethanol and propanol. The solvent may also be an alkanediol, such as 1,3-propanediol or propylene glycol.

Halogenated Solvents

In yet other embodiments, the solvent includes halogenated solvents. For example, the solvent can be a chlorinated solvent. Suitable chlorinated solvents may include, for example, carbon tetrachloride, chloroform, methylene chloride, bromobenzene and dichlorobenzene.

Ionic Liquids

The solvent may also be an ionic liquid. Suitable ionic liquids may include, for example, 1-allyl-3-methylimidazolium bromide and 1-benzyl-3-methylimidazolium tetrafluoroborate.

Solvent Combinations or Mixtures

A combination or mixture of solvents may also be used in the methods described herein. In some embodiments, an ether solvent may be combined with one or more other types of solvents listed above, including for example an aliphatic solvent. In one embodiment, the solvent combination or mixture is dioxane and an aliphatic solvent.

When a combination or mixture of solvents is used, the two or more solvents may be used in any suitable combination. For example, when two solvents are used, the two solvents may be present in a weight ratio of about 1 to about 1, or about 1 to about 2, or about 1 to about 3, or about 1 to about 4, or about 1 to about 5.

Amount of Solvent

The amount of solvent used may vary depending on the starting materials, catalyst used, and reaction conditions. For example, in some embodiments, the concentration of the furan of formula (B-I), (B-IIa), or (N-I) in the reaction mixture is from about 1 to about 75% by weight in the solvent, or from about 3 to about 50% by weight in the solvent. It should also be understood that the amount of solvent used may vary depending on whether the reaction is as a batch or a continuous system.

d) Reaction Conditions

The operating temperature refers to the average temperature of the reaction mixture in the vessel. In some embodiments, the operating temperature may be at least 150° C., or at least 200° C. In other embodiments, the operating temperature may be between 100° C. and 300° C., between 150° C. and 400° C., between 150° C. and 300° C., between 125° C. and 175° C., between 200° C. to 350° C., between 200° C. to 250° C., between 200° C. and 400° C., between 270° C. to 400° C., between 220° C. to 230° C., between 250° C. to 300° C., or between 150° C. and 220° C. In one embodiment, the operating temperature is between room temperature (e.g., 18° C.-22° C.) and 300° C. Higher operating temperatures can be used provided that the solvent selected is stable.

The operating pressure refers to the average absolute internal pressure of the vessel. In some embodiments, the reaction may proceed at an operating pressure between 1 bar and 1000 bar, between 10 bar to 1000 bar, between 20 bar to 1000 bar, between 50 bar to 1000 bar, between 100 bar to 1000 bar, between 150 bar to 500 bar, between 35 and 38 bar, between 1 bar and 50 bar, between 1 bar and 40 bar, between 1 bar and 30 bar, between 1 bar and 20 bar, between 1 bar and 10 bar, between 1 bar and 5 bar, between 5 bar and 30 bar, between 5 bar and 20 bar, or between 5 bar and 10 bar. At such operating pressures, the concentration of the ethylene reactant is sufficient high for optimal reaction rates.

In other embodiments, the operating pressure is between 50 psi and 1,000 psi, or between 50 psi and 800 psi, between 50 psi and 700 psi, between 50 psi and 600 psi, or between 600 psi and 1000 psi.

It should be understood that higher operating pressures can be used depending on the equipment available. In other embodiments, the ethylene is near critical where the temperature is between about 270K and about 290K, and the partial operating pressure of ethylene is between about 45 bar and about 65 bar. In other embodiments, the ethylene is supercritical, where the temperature is greater than or equal to about 282K, and the partial operating pressure of ethylene is greater than about 734 psi. In yet other embodiments, the ethylene is supercritical, wherein the temperature is greater than or equal to about 282K and the partial operating pressure of ethylene is greater than or equal to about 734 psi.

It should be understood and clearly conveyed herein that the operating temperature and operating pressure may be the same as if each and every combination were individually listed. For example, in one variation, the method is carried out at an operating temperature of about 225° C. and an operating pressure of about 34 bar (equivalent to about 500 psi).

The methods described herein may also be carried out under supercritical conditions (e.g., supercritical pressures and/or supercritical temperatures). For example, in one embodiment, supercritical conditions may be used if a solvent is not used in the reaction. In one embodiment, the method is carried out at or above 50 bar and/or at or above 9° C. (i.e., 282 K).

It should be understood that temperature may be expressed as degrees Celsius (° C.) or Kelvin (K). One of ordinary skill in the art would be able to convert the temperature described herein from one unit to another. Pressure may also be expressed as gauge pressure (barg), which refers to the pressure in bars above ambient or atmospheric pressure. Pressure may also be expressed as bar, atmosphere (atm), pascal (Pa) or pound-force per square inch (psi). One of ordinary skill in the art would be able to convert the pressure described herein from one unit to another.

The method may be performed with or without stirring. In certain preferred embodiments, the method is performed with stirring to increase conversion and/or selectivity.

Additionally, the method may be carried out batch-wise or continuously. The reaction time (in a batch-wise process) or residence time (in a continuous process) will also vary with the reaction conditions and desired yield, but is generally about 1 to 72 hours. In some of the foregoing embodiments, the reaction time or residence time is determined by the rate of conversion of the starting material. In some of the foregoing embodiments, the reaction mixture is reacted for 1 to 24 hours. In some of the foregoing embodiments, the reaction mixture is reacted for 1 to 10 hours. In some of the foregoing embodiments, the reaction mixture is reacted for 1 to 5 hours. In some of the foregoing embodiments, the reaction mixture is reacted for 1 to 3 hours. In some of the foregoing embodiments, the reaction mixture is reacted for less than 2 hours.

III. Nitro-Aldol Reactions

With reference again to FIG. 1, a (haloalkyl)furan, such as a furan of formula (A), can undergo a nitro-aldol reaction to produce a furan of formula (B). With reference again to FIG. 2, a furan of formula (M) can undergo a nitro-aldol reaction to produce a furan of formula (N). As described herein, in certain embodiments a furan of formula (M) an undergo a nitroaldol reaction to produce a furan of formula (MN). With reference again to FIG. 4, a (haloalkyl)furan, such as a furan of formula (A), can undergo a nitro-aldol reaction to produce a furan of formula (Q). As described herein, in some variations a (haloalkyl)furan, such as the furan of formula (A) can undergo a nitro-aldol reaction to produce a furan of formula (AB), a furan of formula (B), a furan of formula (Q), or a furan of formula (R), or any combinations thereof. In some variations, the furan of formula (A) may be combined with a nitroalkane of formula (I) in the presence of a base and optionally solvent to produce the furan of formula (AB), (B), (Q) or (R), or any combinations thereof. In other variations, a furan of formula (M) may be combined with a nitroalkane of formula (I) in the presence of a base and optionally solvent to produce the furan of formula (N) or the furan of formula (MN), or a combination thereof.

In certain variations, a furan of formula (A) is combined with a nitroalkane of formula (I) in the presence of a base and optionally solvent to produce a reaction mixture, and an acid is added to the reaction mixture to produce the furan of formula (B). Any suitable base and acid may be used. In some variations, the acid is a mineral acid (such as phosphoric acid or HCl) or a carboxylic acid. For example, in one embodiment, a furan of formula (A) is combined with a nitroalkane of formula (I) in the presence of n-butyllithium and optionally solvent to form a reaction mixture, then HCl is added to the reaction mixture to produce the furan of formula (B). In some embodiments, the solvent is hexane. In certain embodiments, 12 M HCl is added to the reaction mixture.

In certain variations, a furan of formula (A) is combined with a nitroalkane of formula (I) in the presence of a base and optionally solvent to produce a reaction mixture, and an acid is added to the reaction mixture to produce the furan of formula (R). Any suitable base and acid may be used. In some variations, the acid is a mineral acid (such as phosphoric acid or HCl) or a carboxylic acid. For example, in one embodiment, a furan of formula (A) is combined with a nitroalkane of formula (I) in the presence of n-butyllithium and optionally solvent to form a reaction mixture, then HCl is added to the reaction mixture to produce the furan of formula (R). In some embodiments, the solvent is hexane. In certain embodiments, 12 M HCl is added to the reaction mixture.

In certain variations, a furan of formula (M) is combined with a nitroalkane of formula (I) in the presence of a base and optionally solvent to produce a reaction mixture, and an acid is added to the reaction mixture to produce the furan of formula (N). Any suitable base and acid may be used. In some variations, the acid is a mineral acid (such as phosphoric acid or HCl) or a carboxylic acid. For example, in one embodiment, a furan of formula (M) is combined with a nitroalkane of formula (I) in the presence of n-butyllithium and optionally solvent to form a reaction mixture, then HCl is added to the reaction mixture to produce the furan of formula (N). In some embodiments, the solvent is hexane. In certain embodiments, 12 M HCl is added to the reaction mixture.

In some variations, the nitro-aldol reactions described herein are performed at a temperature between −100° C. and 200° C., between −100° C. and 100° C., between −100° C. and 0°, or at −78° C.

a) Nitroalkane

In some variations, the nitroalkane of formula (I) is:

wherein $R^x$ is H or alkyl. In one variation, $R^x$ is H. Thus, in one variation, the nitroalkane of formula (I) is $CH_3NO_2$. In other variations, $R^x$ is alkyl. In one variation, $R^x$ is methyl. It should be understood that when the nitroalkane of formula (I) is used to produce the furans of formulae (AB), (B), (Q), (MN), or (N), $R^x$ in formulae (I), (AB), (B), (Q), (MN), and (N) are the same.

b) Base

In some variations, the base is a non-nucleophilic base. In certain variations, the base is a non-nucleophilic base that forms a weak acid upon protonation. In certain variations, the base is cesium carbonate ($CsCO_3$) or an amine, such as triethylamine or pyridine. In other variations, the base is ammonium acetate or alumina.

In certain variations, the base is an organolithium compound. For example, in certain embodiments, the base is n-butyllithium, methyllithium, sec-butyllithium, isopropyllithium, or tert-butyllithium. In one embodiment, the base is n-butyllithium.

The base may be homogenous with the reaction mixture or heterogenous with the reaction mixture. For example, in some embodiments, the base is supported on a resin. In some embodiments, the base is a resin. In certain embodiments, the base is an ion-exchange resin. In some embodiments, the base is an amine ion-exchange resin including, for example, poly(4-vinylpyridine). In one embodiment, the base is Reillex® 425. A combination of any of the bases described herein may also be used.

c) Solvent

In some variations, the solvent includes an aromatic solvent or an alkyl acetate solvent. In one variation, the solvent is toluene, methyl acetate, ethyl acetate, tetrahydrofuran, or propyl acetate. In some variations, the solvent is polar, or aprotic, or polar and aprotic. A combination of any of the solvents described herein may also be used.

Production of Furans of Formula (AB)

As described herein, the furan of formula (AB) may be produced from haloalkylfurfurals. Haloalkylfurfurals, such as 5-(chloromethyl)furfural, may be obtained from biomass, a renewable source. Thus, the furans of formula (AB) may be obtained from renewable sources.

In certain aspects, the furan of formula (AB) may be produced by:
combining a furan of formula (A) with a nitroalkane of formula (I) to produce the furan of formula (AB).

In some variations, the furan of formula (A) is:

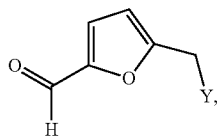

(A)

wherein Y is halo.

In one variation, Y is chloro. Thus, in one variation, the furan of formula (A) is:

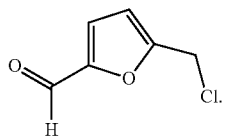

In another variation, Y is bromo. In yet another variation Y is fluoro. In yet another variation Y is iodo.

In some variations, the nitroalkane of formula (I) is:

$(R^xCH_2)NO_2$ (I), wherein $R^x$ is H or alkyl.

It should be understood that when the compound of formula (I) is used to produce the furan of formula (AB), IV in formulae (I) and (AB) are the same.

In other variations of the compounds of formulae (I) and (AB), $R^x$ is alkyl. In certain variations of the compounds of formulae (I) and (AB), $R^x$ is $C_{1-20}$ alkyl, or $C_{1-10}$ alkyl, or $C_{1-5}$ alkyl. In certain variations, $R^x$ is methyl, ethyl, propyl or butyl.

Production of Furans of Formula (B)

With reference again to FIG. 1, the furan of formula (B) may be produced from haloalkylfurfurals. Haloalkylfurfurals, such as 5-(chloromethyl)furfural, may be obtained from biomass, a renewable source. Thus, the furans of formula (B) may be obtained from renewable sources.

In certain aspects, the furan of formula (B) may be produced by:
combining a furan of formula (A) with a nitroalkane of formula (I) to produce the furan of formula (B).

In some variations, the furan of formula (A) is:

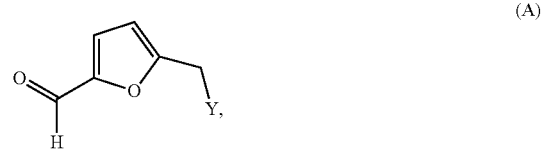

(A)

wherein Y is halo.

In one variation, Y is chloro. Thus, in one variation, the furan of formula (A) is:

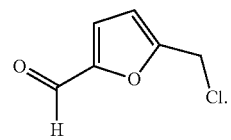

In another variation, Y is bromo. In yet another variation Y is fluoro. In yet another variation Y is iodo.

In some variations, the nitroalkane of formula (I) is:

$(R^xCH_2)NO_2$ (I), wherein $R^x$ is H or alkyl.

It should be understood that when the compound of formula (I) is used to produce the furan of formula (B), IV in formulae (I) and (B) are the same.

In some variations of the compounds of formulae (I) and (B), $R^x$ is H. Thus, in some variations:
the furan of formula (B) is:

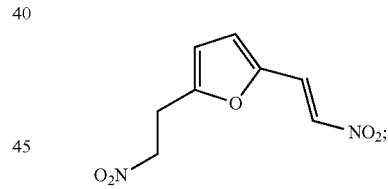

and
the nitroalkane of formula (I) is:

$CH_3NO_2$.

In other variations of the compounds of formulae (I) and (B), $R^x$ is alkyl. In certain variations of the compounds of formulae (I) and (B), $R^x$ is $C_{1-20}$ alkyl, or $C_{1-10}$ alkyl, or $C_{1-5}$ alkyl. In certain variations, $R^x$ is methyl, ethyl, propyl or butyl.

Production of Furans of Formula (Q)

With reference again to FIG. 4, the furan of formula (Q) may be produced from haloalkylfurfurals. Haloalkylfurfurals, such as 5-(chloromethyl)furfural, may be obtained from biomass, a renewable source. Thus, the furans of formula (Q) may be obtained from renewable sources.

In certain aspects, the furan of formula (Q) may be produced by:
combining a furan of formula (A) with a nitroalkane of formula (I) to produce the furan of formula (Q).

In some variations, R¹ and R² are H. Thus, in some variations, the furan of formula (A) is:

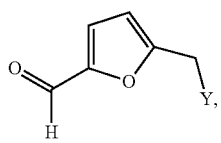

wherein Y is halo.

In one variation, Y is chloro. Thus, in one variation, the furan of formula (A) is:

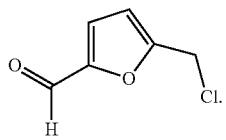

In another variation, Y is bromo. In yet another variation Y is fluoro. In yet another variation Y is iodo.

In some variations, the nitroalkane of formula (I) is:

$$(R^xCH_2)NO_2 \qquad (I),$$

wherein $R^x$ is H or alkyl.

It should be understood that when the compound of formula (I) is used to produce the furan of formula (Q), IV in formulae (I) and (Q) are the same.

In some variations of the compounds of formulae (I) and (Q), R¹, R², and $R^x$ are H. Thus, in some variations: the furan of formula (Q) is:

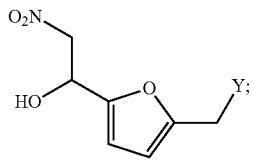

and
the nitroalkane of formula (I) is:

In other variations of the compounds of formulae (I) and (Q), $R^x$ is alkyl. In certain variations of the compounds of formulae (I) and (Q), $R^x$ is $C_{1-20}$ alkyl, or $C_{1-10}$ alkyl, or $C_{1-5}$ alkyl. In certain variations, $R^x$ is methyl, ethyl, propyl or butyl.

Production of Furans of Formula (R)

As described herein, the furan of formula (R) may be produced from haloalkylfurfurals. Haloalkylfurfurals, such as 5-(chloromethyl)furfural, may be obtained from biomass, a renewable source. Thus, the furans of formula (R) may be obtained from renewable sources.

In certain aspects, the furan of formula (R) may be produced by:
combining a furan of formula (A) with a nitroalkane of formula (I) to produce the furan of formula (R).

In some variations, R¹ and R² are H. Thus, in some variations, the furan of formula (A) is:

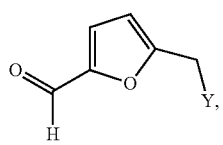

wherein Y is halo.

In one variation, Y is chloro. Thus, in one variation, the furan of formula (A) is:

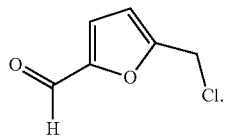

In another variation, Y is bromo. In yet another variation Y is fluoro. In yet another variation Y is iodo.

In some variations, the nitroalkane of formula (I) is:

$$(R^xCH_2)NO_2 \qquad (I),$$

wherein $R^x$ is H or alkyl.

It should be understood that when the compound of formula (I) is used to produce the furan of formula (R), IV in formulae (I) and (R) are the same.

In some variations of the compounds of formulae (I) and (R), R¹, R², and $R^x$ are H. Thus, in some variations: the furan of formula (Q) is:

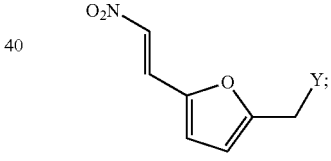

and
the nitroalkane of formula (I) is:

In other variations of the compounds of formulae (I) and (R), $R^x$ is alkyl. In certain variations of the compounds of formulae (I) and (R), $R^x$ is $C_{1-20}$ alkyl, or $C_{1-10}$ alkyl, or $C_{1-5}$ alkyl. In certain variations, $R^x$ is methyl, ethyl, propyl or butyl.

Production of Furans of Formula (M)

With reference again to FIG. 2, the furan of formula (M) may be produced from haloalkylfurfurals. Haloalkylfurfurals, such as 5-(chloromethyl)furfural, may be obtained from biomass, a renewable source. Thus, the furans of formula (M) may be obtained from renewable sources.

In certain aspects, the furan of formula (M) may be produced by:
combining a furan of formula (A) with a compound of formula (II) having the structure of either N≡CH or N≡C⁻ to produce a furan of formula (M).

In some variations, $R^1$ and $R^2$ are H. Thus, in some variations, the furan of formula (A) is:

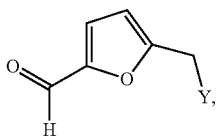

wherein Y is halo.

In one variation, Y is chloro. Thus, in one variation, the furan of formula (A) is:

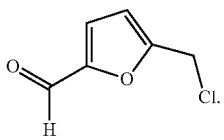

In another variation, Y is bromo. In yet another variation Y is fluoro. In yet another variation Y is iodo.

Reactors and Vessels

The methods described herein may be carried out batch-wise or continuously. The methods described herein may be performed in any suitable reactors, including open or closed reactors, that can contain the chemical reactions described herein. Suitable reactors may include, for example, a fed-batch stirred reactor, a batch stirred reactor, a continuous flow stirred reactor, a continuous plug-flow column reactor, an attrition reactor, a fluidized bed reactor. The reactor may include a continuous mixer, such as a screw mixer.

Additionally, the reactor may allow for addition and removal of certain components in the reaction mixture. For example, the reactor can have one or more outlets to add additional solvent or acid, or to remove the organic or aqueous phase from the reaction mixture. In some embodiments, the reactor may have one or more outlets that connecting the reactor to an isolation vessel, where the organic phase can be transferred from the reactor to the isolation vessel.

The reactors and vessels used herein may be generally made up of materials that are capable of withstanding the physical and chemical forces exerted during the methods described herein. In some embodiments, such materials used are capable of tolerating high concentrations of strong liquid acids. For example, the reactors and vessels may be made up of glass, metal or pyrex.

Isolation and Purification

The methods described herein may further include isolating and/or purifying the compounds of formulae (AB), (B), (B-I), (B-IIa), (B-IIb), (B-III), (C), (C-I), (M), (MN), (N), (N-I), (N-IIa), (N-IIb), (P), (P-I), (Q), and/or (R). Any methods known in the art may be employed to isolate and/or purify such compounds. For example, such compounds of formulae (AB), (B), (B-I), (B-IIa), (B-IIb), (B-III), (C), (C-I), (M), (MN), (N), (N-I), (N-IIa), (N-IIb), (P), (P-I), (Q), and/or (R) may be isolated and/or purified by distillation. In another example, such compounds of formulae (AB), (B), (B-I), (B-IIa), (B-IIb), (B-III), (C), (C-I), (M), (MN), (N), (N-I), (N-IIa), (N-IIb), (P), (P-I), (Q), and/or (R) may be isolated by distillation, and the isolated compound(s) may be further purified by chromatography.

It should be understood that in certain variations, the compounds of formulae (AB), (B), (B-I), (B-IIa), (B-IIb), (B-III), (C), (C-I), (M), (MN), (N), (N-I), (N-IIa), (N-IIb), (P), (P-I), (Q), and/or (R). produced is/are not isolated and/or purified, and may be further used in one or more downstream reactions described herein.

Yield, Conversion and Selectivity

The yield of a product takes into account the conversion of the starting materials into the product, and the selectivity for the product over other products that may be formed.

The difference between yield, conversion and selectivity is explained in the examples provided herein. For example, with respect to the conversion of a compound of formula (A) into a compound of formula (C), the reaction can be generalized as follows, where "A" represents the moles of the compound of formula (A); and "C" represents the moles of the compound of formula (C); and "a" and "c" are stoichiometric coefficients.

$$aA \rightarrow cC$$

Conversion of A is the percentage of reactant A that has been consumed during the reaction shown above, as expressed by the following equation:

$$\% \text{ Conversion} = \frac{Ao - Af}{Ao} * 100\%,$$

where $A_o$ is the initial number of moles of reactant A; and $A_f$ is the final number of moles of reactant A.

Selectivity is the stoichiometrically relative amount of product C produced from the converted amount of reactant A, as expressed as a percentage by the following equation:

$$\text{Selectivity (\%)} = \frac{Cf * \frac{a}{c}}{Ao - Af} * 100\%,$$

where $A_o$ is the starting moles of reactant A; $A_f$ is the final number of moles of reactant A; and $C_f$ is the number of moles of product C. In some embodiments where "a/c"=1, and the equation can be simplified to:

$$\text{Selectivity (\%)} = \frac{Cf}{Ao - Af} * 100\%.$$

The yield of product C is the percentage of reactant A that is converted into product C, as expressed by the following equation:

Yield (%)=Conversion (%)*Selectivity (%)

In certain embodiments, the methods described herein have a yield of at least 10%, at least 15%, at least 20%, at least 30%, at least 40%, at least 50%, at least 60%, at least 70%, at least 75%, at least 80%, at least 85%, at least 90%, at least 95%, or at least 99% by weight. In other embodiments, the yield is between 10% to 100%, between 10% to 90%, between 15% to 100%, between 15% to 90%, between 20% to 80%, between 30% to 80%, between 40% to 80%, between 50%-80%, or between 60%-80% by weight.

In certain embodiments, the methods described herein have a selectivity of at least 10%, at least 20%, at least 30%, at least 40%, at least 50%, at least 60%, at least 70%, at least 80%, at least 90%, or at least 99%. In other embodiments, the selectivity is between 40% to 99%, between 40% to 95%, between 40% to 90%, between 40% to 80%, between 50% to 99%, between 50% to 95%, between 50% to 90%, between 50% to 80%, between 60% to 99%, between 60% to 95%, between 60% to 90%, between 60% to 80%, between 70% to 99%, between 70% to 95%, between 70% to 90%, or between 70% to 80%.

Downstream Products

The diamine compounds produced according to the methods described herein, including, for example, the (phenylene)dialkanamines of formula (C-I), the alkyldiamines of formula (B-III), the furans of formula (B-IIa), the tetrahydrofurans of formula (B-IIb), the tetrahydrofurans of formula (N-IIb), the furans of formula (N-IIa), and the (phenylene)dialkanamines of formula (P-I) may be suitable for the manufacture of specialty polymers and other polymers.

Thus, in some aspects, provided is a method that includes polymerizing a (phenylene)dialkanamine of formula (C-I), an alkyldiamine of formula (B-III), a furan of formula (B-IIa), a tetrahydrofuran of formula (B-IIb), a furan of formula (N-IIa), a tetrahydrofuran of formula (N-IIb), or a (phenylene)dialkanamine of formula (P-I), or any combinations thereof, produced according to the methods described herein. In other aspects, provided is a polymer produced by polymerizing a (phenylene)dialkanamine of formula (C-I), an alkyldiamine of formula (B-III), a furan of formula (B-IIa), a tetrahydrofuran of formula (B-IIb), a furan of formula (N-IIa), a tetrahydrofuran of formula (N-IIb), or a (phenylene)dialkanamine of formula (P-I), or any combinations thereof, produced according to the methods described herein. In some variations, the polymer is nylon.

In certain aspects, provided is a method to produce nylon from octamethylene diamine (also referred to as octane-1, 8-diamine), which is an example of a compound of formula (B-III). In one variation, the method includes combining octamethylene diamine and an acid (e.g., a diacid, such as adipic acid) to produce a polymer such as nylon.

In some variations, a polymer manufactured using one or more of the compounds produced according to the methods described herein may be combined with one or more additional compounds. For example, in some embodiments, the polymer is combined with one or more plasticizers, colorants, fillers, or stabilizers, or any combinations thereof. Stabilizers may include, for example, antioxidants and UV absorbers.

"Alkyl" refers to a monoradical unbranched or branched saturated hydrocarbon chain. In some embodiments, for example of formulae (AB), (B), (B-I), (B-IIa), (B-IIb), (B-III), (C), (C-I), (M), (MN), (N), (N-I), (N-IIa), (N-IIb), (P), (P-I), (Q), and/or (R), alkyl as used herein has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl and t-butyl; "propyl" can include n-propyl and isopropyl. Further, it should be understood that when a range of values is listed, it is intended to encompass each value and sub-range within the range. For example, "$C_{1-6}$ alkyl" (which may also be referred to as 1-6C alkyl, C1-C6 alkyl, or C1-6 alkyl) is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

Enumerated Embodiments

The following enumerated embodiments are representative of some aspects of the invention.

1. A method comprising: reducing a furan of formula (B) to produce a furan of formula (B-I), a furan of formula (B-IIa), a tetrahydrofuran of formula (B-IIb), an alkyldiamine of formula (B-III), or any mixtures thereof, wherein:
the furan of formula (B) is:

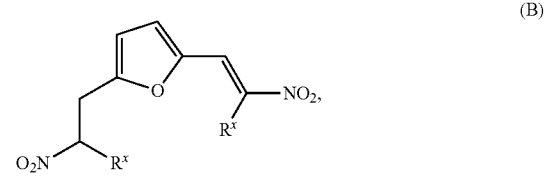

(B)

wherein $R^x$ is H or alkyl;
the furan of formula (B-I) is:

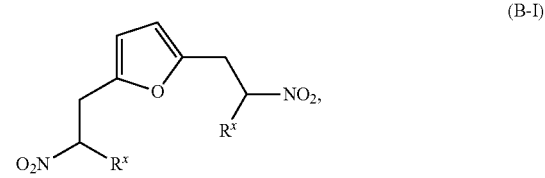

(B-I)

wherein $R^x$ is as defined for formula (B) above;
the furan of formula (B-IIa) is:

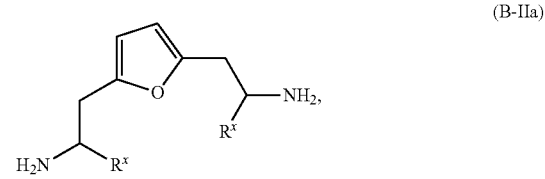

(B-IIa)

wherein $R^x$ is as defined for formula (B) above;
the tetrahydrofuran of formula (B-IIb) is:

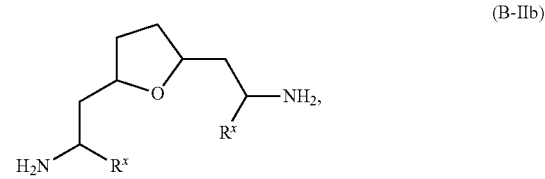

(B-IIb)

wherein $R^x$ is as defined for formula (B) above; and
the alkyldiamine of formula (B-III) is:

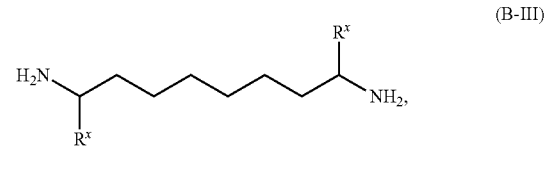

(B-III)

wherein $R^x$ is as defined for formula (B) above.

2. The method of embodiment 1, wherein $R^x$ is H.

3. The method of embodiment 1, wherein:

the furan of formula (B) is:

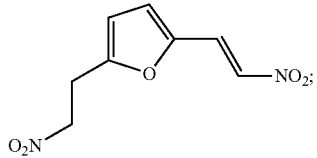 [SMILES: O=[N+]([O-])/C=C/c1ccc(CC[N+](=O)[O-])o1]

the furan of formula (B-I) is:

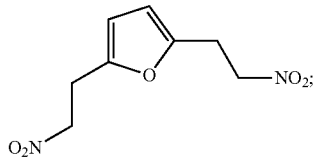

the furan of formula (B-IIa) is:

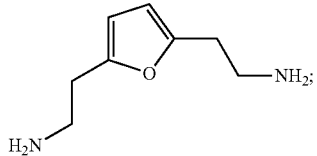

the tetrahydrofuran of formula (B-IIb) is:

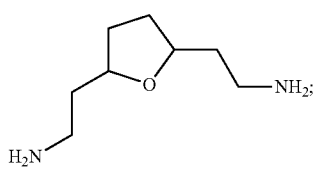

and the alkyldiamine of formula (B-III) is:

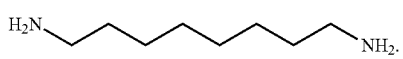

4. The method of any one of embodiments 1 to 3, further comprising isolating the furan of formula (B-I), the furan of formula (B-IIa), the tetrahydrofuran of formula (B-IIb), or the alkyldiamine of formula (B-III), or any mixtures thereof.

5. The method of any one of embodiments 1 to 4, further comprising:

combining the furan of formula (B-I), ethylene and catalyst to form a reaction mixture; and producing a compound of formula (C) from at least a portion of the furan of formula (B-I) and ethylene in the reaction mixture, wherein:

the compound of formula (C) is:

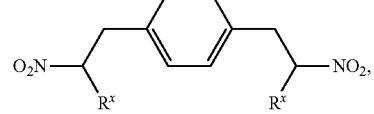

wherein $R^x$ is as defined for formula (B-I) above.

6. The method of embodiment 5, wherein:

the compound of formula (C) is:

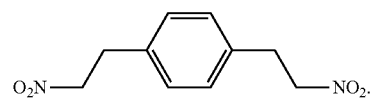

7. The method of embodiment 5 or 6, further comprising:

reducing the compound of formula (C) to produce a compound of formula (C-I), wherein:

the compound of formula (C-I) is:

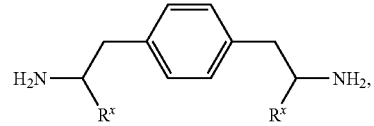

wherein $R^x$ is as defined for formula (C) above.

8. The method of any one of embodiments 1 to 4, further comprising:

combining the furan of formula (B-IIa), ethylene and catalyst to form a reaction mixture; and producing a compound of formula (C-I) from at least a portion of the furan of formula (B-IIa) and ethylene in the reaction mixture, wherein:

the compound of formula (C-I) is:

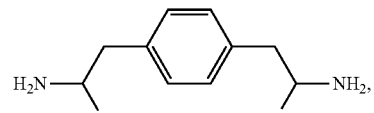

wherein $R^x$ is as defined for formula (B-IIa) above.

9. The method of embodiment 7 or 8, wherein:

the compound of formula (C-I) is:

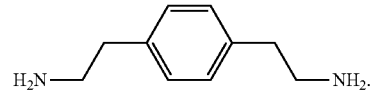

10. The method of any one of embodiments 6 to 9, further comprising isolating the compound of formula (C-I).

11. The method of any one of embodiments 1 to 10, further comprising:
combining a furan of formula (A) with a nitroalkane of formula (I) to produce the furan of formula (B), wherein:
the furan of formula (A) is:

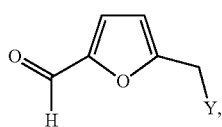

(A)

wherein Y is halo; and
the nitroalkane of formula (I) is:

(I), wherein $R^x$ is as defined for formula (B) above.

12. The method of embodiment 11, wherein the furan of formula (A) is combined with the nitroalkane of formula (I) in the presence of base and optionally solvent.

13. A method of producing 2,2'-(1,4-phenylene)diethanamine, comprising:
reducing 2-(2-nitroethyl)-5-(2-nitrovinyl)furan to produce 2,5-bis(2-nitroethyl)furan;
combining the 2,5-bis(2-nitroethyl)furan with ethylene and catalyst to form a reaction mixture;
producing 1,4-bis(2-nitroethyl)benzene from at least a portion of the 2,5-bis(2-nitroethyl)furan and the ethylene in the reaction mixture; and
reducing the 1,4-bis(2-nitroethyl)benzene to produce the 2,2'-(1,4-phenylene)diethanamine.

14. A method of producing 2,2'-(1,4-phenylene)diethanamine, comprising:
reducing 2-(2-nitroethyl)-5-(2-nitrovinyl)furan to produce 2,2'-(furan-2,5-diyl)diethanamine;
combining the 2,2'-(furan-2,5-diyl)diethanamine with ethylene and catalyst to form a reaction mixture;
producing the 2,2'-(1,4-phenylene)diethanamine from at least a portion of the 2,2'-(furan-2,5-diyl)diethanamine and the ethylene in the reaction mixture.

15. A method of producing octane-1,8-diamine, comprising:
reducing 2-(2-nitroethyl)-5-(2-nitrovinyl)furan to produce the octane-1,8-diamine.

16. The method of any one of embodiments 13 to 15, further comprising combining 5-(halomethyl)furfural with nitromethane to produce the 2-(2-nitroethyl)-5-(2-nitrovinyl)furan.

17. The method of embodiment 16, wherein the 5-(halomethyl)furfural is combined with the nitromethane in the presence of base and optionally solvent.

18. A method of producing 2,2'-(tetrahydrofuran-2,5-diyl)diethanamine, comprising:
reducing 2-(2-nitroethyl)-5-(2-nitrovinyl)furan to produce 2,2'-(tetrahydrofuran-2,5-diyl)diethanamine.

19. A method of producing 2,2'-(furan-2,5-diyl)diethanamine, comprising:
reducing 2-(5-(2-nitrovinyl)furan-2-yl)acetonitrile to produce 2,2'-(furan-2,5-diyl)diethanamine.

20. The method of embodiment 19, further comprising:
converting 2-(5-formylfuran-2-yl)acetonitrile to produce the 2-(5-(2-nitrovinyl)furan-2-yl)acetonitrile.

21. The method of embodiment 20, further comprising:
combining 5-(chloromethyl)furfural with N≡CH or N≡C⁻ to produce the 2-(5-formylfuran-2-yl)acetonitrile.

22. The method of embodiment 19, further comprising:
combining 2-(chloromethyl)-5-(2-nitrovinyl)furan with N≡CH or N≡C⁻ to produce the 2-(5-(2-nitrovinyl)furan-2-yl)acetonitrile.

23. A method comprising: reducing a furan of formula (N) to produce a furan of formula (N-I), wherein:
the furan of formula (N) is:

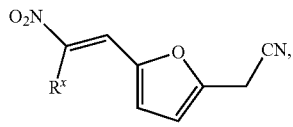

(N)

wherein $R^x$ is H or alkyl; and
the furan of formula (N-I) is:

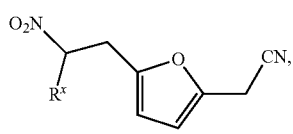

(N-I)

wherein $R^x$ is as defined for formula (N) above.

24. The method of embodiment 23, further comprising: combining the furan of formula (N-I) with ethylene to produce a compound of formula (P), wherein:
the compound of formula (P) is:

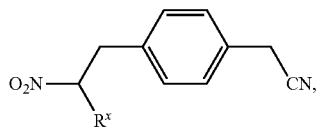

(P)

wherein $R^x$ is as defined for formula (N-I).

25. The method of embodiment 24, further comprising: reducing the compound of formula (P) to produce a compound of formula (P-I), wherein:
the compound of formula (P-I) is:

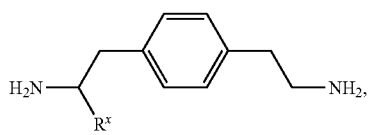

(P-I)

wherein $R^x$ is as defined for formula (P).

26. The method of embodiment 24 or 25, wherein:
the furan of formula (N-I) is:

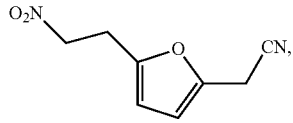 [SMILES: N#CCc1ccc(CC[N+](=O)[O-])o1]

and
the compound of formula (P) is:

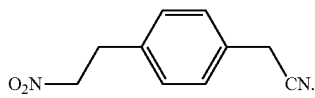

27. The method of embodiment 25 or 26, wherein:
the compound of formula (P-I) is:

28. A method comprising: combining a furan of formula (A) with a nitroalkane of formula (I) to produce a furan of formula (Q), wherein:
the furan of formula (A) is:

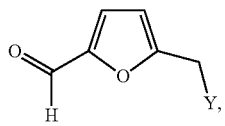 (A)

wherein Y is halo;
the nitroalkane of formula (I) is:

(R$^x$CH$_2$)NO$_2$ (I), wherein R$^x$ is H or alkyl; and
the furan of formula (Q) is:

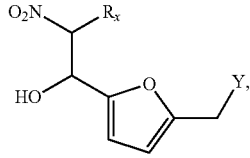 (Q)

wherein Y is as defined for formula (A) above, and R$^x$ is as defined for formula (I) above.

29. The method of embodiment 28, further comprising: converting the furan of formula (Q) to produce the furan of formula (R), wherein:
the furan of formula (R) is:

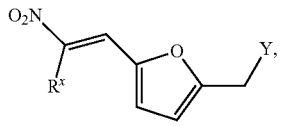 (R)

wherein Y and R$^x$ are as defined for formula (Q) above.

30. A method comprising: converting a furan of formula (Q) to produce the furan of formula (R), wherein:
the furan of formula (Q) is:

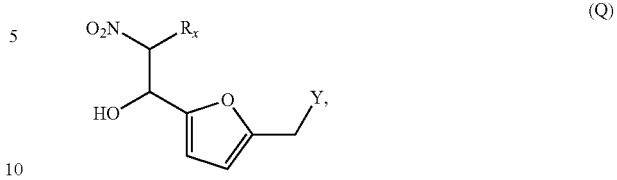 (Q)

wherein:
Y is halo; and
R$^x$ is H or alkyl; and
the furan of formula (R) is:

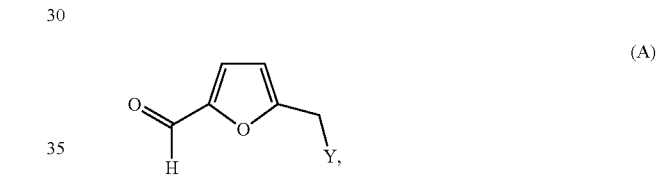 (R)

wherein Y and R$^x$ are as defined for formula (Q) above.

31. A method comprising: combining a furan of formula (A) with a nitroalkane of formula (I) and base to produce a furan of formula (R), wherein:
the furan of formula (A) is:

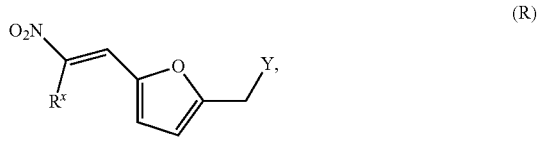 (A)

wherein Y is halo;
the nitroalkane of formula (I) is:

(R$^x$CH$_2$)NO$_2$ (I), wherein R$^x$ is H or alkyl; and
the furan of formula (R) is:

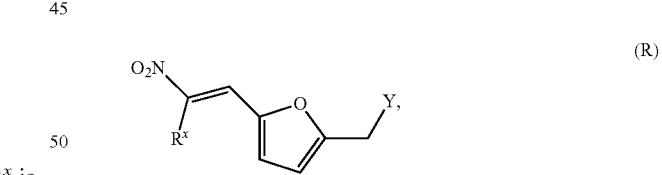 (R)

wherein Y is as defined for formula (A) above and R$^x$ is as defined for formula (I) above.

32. The method of any one of embodiments 28, 29, or 31, wherein
the furan of Formula (A) is:

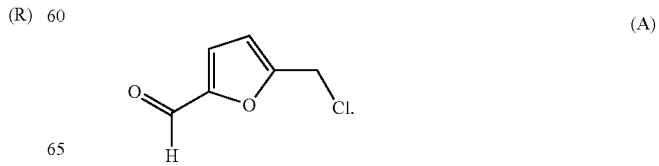 (A)

33. The method of any one of embodiments 28 to 30, or 32, wherein:
the furan of formula (Q) is:

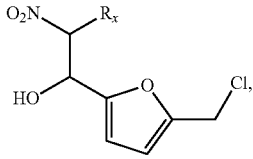
(Q)

wherein $R^x$ is as defined for formula (I).

34. The method of any one of embodiments 29 to 33, wherein:
the furan of formula (R) is:

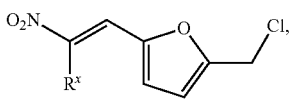
(R)

wherein $R^x$ is as defined for formula (I).

35. A method comprising: combining a furan of formula (A) with a nitroalkane of formula (I), base, and N≡CH or N≡C⁻ to produce a furan of formula (N), wherein:
the furan of formula (A) is:

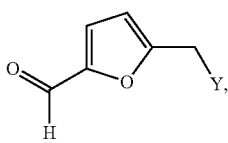
(A)

wherein Y is halo;
the nitroalkane of formula (I) is:

(R$^x$CH$_2$)NO$_2$ (I), wherein $R^x$ is H or alkyl; and
the furan of formula (N) is:

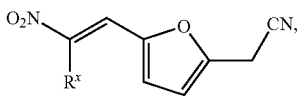
(N)

wherein $R^x$ is as defined for formula (I) above.

36. A method comprising: reducing a furan of formula (N) to produce a furan of formula (N-IIa) or a tetrahydrofuran of formula (N-IIb), or a combination thereof, wherein:
the furan of formula (N) is:

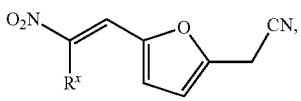
(N)

wherein $R^x$ is H or alkyl;
the furan of formula (N-IIa) is:

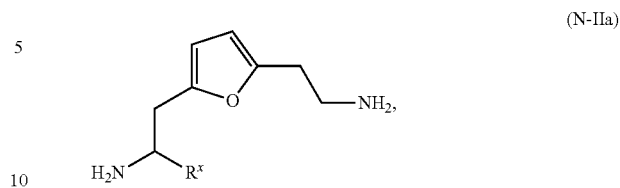
(N-IIa)

wherein $R^x$ is as defined for formula (N) above; and
the tetrahydrofuran of formula (N-IIb) is:

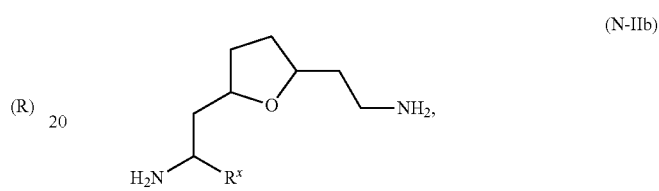
(N-IIb)

wherein $R^x$ is as defined for formula (N) above.

37. The method of embodiment 36, further comprising:
combining a furan of formula (A) with a nitroalkane of formula (I), base, and N≡CH or N≡C⁻ to produce the furan of formula (N), wherein:
the furan of formula (A) is:

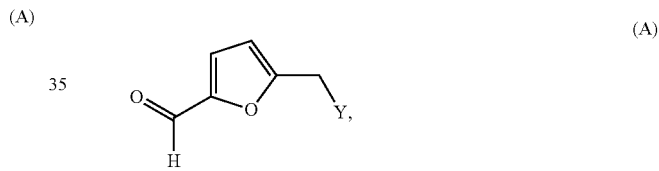
(A)

wherein Y is halo; and
the nitroalkane of formula (I) is:

(R$^x$CH$_2$)NO$_2$ (I), wherein $R^x$ is H or alkyl.

38. A method comprising: combining a furan of formula (A) with a nitroalkane of formula (I) and base to produce a furan of formula (R), wherein:
the furan of formula (A) is:

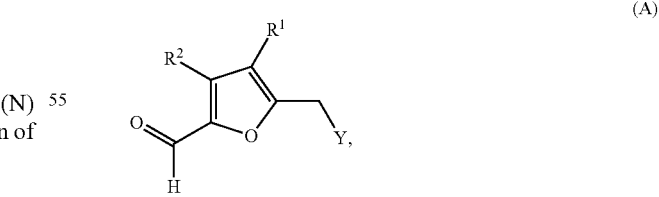
(A)

wherein:
Y is halo; and
$R^1$ and $R^2$ are independently H or alkyl;
the nitroalkane of formula (I) is:

(R$^x$CH$_2$)NO$_2$ (I), wherein $R^x$ is H or alkyl; and the furan of formula (R) is:

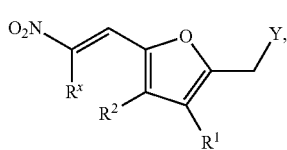

(R)

wherein Y, R¹ and R² are as defined for formula (A) above and $R^x$ is as defined for formula (I) above.

39. A method comprising: combining a furan of formula (A) with a nitroalkane of formula (I), base, and N≡CH or N≡C⁻ to produce a furan of formula (N), wherein:

the furan of formula (A) is:

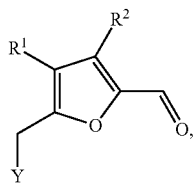

(A)

wherein Y is halo;
the nitroalkane of formula (I) is:

$(R^xCH_2)NO_2$     (I), wherein $R^x$ is H or alkyl; and
the furan of formula (N) is:

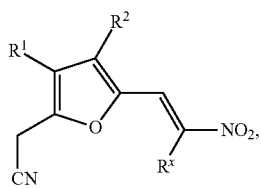

(N)

wherein $R^x$ is as defined for formula (I) above.

40. A method comprising: reducing a furan of formula (N) to produce a furan of formula (N-IIa) or a tetrahydrofuran of formula (N-IIb), or a combination thereof, wherein:

the furan of formula (N) is:

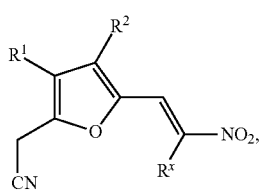

(N)

wherein R¹, R² and $R^x$ are independently H or alkyl;

the furan of formula (N-IIa) is:

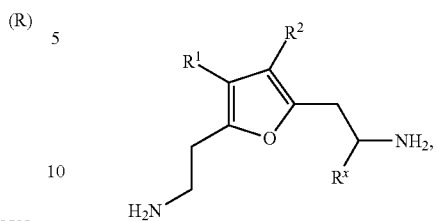

(N-IIa)

wherein R¹, R² and $R^x$ are as defined for formula (N) above; and the tetrahydrofuran of formula (N-IIb) is:

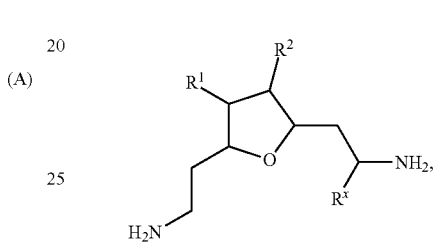

(N-IIb)

wherein R¹, R² and $R^x$ are as defined for formula (N) above.

41. A method comprising: reducing a furan of formula (B) to produce a furan of formula (B-IIa), a tetrahydrofuran of formula (B-IIb), or a mixture thereof, wherein:

the furan of formula (B) is:

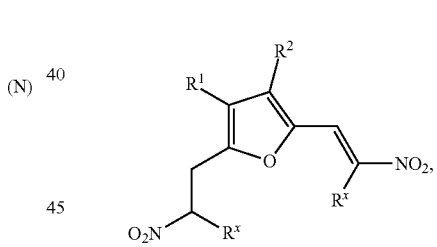

(B)

wherein:
$R^x$ is H or alkyl; and
R¹ and R² are independently H or alkyl;
the furan of formula (B-IIa) is:

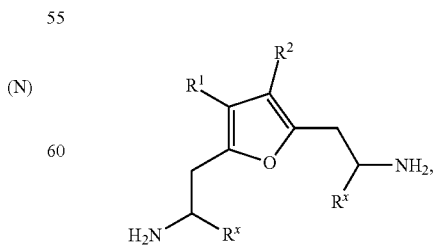

(B-IIa)

wherein $R^x$, R¹ and R² are as defined for formula (B) above; and the tetrahydrofuran of formula (B-IIb) is:

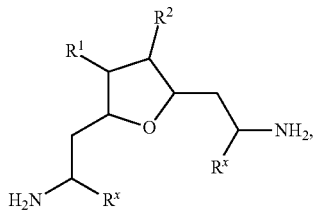
(B-IIb)

wherein $R^x$, $R^1$ and $R^2$ are as defined for formula (B) above.

42. A method comprising: reducing a furan of formula (N) to produce a furan of formula (B-IIa), a tetrahydrofuran of formula (B-IIb), or a mixture thereof, wherein:
the furan of formula (N) is:

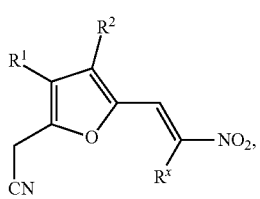
(N)

wherein $R^1$, $R^2$ and $R^x$ are independently H or alkyl;
the furan of formula (B-IIa) is:

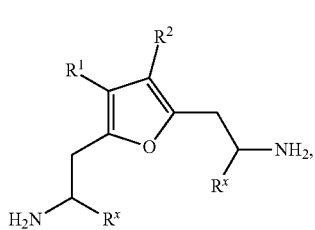
(B-IIa)

wherein $R^x$, $R^1$ and $R^2$ are as defined for formula (N) above; and
the tetrahydrofuran of formula (B-IIb) is:

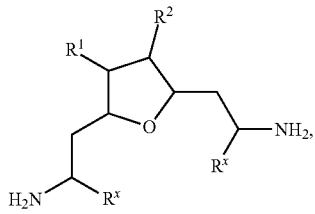
(B-IIb)

wherein $R^x$, $R^1$ and $R^2$ are as defined for formula (N) above.

43. A method comprising: reducing a furan of formula (N) to produce a furan of formula (N-I), wherein:
the furan of formula (N) is:

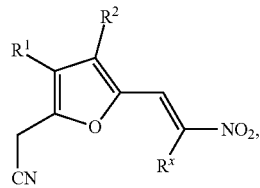
(N)

wherein $R^1$, $R^2$ and $R^x$ are independently H or alkyl;
the furan of formula (N-I) is:

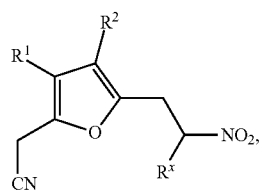
(N-I)

wherein $R^1$, $R^2$ and $R^x$ are as defined for formula (N) above.

44. A method comprising: reducing a furan of formula (B) to produce a furan of formula (B-I), a furan of formula (B-IIa), a tetrahydrofuran of formula (B-IIb), an alkyldiamine of formula (B-III), or any combinations thereof, wherein:
the furan of formula (B) is:

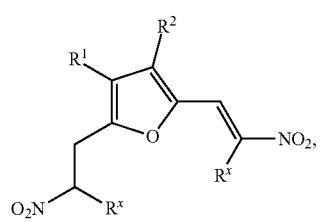
(B)

wherein:
$R^x$ is H or alkyl; and
$R^1$ and $R^2$ are independently H or alkyl;
the furan of formula (B-I) is:

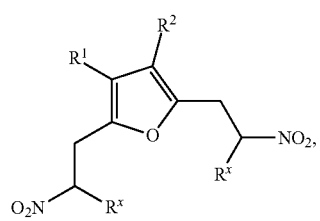
(B-I)

wherein $R^x$, $R^1$ and $R^2$ are as defined for formula (B) above;

the furan of formula (B-IIa) is:

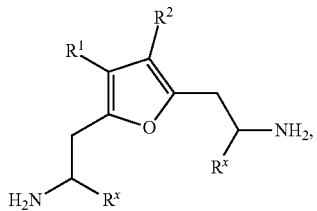
(B-IIa)

wherein $R^x$, $R^1$ and $R^2$ are as defined for formula (B) above;

the tetrahydrofuran of formula (B-IIb) is:

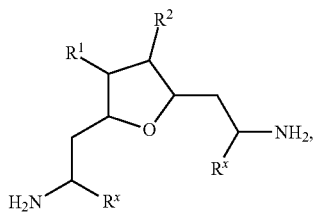
(B-IIb)

wherein $R^x$, $R^1$ and $R^2$ are as defined for formula (B) above;

the alkyldiamine of formula (B-III) is:

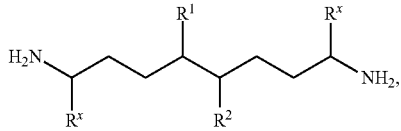
(B-III)

wherein $R^x$, $R^1$ and $R^2$ are as defined for formula (B) above.

45. The method of embodiment 44, further comprising:

combining the furan of formula (B-I), ethylene and catalyst to form a reaction mixture; and producing a compound of formula (C) from at least a portion of the furan of formula (B-I) and ethylene in the reaction mixture, wherein:

the compound of formula (C) is:

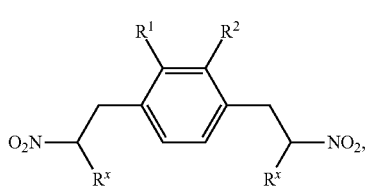
(C)

wherein $R^x$, $R^1$ and $R^2$ are as defined for formula (B-I) above.

46. The method of embodiment 45, further comprising:

reducing the compound of formula (C) to produce a compound of formula (C-I), wherein:

the compound of formula (C-I) is:

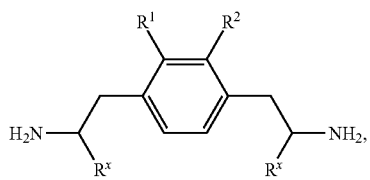
(C-I)

wherein $R^x$, $R^1$ and $R^2$ are as defined for formula (C) above.

47. The method of embodiment 44, further comprising:

combining the furan of formula (B-IIa), ethylene and catalyst to form a reaction mixture; and producing a compound of formula (C-I) from at least a portion of the furan of formula (B-IIa) and ethylene in the reaction mixture, wherein:

the compound of formula (C-I) is:

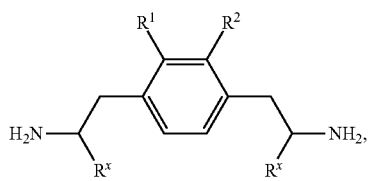
(C-I)

wherein $R^x$, $R^1$ and $R^2$ are as defined for formula (B-IIa) above.

48. The method of any one of embodiments 44 to 47, further comprising:

combining a furan of formula (A) with a nitroalkane of formula (I) to produce the furan of formula (B), wherein:

the furan of formula (A) is:

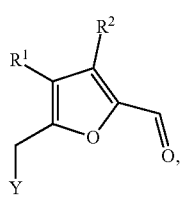
(A)

wherein:
Y is halo; and
$R^1$ and $R^2$ are independently H or alkyl; and the nitroalkane of formula (I) is:

$(R^xCH_2)NO_2$ (I), wherein $R^x$ is as defined for formula (B) above.

49. The method of embodiment 48, wherein the furan of formula (A) is combined with the nitroalkane of formula (I) in the presence of base and optionally solvent.

50. A method comprising: reducing a furan of formula (N) to produce a furan of formula (N-I), wherein:
the furan of formula (N) is:

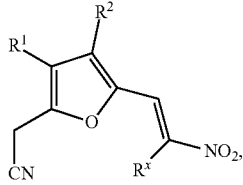

(N)

wherein:
$R^x$ is H or alkyl; and
$R^1$ and $R^2$ are independently H or alkyl; and
the furan of formula (N-I) is:

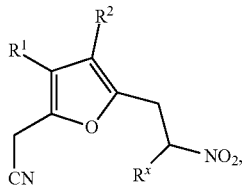

(N-I)

wherein $R^x$, $R^1$ and $R^2$ are as defined for formula (N) above.

51. The method of embodiment 50, further comprising: combining the furan of formula (N-I) with ethylene to produce a compound of formula (P), wherein:
the compound of formula (P) is:

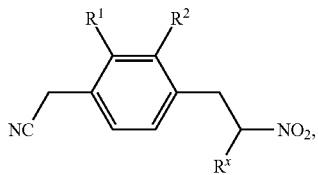

(P)

wherein $R^x$, $R^1$ and $R^2$ are as defined for formula (N-I).

52. The method of embodiment 51, further comprising: reducing the compound of formula (P) to produce a compound of formula (P-I), wherein:
the compound of formula (P-I) is:

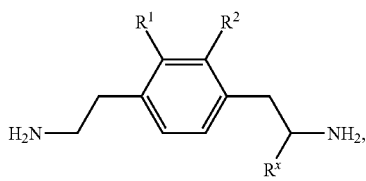

(P-I)

wherein $R^x$, $R^1$ and $R^2$ are as defined for formula (P).

53. A method comprising: combining a furan of formula (A) with a nitroalkane of formula (I) to produce a furan of formula (Q), wherein:

the furan of formula (A) is:

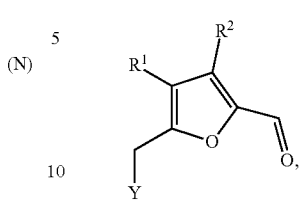

(A)

wherein:
Y is halo; and
$R^1$ and $R^2$ are independently H or alkyl;
the nitroalkane of formula (I) is:

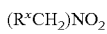

(I), wherein $R^x$ is H or alkyl; and
the furan of formula (Q) is:

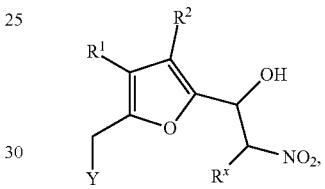

(Q)

wherein Y, $R^1$ and $R^2$ are as defined for formula (A) above, and $R^x$ is as defined for formula (I) above.

54. The method of embodiment 53, further comprising: converting the furan of formula (Q) to produce a furan of formula (R), wherein:
the furan of formula (R) is:

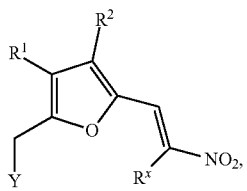

(R)

wherein Y, $R^1$, $R^2$ and $R^x$ are as defined for formula (Q) above.

55. A method comprising: converting a furan of formula (Q) to produce the furan of formula (R), wherein:
the furan of formula (Q) is:

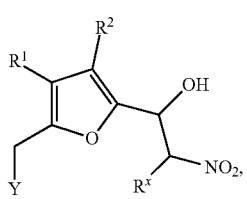

(Q)

wherein:
Y is halo;
$R^x$ is H or alkyl; and
$R^1$ and $R^2$ are independently H or alkyl; and
the furan of formula (R) is:

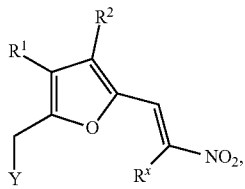

(R)

wherein Y, $R^1$, $R^2$ and $R^x$ are as defined for formula (Q) above.

56. A method comprising: combining a furan of formula (A) with a nitroalkane of formula (I) and base to produce a furan of formula (Q), wherein:
the furan of formula (A) is:

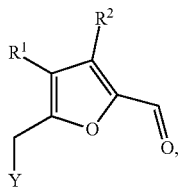

(A)

Y is halo; and
$R^1$ and $R^2$ are independently H or alkyl;
the nitroalkane of formula (I) is:

$(R^xCH_2)NO_2$  (I), wherein $R^x$ is H or alkyl; and
the furan of formula (Q) is:

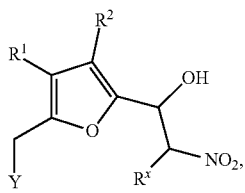

(Q)

wherein Y, $R^1$ and $R^2$ are as defined for formula (A) above and $R^x$ is as defined for formula (I) above.

57. A method comprising: combining a furan of formula (A) with a nitroalkane of formula (I), base, and N≡CH or N≡C⁻ to produce a furan of formula (N), wherein:
the furan of formula (A) is:

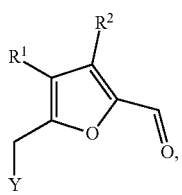

(A)

Y is halo; and
$R^1$ and $R^2$ are independently H or alkyl;

the nitroalkane of formula (I) is:

$(R^xCH_2)NO_2$  (I), wherein $R^x$ is H or alkyl; and
the furan of formula (N) is:

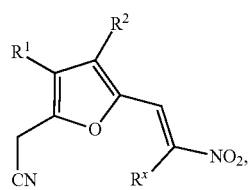

(N)

wherein Y, $R^1$ and $R^2$ are as defined for formula (A) above and $R^x$ is as defined for formula (I) above.

58. A method comprising: reducing a furan of formula (N) to produce a furan of formula (B-IIa), a tetrahydrofuran of formula (B-IIb), or a mixture thereof, wherein:
the furan of formula (N) is:

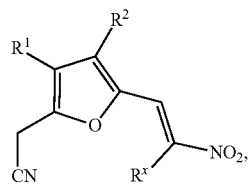

(N)

wherein $R^1$, $R^2$ and $R^x$ are independently H or alkyl;
the furan of formula (B-IIa) is:

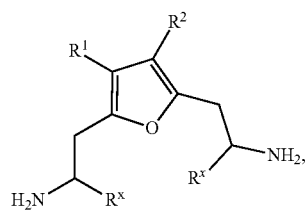

(B-IIa)

wherein $R^x$, $R^1$ and $R^2$ are as defined for formula (N) above; and the tetrahydrofuran of formula (B-IIb) is:

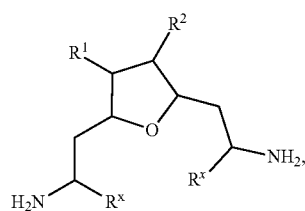

(B-IIb)

wherein $R^x$, $R^1$ and $R^2$ are as defined for formula (N) above.

59. The method of embodiment 58, further comprising:
combining a furan of formula (A) with a nitroalkane of formula (I), base, and N≡CH or N≡C⁻ to produce the furan of formula (N), wherein:
the furan of formula (A) is:

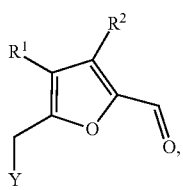

(A)

wherein:
Y is halo; and
R¹ and R² are independently H or alkyl; and
the nitroalkane of formula (I) is:

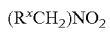 (I), wherein R$^x$ is H or alkyl.

60. A method comprising: combining a furan of formula (A) with a nitroalkane of formula (I) and base to produce a furan of formula (AB), wherein:
the furan of formula (A) is:

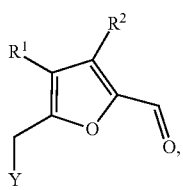

(A)

Y is halo; and
R¹ and R² are independently H or alkyl;
the nitroalkane of formula (I) is:

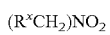 (I), wherein R$^x$ is H or alkyl; and
the furan of formula (AB) is:

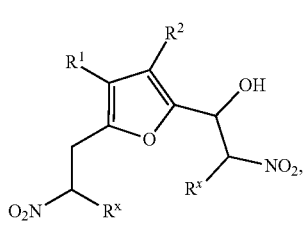

(AB)

wherein:
R$^x$ is H or alkyl; and
R¹ and R² are independently H or alkyl.

61. The method of embodiment 60, further comprising converting the furan of formula (AB) to a furan of formula (B), wherein:

the furan of formula (B) is:

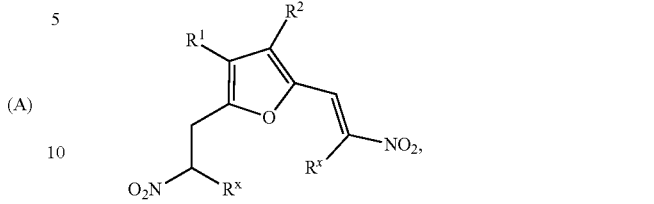

(B)

wherein:
R$^x$ is H or alkyl; and
R¹ and R² are independently H or alkyl;

62. A method comprising: combining a furan of formula (M) with a nitroalkane of formula (I) and base to produce a furan of formula (MN), wherein:
the furan of formula (M) is:

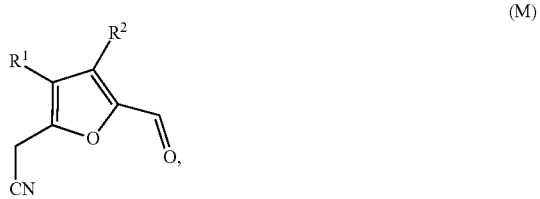

(M)

wherein R¹ and R² are independently H or alkyl;
the nitroalkane of formula (I) is:

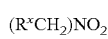 (I), wherein R$^x$ is H or alkyl; and
the furan of formula (MN) is:

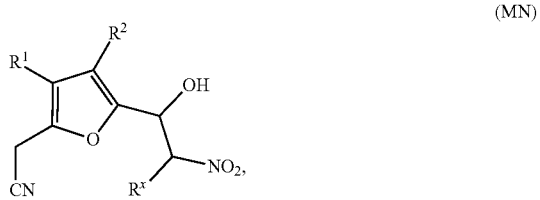

(MN)

wherein R¹, R², and R$^x$ are independently H or alkyl.

63. The method of embodiment 62, further comprising converting the furan of formula (MN) to a furan of formula (N), wherein:
the furan of formula (MN) is:

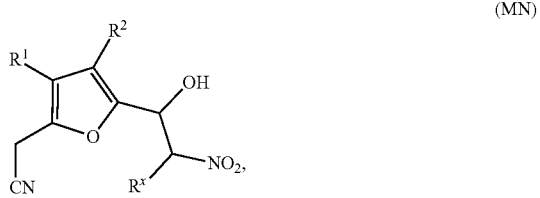

(MN)

wherein R¹, R², and R$^x$ are independently H or alkyl; and the furan of formula (N) is:

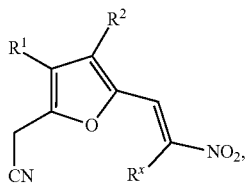
(N)

wherein:
R$^x$ is H or alkyl; and
R$^1$ and R$^2$ are independently H or alkyl.

64. A method comprising: converting a furan of formula (MN) to a furan of formula (N), wherein:
the furan of formula (MN) is:

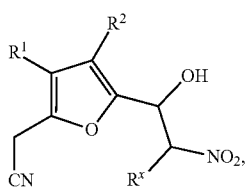
(MN)

wherein R$^1$, R$^2$, and R$^x$ are independently H or alkyl; and
the furan of formula (N) is:

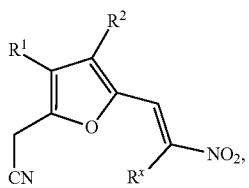
(N)

wherein:
R$^x$ is H or alkyl; and
R$^1$ and R$^2$ are independently H or alkyl.

65. The method of any one of embodiments 38 to 64, wherein R$^1$ and R$^2$ are H.
66. The method of any one of embodiments 38 to 64, wherein R$^x$ is H.
67. The method of any one of embodiments 38, 39, 43, 53 to 61, 65 or 66, wherein Y is chloro.
68. A compound of formula (AB), formula (B), formula (B-I), formula (B-IIa), formula (B-M), formula (B-III), formula (C), formula (C-I), formula (M), formula (MN), formula (N), formula (N-I), formula (N-IIa), formula (N-IIb), formula (P), formula (P-I), formula (Q), or formula (R), wherein:
the compound of formula (AB) is:

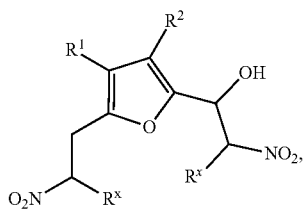
(AB)

wherein:
R$^x$ is H or alkyl; and
R$^1$ and R$^2$ are independently H or alkyl;
the compound of formula (B) is:

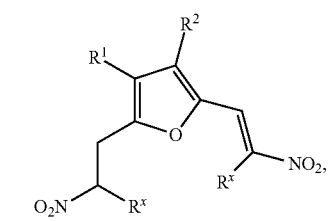
(B)

wherein:
R$^x$ is H or alkyl; and
R$^1$ and R$^2$ are independently H or alkyl;
the compound of formula (B-I) is:

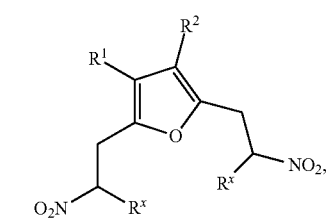
(B-I)

wherein:
R$^x$ is H or alkyl; and
R$^1$ and R$^2$ are independently H or alkyl;
the compound of formula (B-IIa) is:

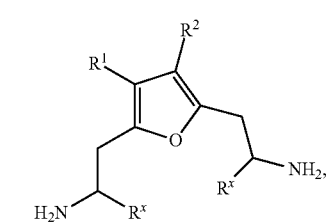
(B-IIa)

wherein:
R$^x$ is H or alkyl; and
R$^1$ and R$^2$ are independently H or alkyl;
the compound of formula (B-IIb) is:

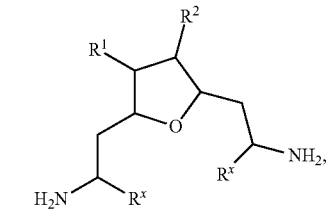
(B-IIb)

wherein:

R$^x$ is H or alkyl; and

R$^1$ and R$^2$ are independently H or alkyl;

the compound of formula (B-III) is:

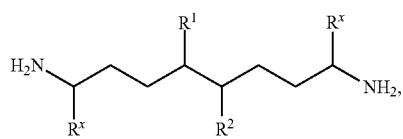
(B-III)

wherein:

R$^x$ is H or alkyl; and

R$^1$ and R$^2$ are independently H or alkyl;

the compound of formula (C) is:

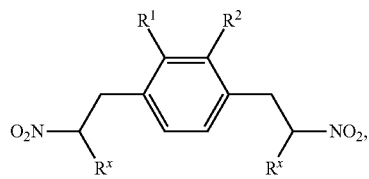
(C)

wherein:

R$^x$ is H or alkyl; and

R$^1$ and R$^2$ are independently H or alkyl;

provided at least one of R$^x$, R$^1$ and R$^2$ is alkyl;

the compound of formula (C-I) is:

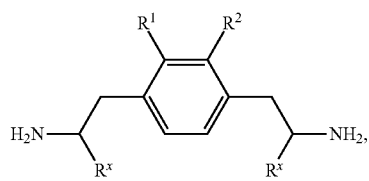
(C-I)

wherein:

R$^x$ is H or alkyl; and

R$^1$ and R$^2$ are independently H or alkyl;

the compound of formula (M) is:

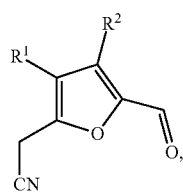
(M)

wherein R$^1$ and R$^2$ are independently H or alkyl;

provided at least one of R$^1$ and R$^2$ is alkyl;

the compound of formula (MN) is:

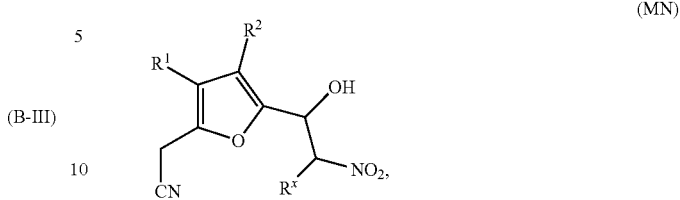
(MN)

wherein R$^1$, R$^2$, and R$^x$ are independently H or alkyl;

the compound of formula (N) is:

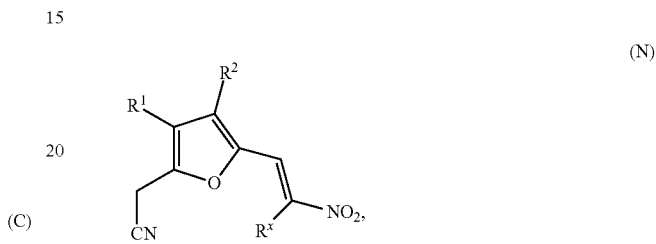
(N)

wherein R$^1$, R$^2$ and R$^x$ are independently H or alkyl;

the compound of formula (N-I) is:

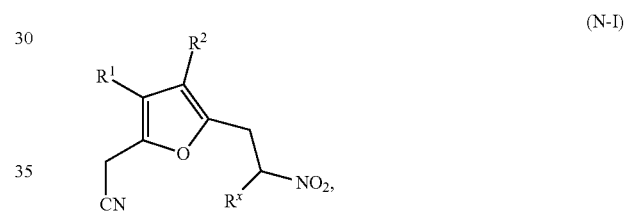
(N-I)

wherein R$^1$, R$^2$ and R$^x$ are independently H or alkyl;

the compound of formula (N-IIa) is:

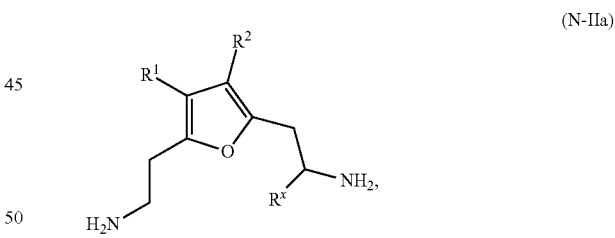
(N-IIa)

wherein R$^1$, R$^2$ and R$^x$ are independently H or alkyl;

the compound of formula (N-IIb) is:

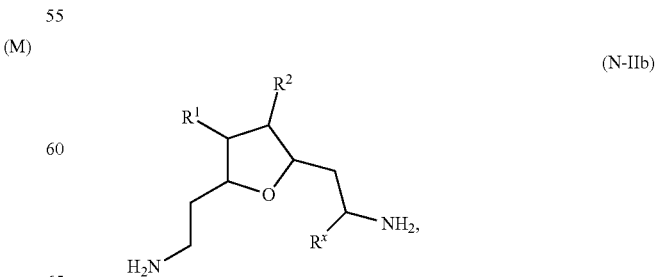
(N-IIb)

wherein R$^1$, R$^2$ and R$^x$ are independently H or alkyl;

the compound of formula (P) is:

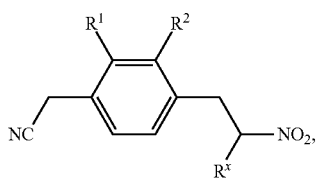
(P)

wherein $R^1$, $R^2$ and $R^x$ are independently H or alkyl;
the compound of formula (P-I) is:

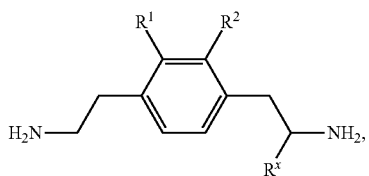
(P-I)

wherein $R^1$, $R^2$ and $R^x$ are independently H or alkyl;
the compound of formula (Q) is:

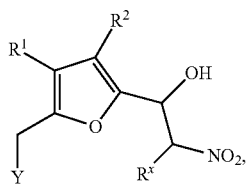
(Q)

wherein Y is halo; and
$R^1$, $R^2$ and $R^x$ are independently H or alkyl; and
the compound of formula (R) is:

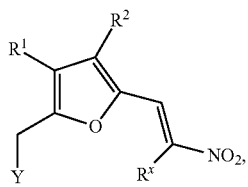
(R)

wherein Y is chloro; and
$R^1$, $R^2$ and $R^x$ are independently H or alkyl.

69. The compound of embodiment 68, wherein $R^1$ and $R^2$ are H.
70. The compound of embodiment 68 or 69, wherein $R^x$ is H.
71. A method of producing a polymer, comprising:
polymerizing one or more monomers of the compounds of any one of embodiments 68 to 70 to produce the polymer.
72. A composition, comprising
a polymerization catalyst; and
a compound of formula (AB), formula (B), formula (B-I), formula (B-IIa), formula (B-M), formula (B-III), formula (C), formula (C-I), formula (M), formula (MN), formula (N), formula (N-I), formula (N-IIa), formula (N-IIb), formula (P), formula (P-I), formula (Q), or formula (R), or any combinations thereof, wherein:
the compound of formula (AB) is:

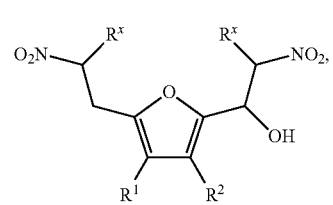
(AB)

wherein:
$R^x$ is H or alkyl; and
$R^1$ and $R^2$ are independently H or alkyl;
the compound of formula (B) is:

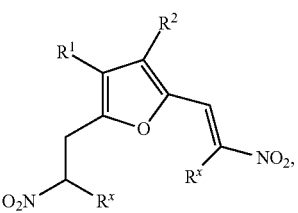
(B)

wherein $R^x$ is H or alkyl; and
$R^1$ and $R^2$ are independently H or alkyl;
the compound of formula (B-I) is:

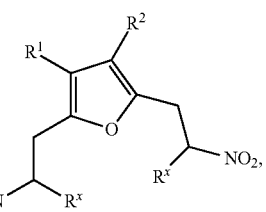
(B-I)

wherein $R^x$ is H or alkyl; and
$R^1$ and $R^2$ are independently H or alkyl;
the compound of formula (B-IIa) is:

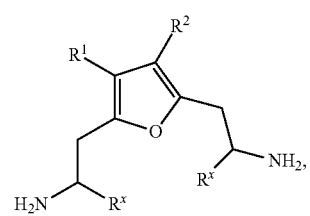
(B-IIa)

wherein $R^x$ is H or alkyl; and
$R^1$ and $R^2$ are independently H or alkyl;

the compound of formula (B-IIb) is:

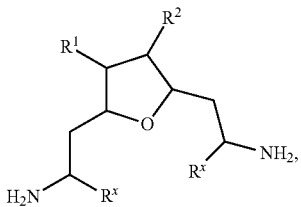
(B-IIb)

wherein $R^x$ is H or alkyl; and
$R^1$ and $R^2$ are independently H or alkyl;
the compound of formula (B-III) is:

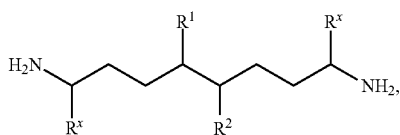
(B-III)

wherein $R^x$ is H or alkyl; and
$R^1$ and $R^2$ are independently H or alkyl;
the compound of formula (C) is:

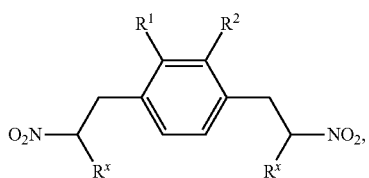
(C)

wherein $R^x$ is H or alkyl; and
$R^1$ and $R^2$ are independently H or alkyl;
the compound of formula (C-I) is:

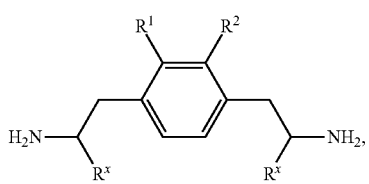
(C-I)

wherein $R^x$ is H or alkyl; and
$R^1$ and $R^2$ are independently H or alkyl;
the compound of formula (M) is:

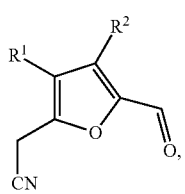
(M)

wherein $R^1$ and $R^2$ are independently H or alkyl;

the compound of formula (MN) is:

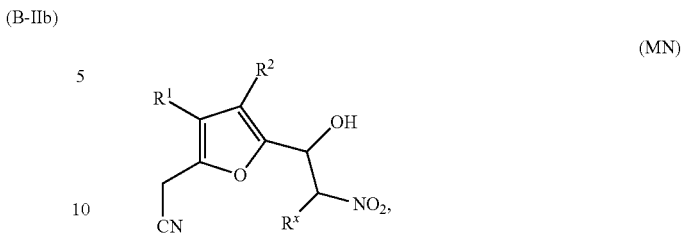
(MN)

wherein $R^1$, $R^2$, and $R^x$ are independently H or alkyl;
the compound of formula (N) is:

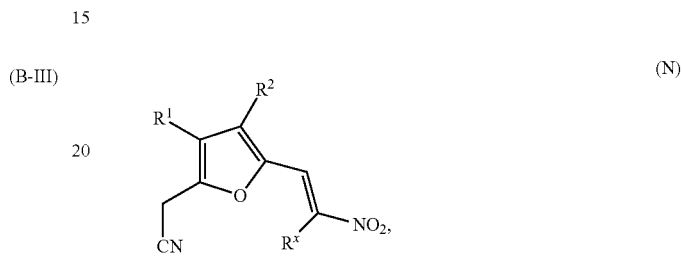
(N)

wherein $R^1$, $R^2$ and $R^x$ are independently H or alkyl;
the compound of formula (N-I) is:

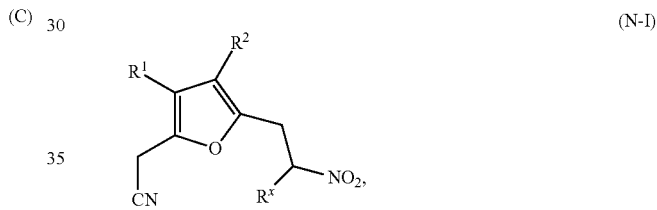
(N-I)

wherein $R^1$, $R^2$ and $R^x$ are independently H or alkyl;
the compound of formula (N-IIa) is:

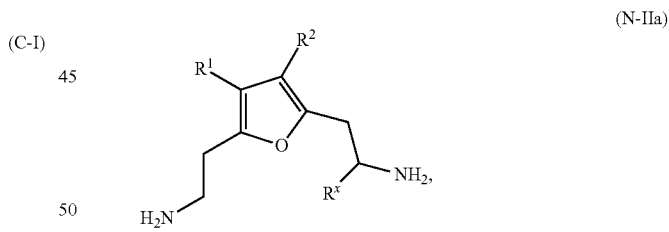
(N-IIa)

wherein $R^1$, $R^2$ and $R^x$ are independently H or alkyl;
the compound of formula (N-IIb) is:

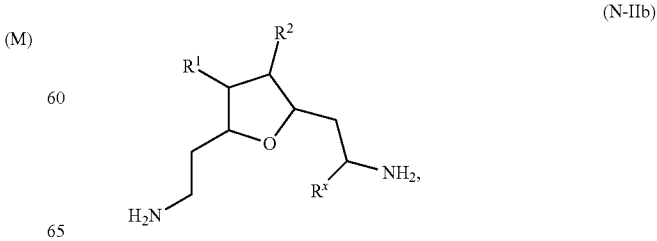
(N-IIb)

wherein $R^1$, $R^2$ and $R^x$ are independently H or alkyl;

the compound of formula (P) is:

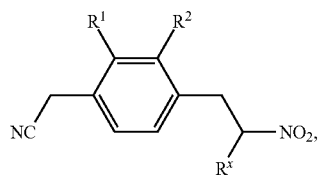

wherein $R^1$, $R^2$ and $R^x$ are independently H or alkyl;
the compound of formula (P-I) is:

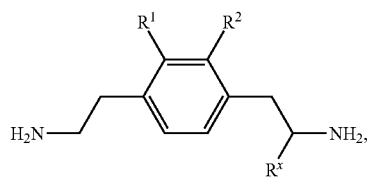

wherein $R^1$, $R^2$ and $R^x$ are independently H or alkyl;
the compound of formula (Q) is:

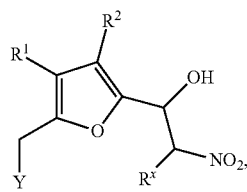

wherein Y is halo; and
$R^1$, $R^2$ and $R^x$ are independently H or alkyl; and
the compound of formula (R) is:

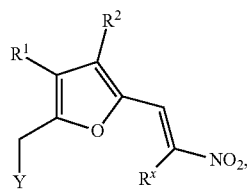

wherein Y is halo; and
$R^1$, $R^2$ and $R^x$ are independently H or alkyl.
73. The composition of embodiment 72, wherein $R^1$ and $R^2$ are H.
74. The composition of embodiment 72 or 73, wherein $R^x$ is H.
75. A compound having the structure:

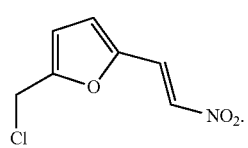 [SMILES: O=[N+]([O-])/C=C/c1ccc(CCl)o1]

76. The compound of embodiment 75, wherein the compound has an X-ray powder diffraction (XRPD) pattern substantially as shown in FIG. 5.
77. The compound of embodiment 75, wherein the compound has an X-ray powder diffraction (XRPD) pattern comprising at least a peak at about 39.8 degrees 2θ.
79. The compound of embodiment 77, wherein the XRPD pattern further comprises at least one additional peak at about 13.0 degrees 2θ, about 26.2 degrees 2θ, about 53.9 degrees 2θ, or about 69.0 degrees 2θ.
80. The compound of any one of embodiments 75 to 79, wherein the compound is solid form.
81. The compound of any one of embodiments 75 to 80, wherein the compound is crystalline.

EXAMPLES

The following Examples are merely illustrative and are not meant to limit any aspects of the present disclosure in any way.

Example 1

Synthesis of 2,5-bis(2-nitroethyl)furan from 2-(2-nitroethyl)-5-(2-nitrovinyl)furan

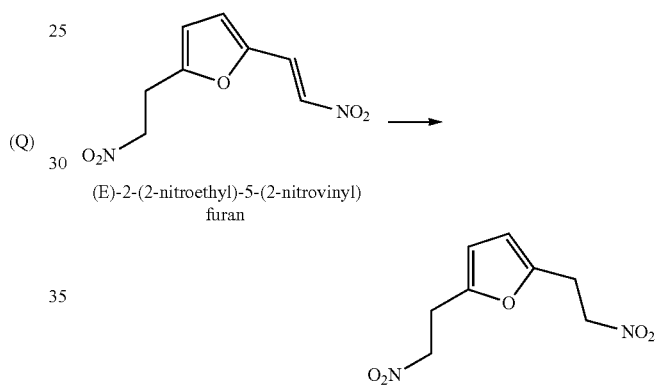

To a pressure Parr hydrogenator vessel is added 2-(2-nitroethyl)-5-(2-nitrovinyl)furan, Wilkinson's catalyst, and toluene. The atmosphere of the vessel is exchanged with hydrogen three times. Hydrogen is charged up to about 3 atms. The vessel is heated to 60° C., stirred at 400 rpm, and such reaction conditions are maintained for 8 hours. The vessel is then cooled to room temperature (about 22° C.). The hydrogen is evacuated and purged with air. The reaction mixture is diluted and the products are analyzed by gas chromatography/mass spectrometry (GC/MS).

Example 2

Synthesis of octane-1,8-diamine from 2-(2-nitroethyl)-5-(2-nitrovinyl)furan

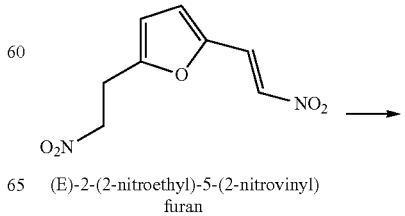

(E)-2-(2-nitroethyl)-5-(2-nitrovinyl)furan

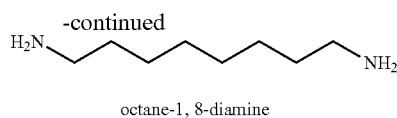

octane-1, 8-diamine

To a pressure Parr hydrogenator vessel is added 2-(2-nitroethyl)-5-(2-nitrovinyl)furan, Nafion SAC-13, Rh—Re/SiO₂, and water. The atmosphere of the vessel is exchanged with hydrogen three times. Hydrogen is charged up to about 5 atms. The vessel is heated to 80° C., stirred at 400 rpm, and such reaction conditions are maintained for 8 hours. The vessel is then cooled to room temperature (about 22° C.). The hydrogen is evacuated and purged with air. The reaction mixture is diluted and the products are analyzed by GC/MS.

Example 3

Synthesis of 2,2'-(furan-2,5-diyl)diethanamine and 2,2'-(tetrahydrofuran-2,5-diyl)diethanamine from 2-(2-nitroethyl)-5-(2-nitrovinyl)furan

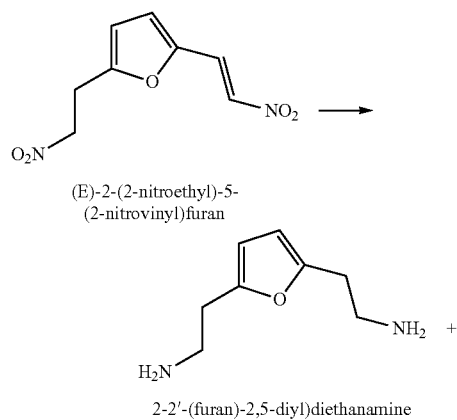

(E)-2-(2-nitroethyl)-5-(2-nitrovinyl)furan 2-2'-(furan)-2,5-diyl)diethanamine 2-2'-(tetrahydrofuran-2,5-diyl)diethanamine To a pressure Parr hydrogenator vessel is added 2-(2-nitroethyl)-5-(2-nitrovinyl)furan, 2 wt % Pd/C, and toluene. The atmosphere of the vessel is exchanged with hydrogen three times. Hydrogen is charged up to about 5 atms. The vessel is heated to 80° C., stirred at 400 rpm, and such reaction conditions are maintained for 8 hours. The vessel is then cooled to room temperature (about 22° C.). The hydrogen is evacuated and purged with air. The reaction mixture is diluted and the products are analyzed by GC/MS.

Example 4

Synthesis of 1-[5-(chloromethyl)furan-2-yl]-2-nitroethanol

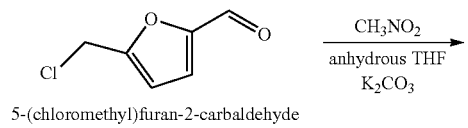

5-(chloromethyl)furan-2-carbaldehyde 1-(5-(chloromethyl)furan-2-yl)-2-nitroethan-1-ol To a 1.0 L round bottomed flask equipped with a stir bar was added 5-chloromethyl-2-furfural (0.1038 mol), anhydrous tetrahydrofuran (500 ml), and nitromethane (1.0245 mol) under argon. Anhydrous potassium carbonate (0.1094 mol) was then added while stirring. The reaction mixture was then allowed to stir at 27 degrees Celsius under argon and the reaction was monitored by thin-layer chromatography, and a new spot was detected by TLC under UV light (4:1 hexane-ethyl acetate, Rf=0.21). After three hours, the liquid portion of the reaction mixture was filtered over a 1.5 um glass fiber filter into a 2 L three-necked round bottomed flask. A sample of the filtrate was removed for analysis, and was characterized by NMR and GC-MS.

¹H NMR (600 MHz, THF-d8) δ ppm 4.62-4.69 (m, 1H) 4.65 (br d, J=1.76 Hz, 2H) 4.75-4.80 (m, 1H) 5.33-5.38 (m, 1H) 5.47 (br s, 1H) 6.35 (d, J=2.93 Hz, 1H) 6.39 (br d, J=2.93 Hz, 1H); ¹³C NMR (151 MHz, THF-d8) δ ppm 37.75, 65.41, 79.65, 108.66, 111.12, 151.34, 155.18. GC Agilent J&W HP-5 19091L-413, 3 m×320 μm, temp ramp: initial 5° C. held for 9 minutes then ramps to 25° C. at 10° C./min then ramps to 71° C. at 80° C./min then ramps to 72° C. at 0.5° C./min then ramps to 200° C. at 100° C./min and held for 3 min, $t_R$=17.31 min. GC-MS (EI) found 205 [M]⁺, C₇H₈O₄NCl requires 205.

The NMR and MS data confirmed the synthesis of 1-[5-(chloromethyl)furan-2-yl]-2-nitroethanol.

Example 5

Synthesis of 2-(chloromethyl)-5-(E)-(2-nitroethenyl)furan Using Hydrochloric Acid

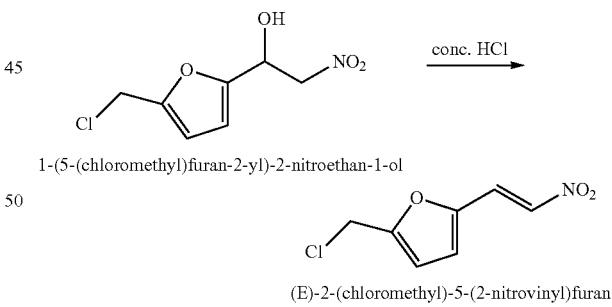

1-(5-(chloromethyl)furan-2-yl)-2-nitroethan-1-ol (E)-2-(chloromethyl)-5-(2-nitrovinyl)furan The 2.0 L, three-neck flask containing the reaction mixture used to prepare 1-[5-(chloromethyl)furan-2-yl]-2-nitroethanol in Example 4 above was fitted with a 500 ml pressure-equalizing addition funnel in the middle port, a glass thermometer fitted into a thermocouple in the right port, and a glass stopper in the left port. Concentrated hydrochloric acid (500 ml) was then added to the addition funnel and the acid was added drop-wise into the reaction mixture at room temperature. After 75 ml of acid was added over the course of 10 minutes, it was noted that the temperature of the reaction had increased from 25 degrees Celsius to 35 degrees Celsius. The reaction temperature was maintained between 20-25 degrees Celsius using an ice-water bath, and the additional acid was added. The reaction was then allowed to continue stirring at room temperature and the reaction was monitored by thin-layer chromatography, which indicated nearly complete consumption of starting material and the formation of a new spot (4:1 hexane-ethyl acetate, Rf=0.58). After 5 hours, the contents of the flask were poured into a 3.0 L separatory funnel and diluted into 1.5 L of ethyl acetate. Saturated sodium bicarbonate was then added until a bi-phase was observed. The organic and aqueous layers were then separated and the aqueous layer was back-extracted with ethyl acetate (1×600 ml). The combined organics were dried over sodium sulfate, filtered, and evaporated under reduced pressure to yield a brown oil. The oil was purified by flash chromatography (SiO$_2$, EtOAc/Hexane, 1:4) and recrystallized (boiling hexane, drop-wise addition of EtOAc) to yield yellow crystals. The purified product was characterized by NMR and GC-MS.

$^1$H NMR (600 MHz, CHLOROFORM-d) δ ppm 4.59 (s, 2H) 6.54 (d, J=3.00 Hz, 1H) 6.84 (d, J=3.00 Hz, 1H) 7.54 (d, J=13.00 Hz, 1H) 7.73 (d, J=13.00 Hz, 1H). $^{13}$C NMR (151 MHz, CHLOROFORM-d) δ ppm 36.63, 112.81, 120.66, 124.93, 135.45, 147.12, 154.62. GC Agilent J&W HP-5 19091L-413, 3 m×320 μm, temp ramp: initial 40° C. ramp to 25° C. at 10° C./min then ramps to 200° C. at 40° C./min and held for 10 min, t$_R$=6.69 min. GC-MS (EI) found 187 [M]$^+$, C$_7$H$_6$O$_3$NCl requires 187.

The NMR and MS data confirmed the synthesis of 2-(chloromethyl)-5-(E)-(2-nitroethenyl)furan.

The purified product was analyzed by X-ray powder diffraction (XRPD). The XRPD was performed at 40 kV and 44 mA. Depicted in FIG. 5 is the XRPD pattern obtained.

Example 6

Synthesis of 2-(chloromethyl)-5-(E)-(2-nitroethenyl) furan Using Phosphoric Acid

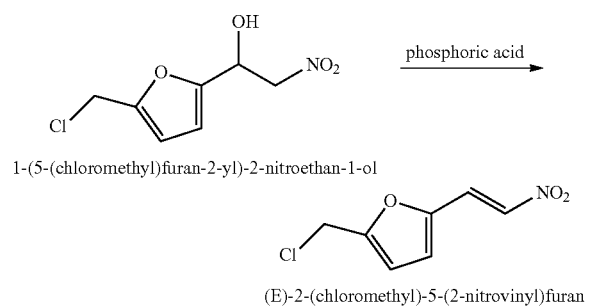

To a 2.0 L, three-neck round bottomed flask containing the filtered reaction mixture used to prepare 1-[5-(chloromethyl)furan-2-yl]-2-nitroethanol (as described in Example 4 above) is added a 500 ml pressure-equalizing addition funnel, a thermometer, which monitors the temperature of the reaction mixture, and a glass stopper. The addition funnel is then charged with 85% phosphoric acid (400 ml). The acid is then added dropwise to the constantly stirring reaction mixture and the temperature is maintained at 20-25 degrees Celsius for 3 h, and then heated as necessary to consume the starting material. After reaction completion, the contents of the flask are poured into a 3.0 L separatory funnel containing 1.5 L of ethyl acetate. Saturated sodium bicarbonate (1.0 L) is added carefully with light shaking until a bi-phase is produced. The organic and aqueous layers are separated and the aqueous is back-extracted with ethyl acetate (1×600 ml). The combined organics are dried over sodium sulfate, filtered, and evaporated under reduced pressure to yield crude product mixture.

Example 7

Synthesis of 2-(chloromethyl)-5-(E)-(2-nitroethenyl) furan Using Poly(4-vinylyridine)

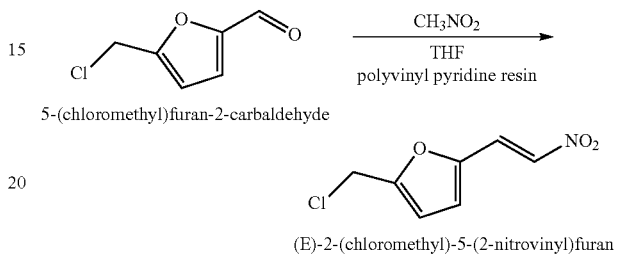

To a 1.0 L round bottomed flask equipped with an egg-shaped stir bar is added 5-chloromethyl-2-furfural (14.45 g, 0.1 mol), tetrahydrofuran (500 ml) and nitromethane (6.41 g, 0.105 mol). Oven dried Reillex® 425 poly(4-vinylpyridine) resin (19.10 g) is then added in one addition and the temperature is maintained at 20-25 degrees Celsius for 3 h, and then heated as necessary to consume the starting material. After reaction completion, the reaction mixture is then filtered and the solvent is evaporated under reduced pressure to yield crude product mixture.

Example 8

Synthesis of (E)-2-(2-nitrobut-1-en-1-yl)-5-(2-nitrobutyl)furan

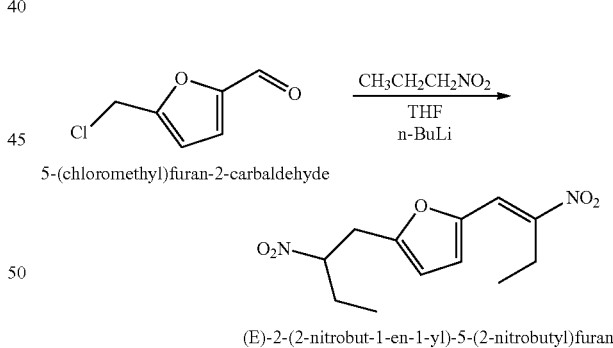

To a 2.0 L flamed dried, argon flushed round bottomed flask equipped with a stir bar is added 1-nitropropane (18.71 g, 0.2100 mol, 2.1 eq.) and tetrahydrofuran (400 ml). The liquid is then cooled to −78 degrees Celsius and n-butyllithium in hexanes (2.0 eq) is added dropwise. The resulting mixture is allowed to stir for 30 minutes at −78 degrees Celsius before a second addition of n-butyllithium (2.0 eq) is added, followed by a second mixing period. To this is added 5-chloromethyl-2-furfural (14.45 g, 0.1000 mol, 1 eq) dissolved in tetrahydrofuran (100 ml) dropwise. The reaction is slowly brought to room temperature followed by heating to reflux. The reaction mixture is then brought to room temperature and concentrated hydrochloric acid (500 ml) is added slowly over the course of an hour, maintaining the reaction temperature at 20-25 degrees Celsius. After reaction completion, the contents of the flask are poured into a 3.0 L separatory funnel containing 1.5 L of ethyl acetate. Saturated sodium bicarbonate (1.0 L) is then added carefully with light shaking until a bi-phase is produced. The organic and aqueous layers are then separated and the aqueous is back-extracted with ethyl acetate (1×600 ml). The combined organics are then dried over sodium sulfate, filtered, and evaporated under reduced pressure to yield crude product mixture.

Example 9

Synthesis of [5-(1-hydroxy-2-nitroethyl)furan-2-yl]acetonitrile

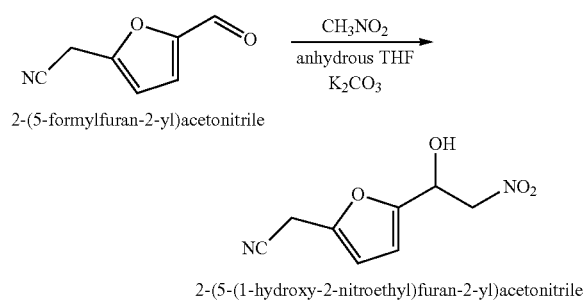

To a 1.0 L round bottomed flask equipped with an egg-shaped stir bar is added (5-formylfuran-2-yl)acetonitrile (13.50 g, 0.0999 mol), anhydrous tetrahydrofuran (500 ml), and nitromethane (61.04 g, 1.0000 mol) under argon and constant stirring. Anhydrous potassium carbonate (14.55 g, 0.1053 mol) is then added in one addition and while maintaining constant stirring. The reaction mixture is then allowed to stir constantly at 25 degrees Celsius and increased as necessary to complete the reaction, under an argon atmosphere. The reaction mixture is then filtered from solids to give product in solution.

Example 10

Synthesis of (5-[(E)-2-nitroethenyl]furan-2-yl)acetonitrile

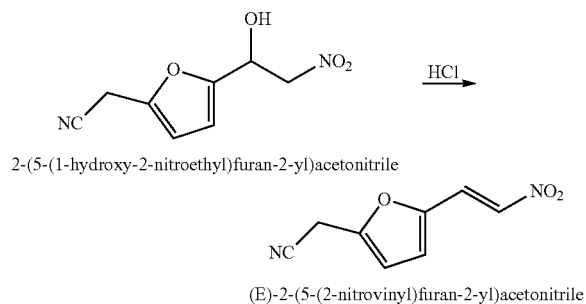

To a 2.0 L, three-neck round bottomed flask containing the reaction mixture used to prepare [5-(1-hydroxy-2-nitroethyl)furan-2-yl]acetonitrile (see Example 9 above) is added a 500 ml pressure-equalizing addition funnel, a thermometer, which monitors the temperature of the reaction mixture, and a glass stopper. The concentrated hydrochloric acid (500 ml) is then added to the addition funnel and the acid is drop wise added into the constantly stirring reaction mixture and the temperature is maintained at 20-25 degrees Celsius. After reaction completion, the contents of the flask are poured into a 3.0 L separatory funnel containing 1.5 L of ethyl acetate. Saturated sodium bicarbonate (1.0 L) is then added carefully with light shaking until a bi-phase is produced. The organic and aqueous layers are then separated and the aqueous is back-extracted with ethyl acetate (1×600 ml). The combined organics are then dried over sodium sulfate, filtered, and evaporated under reduced pressure to yield crude product mixture.

What is claimed is:

1. A composition, comprising:
a compound of formula (Q):

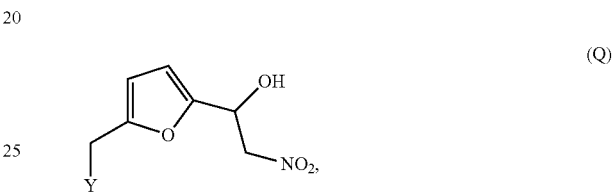

wherein Y is halo.

2. The composition of claim 1, wherein Y is chloro or bromo.

3. The composition of claim 1, wherein the composition further comprises a compound of formula (R):

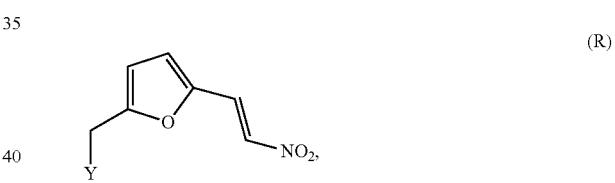

or any isomers thereof, wherein Y is halo.

4. The composition of claim 3, wherein the composition comprises the (Z) isomer of the compound of formula (R).

5. The composition of claim 3, wherein the composition comprises 2-(chloromethyl)-5-[(Z)-2-nitroethenyl]furan.

6. The composition of claim 3, wherein the composition comprises the (E) isomer of the compound of formula (R).

7. The composition of claim 3, wherein the composition comprises 2-(chloromethyl)-5-[(E)-2-nitroethenyl]furan.

8. The composition of claim 7, wherein the composition comprises a crystalline form of 2-(chloromethyl)-5-[(E)-2-nitroethenyl]furan.

9. The composition of claim 7, wherein the composition comprises 2-(chloromethyl)-5-[(E)-2-nitroethenyl]furan having an X-ray powder diffraction pattern substantially as shown in FIG. 5.

10. The composition of claim 7, wherein the composition comprises 2-(chloromethyl)-5-[(E)-2-nitroethenyl]furan having an X-ray powder diffraction pattern that comprises at least one peak at about 39.8 degrees 2θ.

11. The composition of claim 10, wherein the 2-(chloromethyl)-5-[(E)-2-nitroethenyl]furan has an X-ray powder diffraction pattern that further comprises at least one additional peak at about 13.0 degrees 2θ, about 26.2 degrees 2θ, about 53.9 degrees 2θ, or about 69.0 degrees 2θ.

12. The composition of claim 1, further comprising a polymerization catalyst.

13. The composition of claim 3, wherein Y is chloro or bromo.

14. The composition of claim 3, further comprising a polymerization catalyst.

* * * * *